(12) United States Patent
Chang et al.

(10) Patent No.: US 12,392,774 B2
(45) Date of Patent: Aug. 19, 2025

(54) BIOSENSOR SYSTEM WITH INTEGRATED MICRONEEDLE

(71) Applicant: Taiwan Semiconductor Manufacturing Company, Ltd., Hsinchu (TW)

(72) Inventors: Allen Timothy Chang, Hsinchu (TW); Jui-Cheng Huang, Hsinchu (TW); Wen-Chuan Tai, Hsinchu (TW); Yu-Jie Huang, Kaohsiung (TW)

(73) Assignee: Taiwan Semiconductor Manufacturing Company, Ltd., Hsinchu (TW)

( * ) Notice: Subject to any disclaimer, the term of this patent is extended or adjusted under 35 U.S.C. 154(b) by 0 days.

(21) Appl. No.: 18/447,974

(22) Filed: Aug. 10, 2023

(65) Prior Publication Data
US 2024/0044889 A1 Feb. 8, 2024

Related U.S. Application Data

(62) Division of application No. 17/104,059, filed on Nov. 25, 2020, now Pat. No. 12,123,871.
(Continued)

(51) Int. Cl.
*G01N 33/543* (2006.01)
*G01N 27/414* (2006.01)

(52) U.S. Cl.
CPC ... *G01N 33/54373* (2013.01); *G01N 27/4145* (2013.01); *G01N 27/4148* (2013.01)

(58) Field of Classification Search
CPC ......... G01N 33/54373; G01N 27/4145; G01N 27/4148; G01N 27/27; G01N 27/414;
(Continued)

(56) References Cited

U.S. PATENT DOCUMENTS 8,506,529 B1   8/2013   Yang
8,871,549 B2 * 10/2014  Ellis-Monaghan .......... H01L 29/66477
                                              257/253

(Continued)

FOREIGN PATENT DOCUMENTS

CN   103180240 A   6/2013
CN   104051512 A   9/2014
(Continued)

OTHER PUBLICATIONS

Translation of Description of CN 108226257A from Espacenet, 2018, 15 pages (Year: 2018).
(Continued)

*Primary Examiner* — Bao-Thuy L Nguyen
*Assistant Examiner* — Ellis Follett Lusi
(74) *Attorney, Agent, or Firm* — Merchant & Gould P.C.

(57) ABSTRACT

A biosensor system package includes: a transistor structure in a semiconductor layer having a front side and a back side, the transistor structure comprising a channel region; a buried oxide (BOX) layer on the back side of the semiconductor layer, wherein the buried oxide layer has an opening on the back side of the channel region, and an interface layer covers the back side over the channel region; a multi-layer interconnect (MLI) structure on the front side of the semiconductor layer, the transistor structure being electrically connected to the MLI structure; and a cap structure attached to the buried oxide layer, the cap structure comprising a microneedle.

20 Claims, 48 Drawing Sheets

Related U.S. Application Data

(60) Provisional application No. 62/967,850, filed on Jan. 30, 2020.

(58) Field of Classification Search
CPC .......... G01N 27/3271; G01N 27/4035; G01N 27/4071; H01L 2224/02166; H01L 2224/48091; H01L 2224/73265; H01L 23/49827; H01L 21/50; H01L 23/49838; H01L 23/5386; H01L 2924/1306; H01L 2924/13091; A61B 5/14514; A61B 5/685; B81B 7/0006; B81B 7/0032; B81B 7/02; B81B 2201/0214; B81B 2201/05; B81C 1/00015; B81C 1/00119; B81C 1/00261; B81C 2203/01
USPC ......... 435/287.2, 287.3, 287.9, 288.2, 288.5; 257/253, 414, 194, 288, 24
See application file for complete search history.

(56) References Cited

U.S. PATENT DOCUMENTS

| | | | |
|---|---|---|---|
| 9,080,969 | B2 | 7/2015 | Liu et al. |
| 9,299,640 | B2 | 3/2016 | Lin |
| 10,131,540 | B2 | 11/2018 | Yu et al. |
| 10,509,008 | B2 | 12/2019 | Liao et al. |
| 10,556,792 | B2 | 2/2020 | Lee et al. |
| 10,852,271 | B2 | 12/2020 | Chen et al. |
| 11,747,298 | B2 | 9/2023 | Chang et al. |
| 12,123,846 | B2 | 10/2024 | Chang et al. |
| 12,123,871 | B2 | 10/2024 | Chang et al. |
| 2010/0164117 | A1 | 7/2010 | Chen |
| 2011/0244676 | A1 | 10/2011 | Chen et al. |
| 2012/0211885 | A1 | 8/2012 | Choi et al. |
| 2013/0168740 | A1 | 7/2013 | Chen |
| 2013/0200438 | A1 | 8/2013 | Liu et al. |
| 2014/0264467 | A1 | 9/2014 | Cheng et al. |
| 2016/0320337 | A1 | 11/2016 | Cheng et al. |
| 2017/0067890 | A1 | 3/2017 | Lin et al. |
| 2017/0158500 | A1* | 6/2017 | Chang .................... H01L 24/11 |
| 2017/0365587 | A1 | 12/2017 | Hung et al. |
| 2018/0019187 | A1 | 1/2018 | Lagouge et al. |
| 2018/0172627 | A1 | 6/2018 | Chang et al. |
| 2018/0238827 | A1 | 8/2018 | Cheng et al. |
| 2018/0313783 | A1 | 11/2018 | Cheng et al. |
| 2018/0338713 | A1 | 11/2018 | Polsky et al. |
| 2019/0145927 | A1 | 5/2019 | Huang et al. |
| 2024/0410855 | A1 | 12/2024 | Chang et al. |
| 2025/0035623 | A1 | 1/2025 | Chang et al. |

FOREIGN PATENT DOCUMENTS

| | | | |
|---|---|---|---|
| CN | 105977282 A | 9/2016 | |
| CN | 108226257 A | 6/2018 | |
| CN | 109307701 A | 2/2019 | |
| DE | 10 2016 125 295 A1 | 6/2018 | |
| DE | 10 2018 124 826 A1 | 5/2019 | |
| EP | 2 421 596 B1 | 11/2015 | |
| EP | 1 967 581 B1 | 8/2016 | |
| KR | 10-2018-0018287 A | 2/2018 | |
| TW | 201638814 A | 11/2016 | |
| WO | 2008/008845 A2 | 1/2008 | |
| WO | WO-2018026830 A1 * | 2/2018 | ......... G01N 27/4145 |

OTHER PUBLICATIONS

Chinese Office Action for Application No. 202110129817.9 mailed Jun. 26, 2024.

Notice of Allowance for Korean Application No. 10-2021-0002574 mailed Jul. 24, 2023.

\* cited by examiner

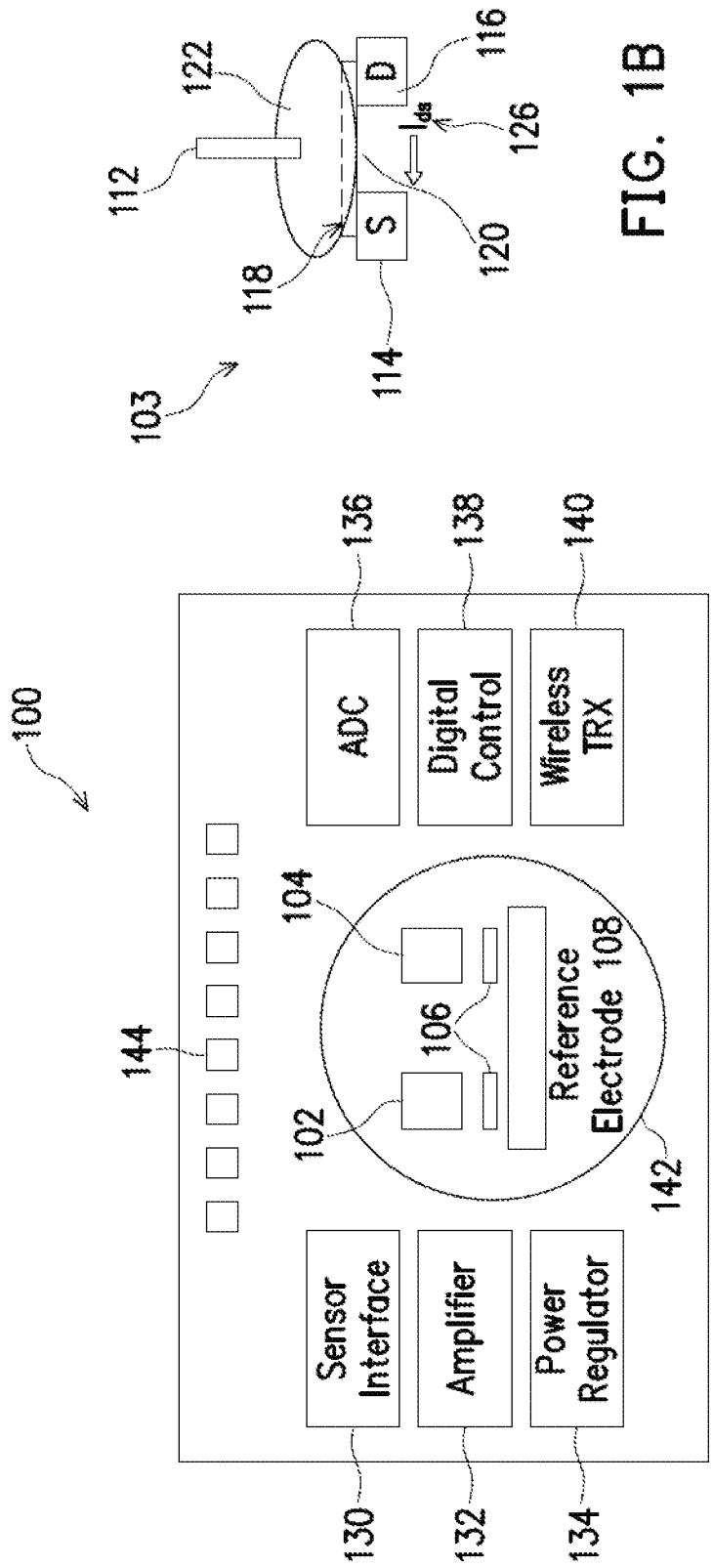

BIOSENSOR SYSTEM WITH INTEGRATED MICRONEEDLE

PRIORITY CLAIM AND CROSS-REFERENCE

This application is a divisional of U.S. patent application Ser. No. 17/104,059, filed Nov. 25, 2020, which claims the benefit of U.S. Provisional Application No. 62/967,850, filed Jan. 30, 2020, the disclosure of which is hereby incorporated by reference in its entirety.

BACKGROUND

Biosensors are devices for sensing and detecting biomolecules and operate on the basis of electronic, electrochemical, optical, and mechanical detection principles. Biosensors that include transistors are sensors that electrically sense charges, photons, and mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes, can quickly convert electric signals, and can be easily applied to integrated circuits (ICs) and microelectromechanical systems (MEMS).

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIG. 1A is a block diagram of an example biosensor system in accordance with some embodiments.

FIG. 1B is a schematic diagram of an example biosensor used in the biosensor system of FIG. 1A in accordance with some embodiments.

DETAILED DESCRIPTION

Figure 2A:
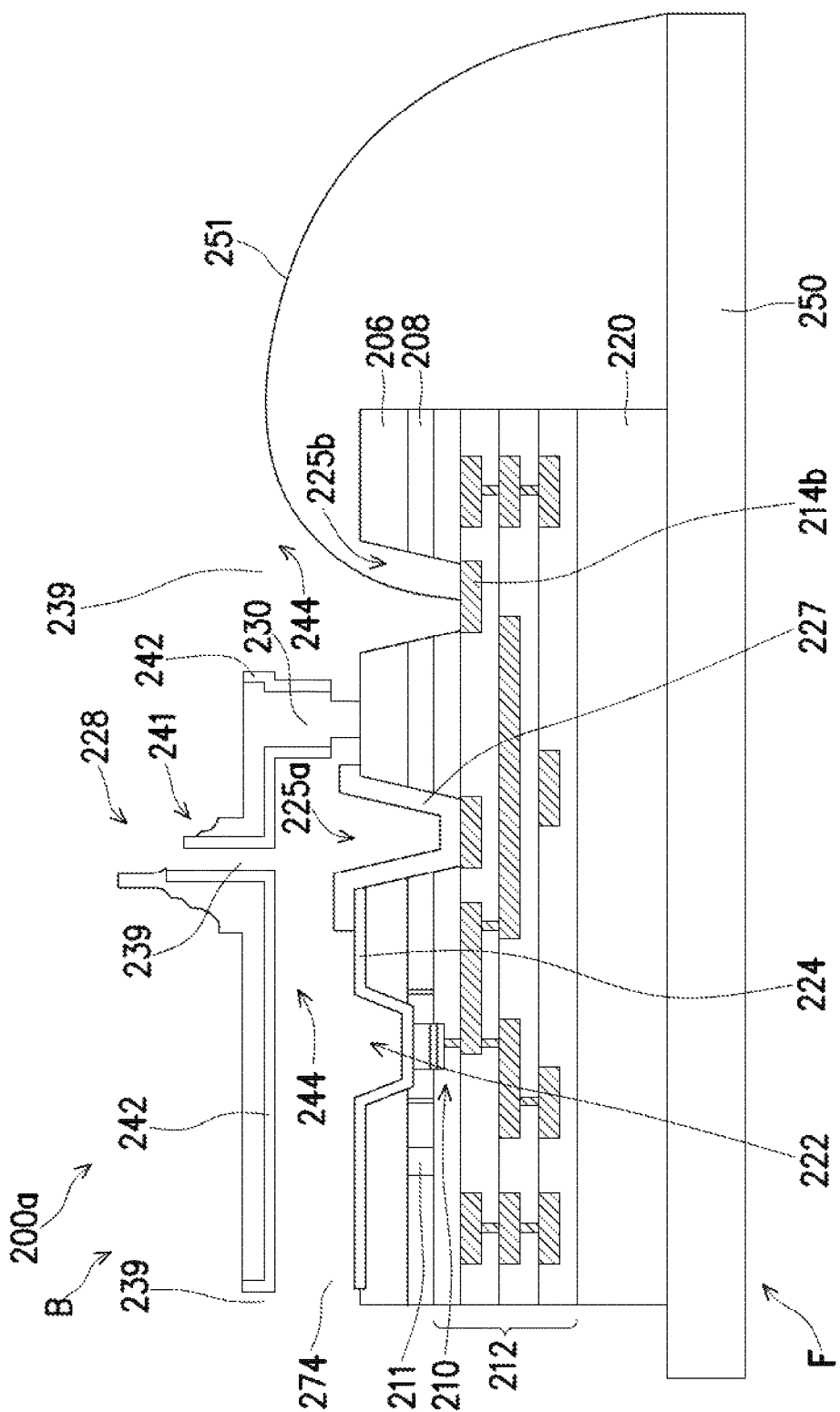
FIG. 2A is a cross-sectional diagram illustrating a biosensor system package in accordance with some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

In general, the term "bioFET" as used herein refers to a field-effect transistor (FET) that includes a layer of immobilized capture reagents that act as surface receptors to detect the presence of a target analyte of biological origin. A bioFET is a field-effect sensor with a semiconductor transducer, according to some embodiments. One advantage of bioFETs is the prospect of label-free operation. Specifically, bioFETs enable the avoidance of costly and time-consuming labeling operations such as the labeling of an analyte with, for instance, fluorescent or radioactive probes. The analytes for detection by a bioFET will normally be of biological origin, such as—without limitation—proteins, carbohydrates, lipids, tissue fragments, or portions thereof. A BioFET can be part of a broader genus of FET sensors that may also detect any chemical compound (known in the art as a "ChemFET") or any other element, including ions such as protons or metallic ions (known in the art as an "ISFET"). This disclosure applies to all types of FET-based sensors ("FET sensor").

"Capture reagent," as used herein, is a molecule or compound capable of binding the target analyte or target reagent, which can be directly or indirectly attached to a substantially solid material. The capture reagent can be a chemical, and specifically any substance for which there exists a naturally occurring target analyte (e.g., an antibody, polypeptide, DNA, RNA, cell, virus, etc.) or for which a target analyte can be prepared, and the capture reagent can bind to one or more target analytes in an assay.

"Target analyte," as used herein, is the substance to be detected in the test sample using the present disclosure. The target analyte can be a chemical, and specifically any substance for which there exists a naturally occurring capture reagent (e.g., an antibody, polypeptide, DNA, RNA, cell, virus, etc.) or for which a capture reagent can be prepared, and the target analyte can bind to one or more capture reagents in an assay. "Target analyte" also includes any antigenic substances, antibodies, or combinations thereof. The target analyte can include a protein, a peptide, an amino acid, a carbohydrate, a hormone, a steroid, a vitamin, a drug including those administered for therapeutic purposes as well as those administered for illicit purposes, a bacterium, a virus, and metabolites of or antibodies to any of the above substances.

"Biomarker," as used herein, means a measurable indicator of the severity or presence of some disease state. More generally a biomarker is anything that can be used as an indicator of a particular disease state or some other physiological state of an organism. A biomarker can be a substance that is introduced into an organism as a means to examine organ function or other aspects of health. For example, rubidium chloride is used in isotopic labeling to evaluate perfusion of heart muscle. It can also be a substance whose detection indicates a particular disease state, for example, the presence of an antibody may indicate an infection. More specifically, a biomarker indicates a change in expression or state of a protein that correlates with the risk or progression of a disease, or with the susceptibility of the disease to a given treatment. Biomarkers can be characteristic biological properties or molecules that can be detected and measured in parts of the body like the blood or tissue. They may indicate either normal or diseased processes in the body. Biomarkers can be specific cells, molecules, or genes, gene products, enzymes, or hormones. Complex organ functions or general characteristic changes in biological structures can also serve as biomarkers.

"Test sample," as used herein, means the composition, solution, substance, gas, or liquid containing the target analyte to be detected and assayed using the present disclosure. The test sample can contain other components besides the target analyte, can have the physical attributes of a liquid, or a gas, and can be of any size or volume, including for example, a moving stream of liquid or gas. The test sample can contain any substances other than the target analyte as long as the other substances do not interfere with the binding of the target analyte with the capture reagent or the specific binding of the first binding member to the second binding member. Examples of test samples include, but are not limited to, naturally-occurring and non-naturally occurring samples or combinations thereof. Naturally-occurring test samples can be synthetic or synthesized. Naturally-occurring test samples include body or bodily fluids isolated from anywhere in or on the body of a subject, including, but not limited to, blood, plasma, serum, urine, saliva or sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof, and environmental samples such as ground water or waste water, soil extracts, air, and pesticide residues or food-related samples.

Detected substances can include, for example, nucleic acids (including DNA and RNA), hormones, different pathogens (including a biological agent that causes disease or illness to its host, such as a virus (e.g., H7N9 or HIV), a protozoan (e.g., *Plasmodium*-causing malaria), or a bacteria (e.g., *E. coli* or *Mycobacterium tuberculosis*)), proteins, antibodies, various drugs or therapeutics or other chemical or biological substances, including hydrogen or other ions, non-ionic molecules or compounds, polysaccharides, small chemical compounds such as chemical combinatorial library members, and the like. Detected or determined parameters may include, but are not limited to, pH changes, lactose changes, changing concentration, particles per unit time where a fluid flows over the device for a period of time to detect particles (e.g., particles that are sparse), and other parameters.

As used herein, the term "immobilized," when used with respect to, for example, a capture reagent, includes substantially attaching the capture reagent at a molecular level to a surface. For example, a capture reagent may be immobilized to a surface of the substrate material using adsorption techniques including non-covalent interactions (e.g., electrostatic forces, van der Waals, and dehydration of hydrophobic interfaces) and covalent binding techniques where functional groups or linkers facilitate attaching the capture reagent to the surface. Immobilizing a capture reagent to a surface of a substrate material may be based on the properties of the substrate surface, the medium carrying the capture reagent, and the properties of the capture reagent. In some cases, a substrate surface may be first modified to have functional groups bound to the surface. The functional groups may then bind to biomolecules or biological or chemical substances to immobilize them thereon.

A biosensor system includes, among other things, a sensing chip and a microneedle. The microneedle and the sensing chip often are fabricated separately and later assembled manually, which is not a scalable manufacturing solution.

In accordance with some embodiments, a wafer-level packaging solution to fabricate sensing chips and cap structures with microneedles together is provided. The solution may be used for biomarker monitoring and/or drug delivery. Since microneedles and sensing chips are fabricated together, there is no need to assemble the microneedles and the sensing chips manually. It is a more scalable manufacturing solution and may lower manufacturing costs. The increased integration further makes it possible to construct a biomarker monitoring and drug delivery feedback system. When providing therapy to a patient, such a feedback system may prevent delivery of too much drug which could become toxic to the patient. The feedback system is a closed-loop feedback system where the drug delivery is dependent on the biomarker levels. A large number of biosensors may be employed as an array for each microfluidic chamber of the cap structure served by microneedle(s). This provides better statistical analysis of the sensing results and reduces the signal to noise ratio (SNR) of the results. In accordance with some embodiments, the biosensor system package may be connected to a separate chip/die through wire bonding. In accordance with some embodiments, the biosensor system package may be connected to a separate chip/die through a through-substrate via (TSV) structure.

FIG. 1A is a block diagram of an example biosensor system 100 in accordance with some embodiments. FIG. 1B is a schematic diagram of an example biosensor 103 used in the biosensor system 100 of FIG. 1A in accordance with some embodiments. As shown in FIG. 1A, the example biosensor system 100 may include, among other things, a biosensor array 102, a control sensor array 104, temperature sensors 106, a reference electrode 108, a sensor interface 130, an amplifier 132, a power regulator 134, an analog-to-digital converter (ADC) 136, a digital control module 138, a wireless transceiver (TRX) 140, a heater 142, and bonding pads 144.

The biosensor array 102 may have at least one sensing element for detecting a biological or chemical analyte. The biosensor array 102 may include an array of biosensors (e.g., a biosensor 103 shown in FIG. 1B), where one or more of the biosensors in the array are functionalized to detect a particular target analyte. Different ones of the biosensors may be functionalized using different capture reagents for detecting different target analytes. The biosensors may be arranged in a plurality of rows and columns, forming a 2-dimensional array of biosensors. In some embodiments, each row of biosensors is functionalized using a different capture reagent. In some embodiments, each column of biosensors is functionalized using a different capture reagent. In some embodiments, a certain range of rows and columns of biosensors are functionalized using a different capture reagent. Further details regarding an example biosensor 103 is provided below with reference to FIG. 1B.

The control sensor array 104 has similar structures with the biosensor array 102. The control sensor array 104 provides reference signals to be compared with the signals generated at the biosensor array 102, to generate differential signals. The sensor interface 130 interfaces with the biosensor array 102 and the control sensor array 104. The resultant differential signals are further amplified by the amplifier 132. The reference electrode 108 provides a reference potential. The reference electrode 108 may be made of one of the following materials: Ag/AgCl, Cu/CuSO$_4$, AgCl, Au, and P. For Ag/AgCl, a chemical treatment may be required on the deposited and patterned Ag layer to create the AgCl. For Cu/CuSO$_4$, a chemical treatment may be required on the deposited and patterned Cu layer to create the CuSO$_4$. For applications where the sensing has to be done at certain temperatures, the heater 142 can adjust the temperature of the biosensor array 102 and the control sensor array 104 based on feedback signals detected by the temperature sensors 106. The ADC 136 may convert analog signals amplified by the amplifier to digital signals. The digital control module 138 may act as a controller for the biosensor system 100. The bonding pads 144 are used for bonding the biosensor system to other chips or printed circuit board (PCB). Alternatively, the wireless transceiver 140 may transmit and receive data via wireless communication.

As shown in FIG. 1B, the example biosensor 103 may include, among other things, a fluid gate 112, a source region 114, a drain region 116, a sensing film 118, a channel region 120. A fluid 122 is over the sensing film 118. The fluid 122 may contain analyte not shown. The sensing film 118 may be an electrically and chemically insulating layer that separates the fluid 122 from the channel region 120. The sensing film 118 may include, among other things, a layer of a capture reagent. The capture reagent is specific to an analyte and capable of binding the target analyte or target reagent. Upon binding of the analyte, changes in the electrostatic potential at the surface of the sensing film 118 occur, which in turn results in an electrostatic gating effect of the biosensor 103, and a measurable change in a current $I_{ds}$ 126 between the source and drain electrodes. A voltage applied to the fluid gate 112 may also change the $I_{ds}$ 126.

Figure 2B:
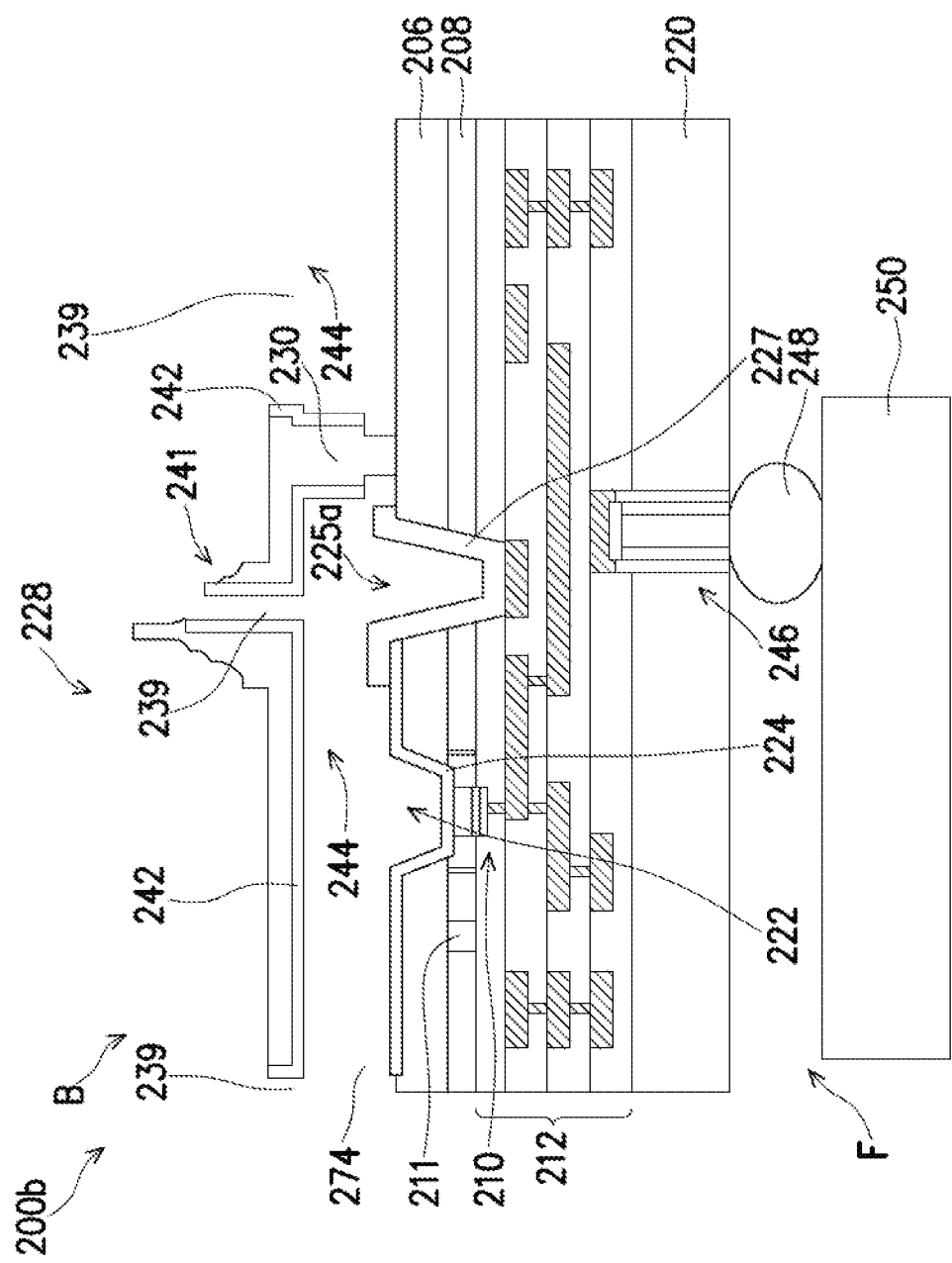
FIG. 2B is a cross-sectional diagram illustrating another biosensor system package 200b in accordance with some embodiments.
Figure 6A:
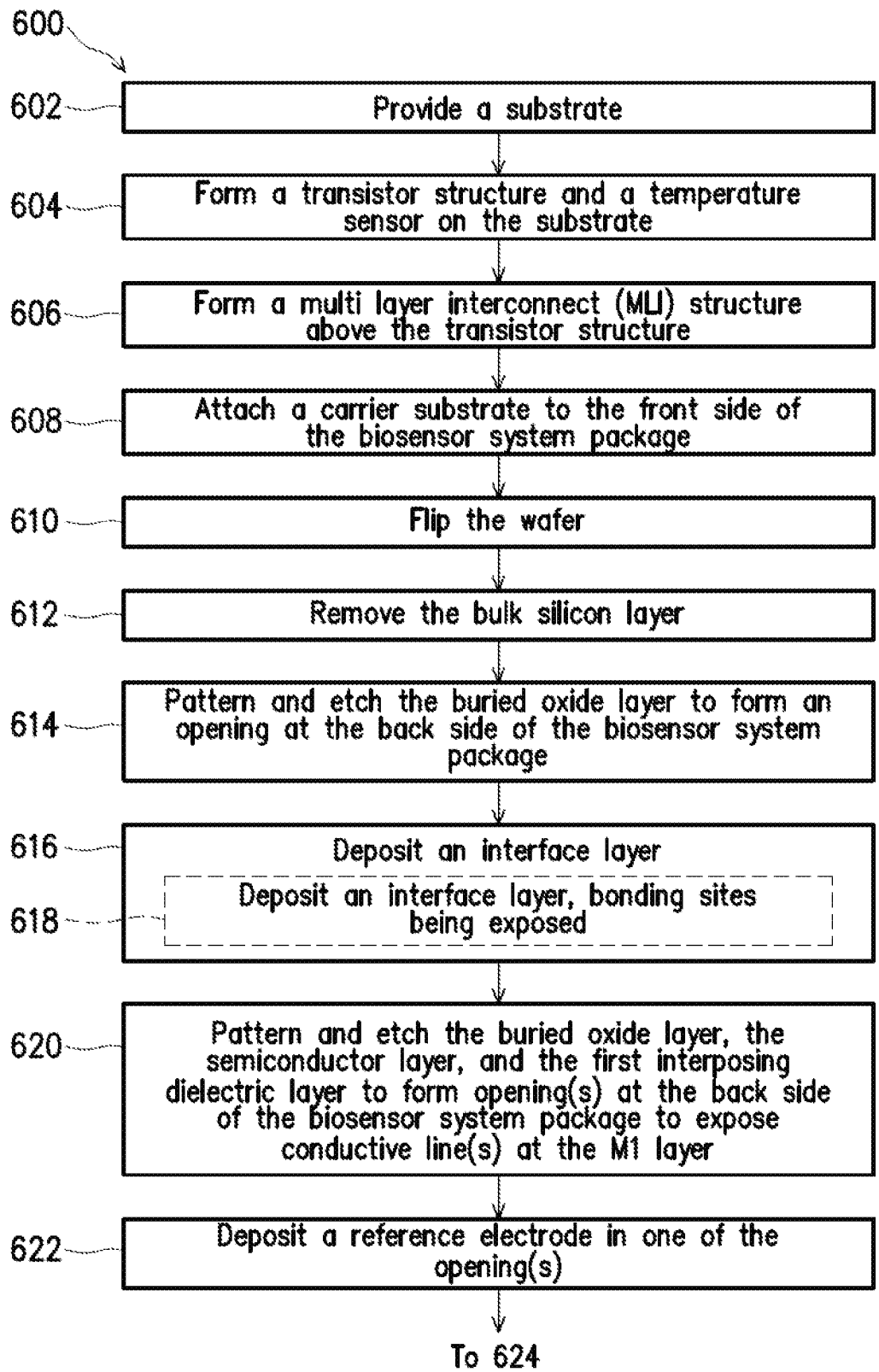
FIG. 6A and FIG. 6B are flowcharts illustrating a method of fabricating the biosensor system packages of FIG. 2A and FIG. 2B, respectively, in accordance with some embodiments.
Figure 6B:
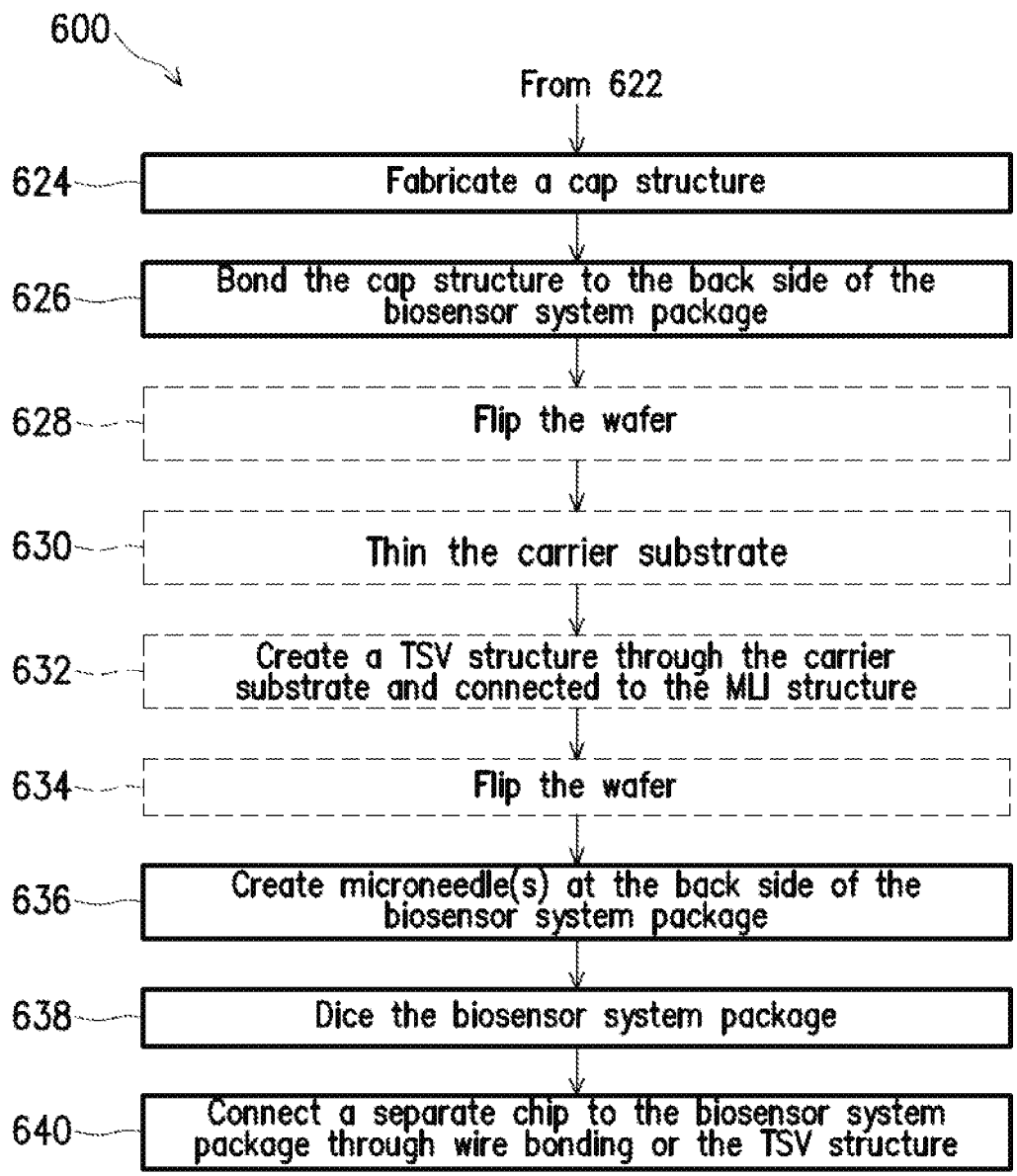
Figure 6C:
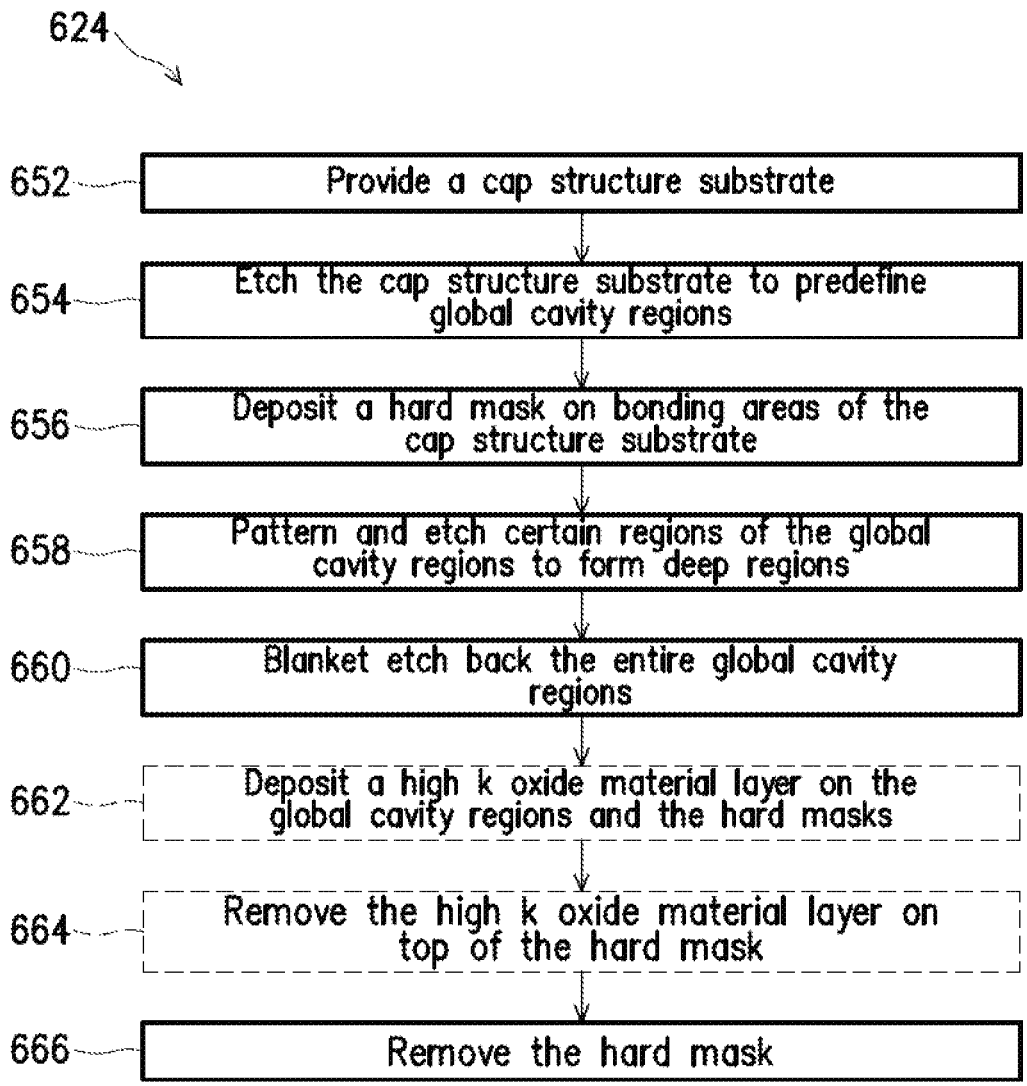
FIG. 6C is a flowchart illustrating the step 624 of the method of FIG. 6A and FIG. 6B in accordance with some embodiments.
Figure 6D:
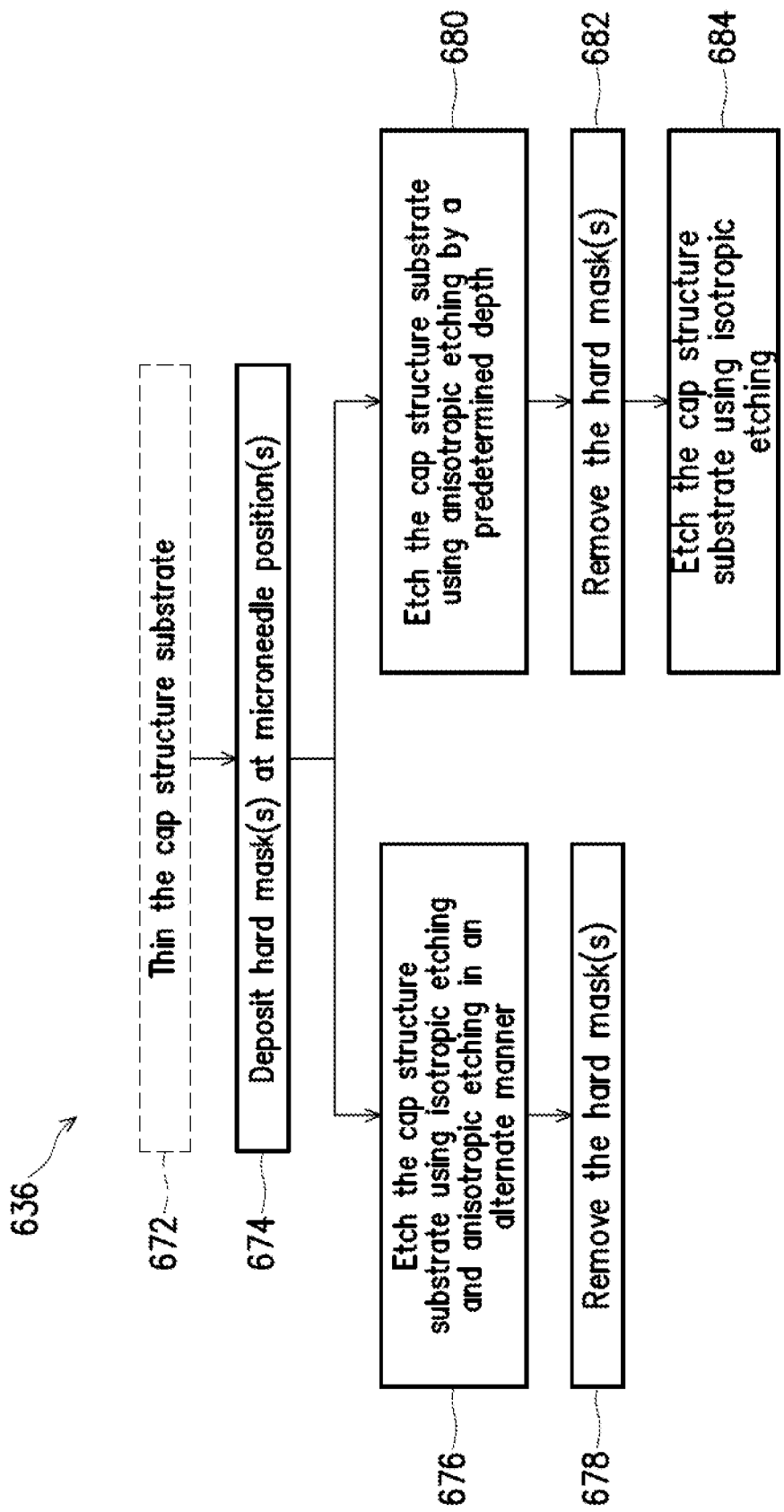
FIG. 6D is a flowchart illustrating the step 636 of the method of FIG. 6A and FIG. 6B in accordance with some embodiments.
Figure 6E:
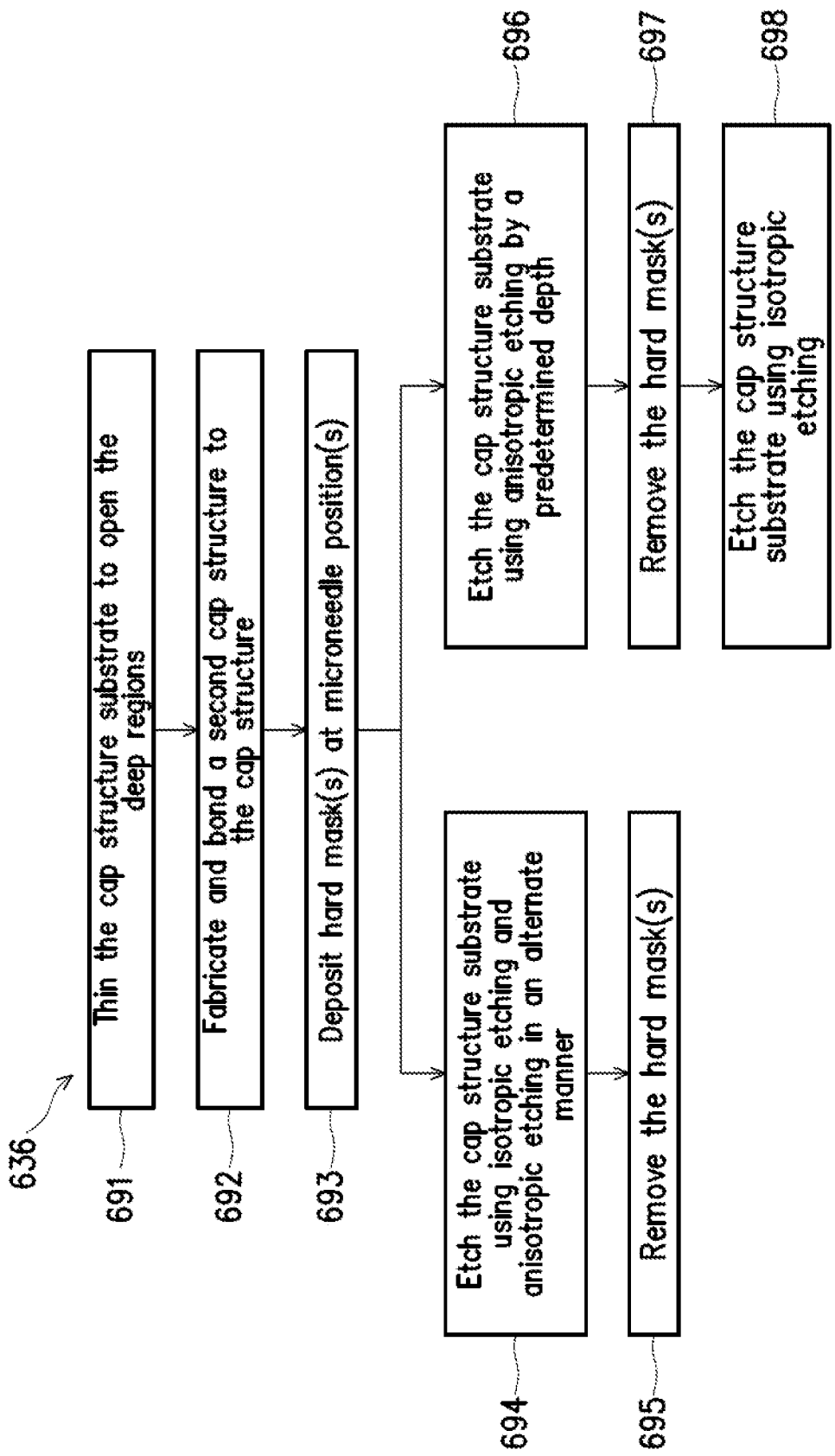
FIG. 6E is another flowchart illustrating the step 636 of the method of FIG. 6A and FIG. 6B in accordance with some embodiments.

FIG. 2A is a cross-sectional diagram illustrating a biosensor system package 200a in accordance with some embodiments. FIG. 2B is a cross-sectional diagram illustrating another biosensor system package 200b in accordance with some embodiments. FIG. 6A and FIG. 6B are flowcharts illustrating a method of fabricating the biosensor system package 200a and 200b (collectively 200) of FIG. 2A and FIG. 2B, respectively, in accordance with some embodiments. FIG. 6C is a flowchart illustrating the step 624 of the method 600 in accordance with some embodiments. FIG. 6D is a flowchart illustrating the step 636 of the method 600 in accordance with some embodiments. FIG. 6E is another flowchart illustrating the step 636 of the method 600 in accordance with some embodiments. It should be noted that additional steps can be provided before, during, and after the method 600, and some of the steps described below can be replaced or eliminated, for additional embodiments of the method. Further, it should be noted that the method 600 is a CMOS-compatible process flow. FIGS. 7-38 are cross-sectional diagrams illustrating the biosensor system package constructed according to one or more steps of the method of FIG. 6A and FIG. 6B in accordance with some embodiments. It should be noted that FIGS. 2A-2B and 7-38 are schematic and are not drawn to scale.

As shown in FIGS. 2A and 2B, each of the biosensor system package 200a and 200b (collectively 200) has a front side (F) and a back side (B). In the example shown in FIG. 2A and FIG. 2B, each of the biosensor system package 200*a* and 200*b* includes, among other things, a buried oxide (BOX) layer 206, a semiconductor layer 208, a transistor structure (i.e., a FET) 210, a temperature sensor 211, a multilevel-interconnect (MLI) structure 212, a carrier substrate 220, a separate chip/die (e.g., a RAM and data processing chip) 250, a trench 222, an interface layer (e.g., a high-k material layer) 224, a reference electrode 227, and a cap structure 228. The separate chip 250 is connected to the biosensor system package 200*a* of FIG. 2A by wire bonding, while the separate chip 250 is connected to the biosensor system package 200*b* of FIG. 2B by a through-substrate via (TSV) structure 246 and a solder bump 248. The TSV structure 246 is at the front side (F). The cap structure 228 is attached to the back side (B). The cap structure 228 includes, among other things, a cap structure substrate 230, chamber(s) 244, a microneedle 241, an inlet 274, and optionally a high-k dielectric material layer 242. The chamber 244 can accommodate fluid samples to be tested. Details of the components of the biosensor system package 200 will be described below with reference to FIGS. 6A-6E and 7-38.

Figure 3A:
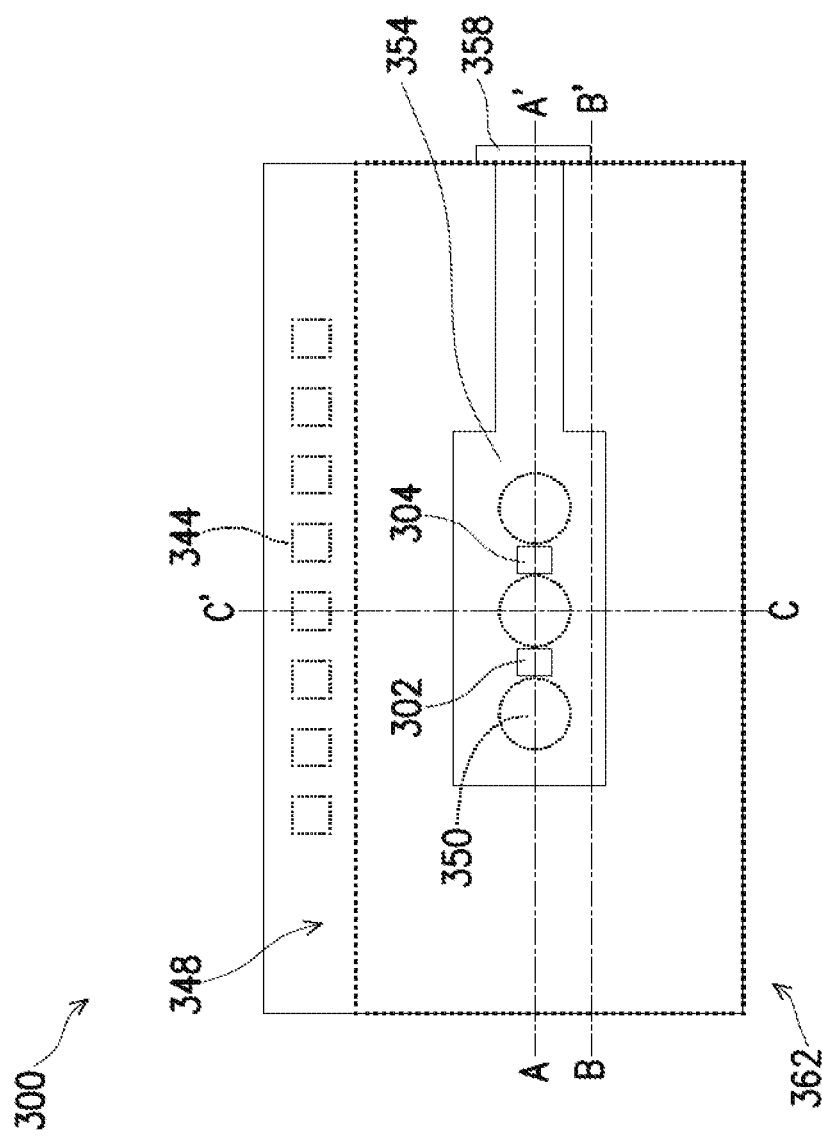
FIG. 3A is a top view of an integrated continuous biomarker monitoring and treatment chip in accordance with some embodiments.
Figure 3B:
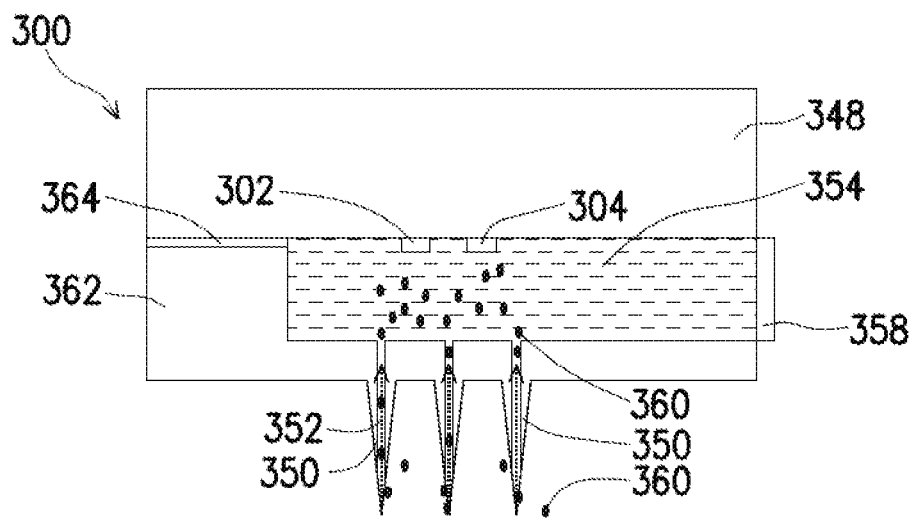
FIG. 3B is a cross-sectional diagram illustrating the cross section of the integrated continuous biomarker monitoring and treatment chip along a line A-A' of FIG. 3A in accordance with some embodiments.
Figure 3C:
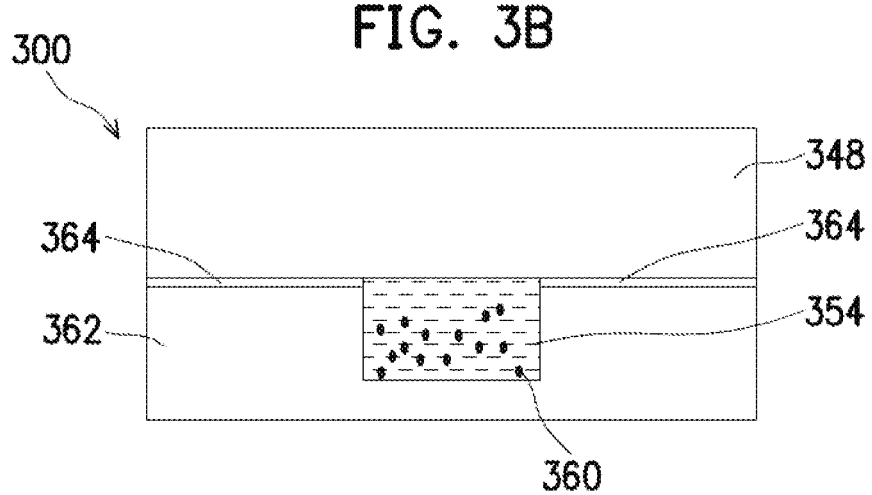
FIG. 3C is a cross-sectional diagram illustrating the cross section of the integrated continuous biomarker monitoring and treatment chip along a line B-B' of FIG. 3A in accordance with some embodiments.
Figure 3D:
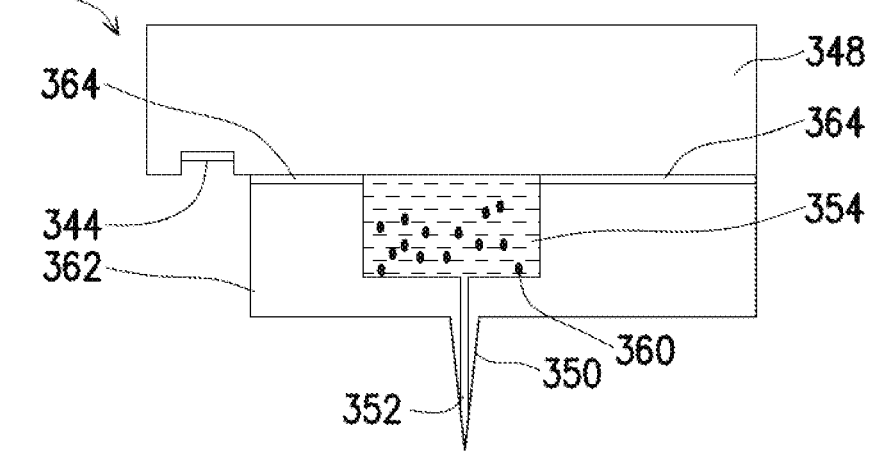
FIG. 3D is a cross-sectional diagram illustrating the cross section of the integrated continuous biomarker monitoring and treatment chip along a line C-C' of FIG. 3A in accordance with some embodiments.
Figure 3E:
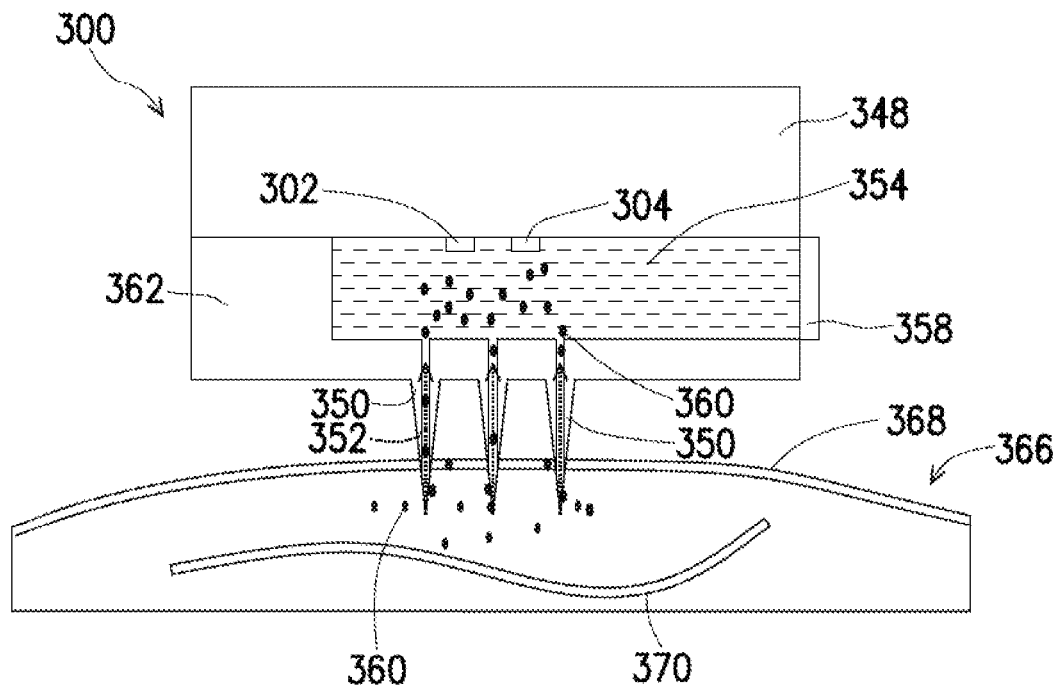
FIG. 3E is a diagram illustrating the use of the integrated continuous biomarker monitoring and treatment chip of FIG. 3A in accordance with some embodiments.
Figure 3F:
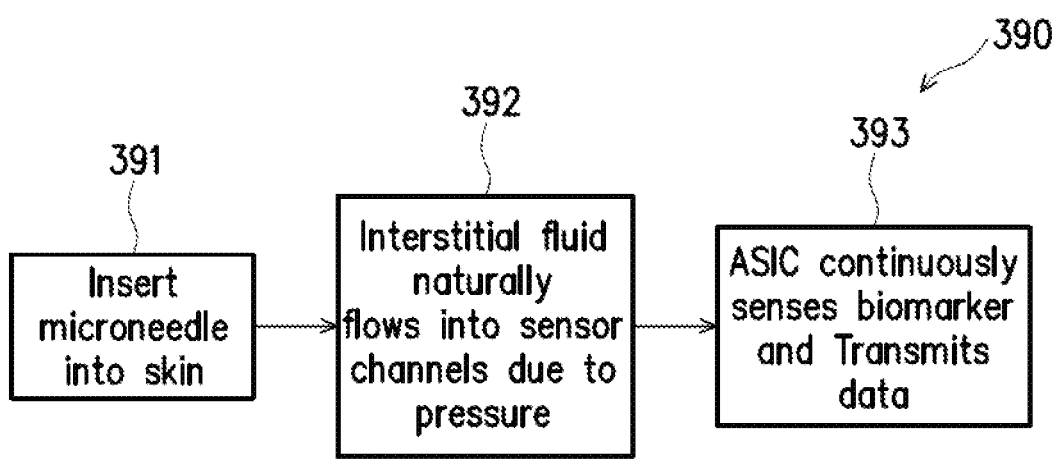
FIG. 3F is a flowchart illustrating a method of operating the integrated continuous biomarker monitoring and treatment chip of FIG. 3A in accordance with some embodiments.

FIG. 3A is a top view of an integrated continuous biomarker monitoring and treatment chip 300 in accordance with some embodiments. FIG. 3B is a cross-sectional diagram illustrating the cross section of the integrated continuous biomarker monitoring and treatment chip 300 along a line A-A' of FIG. 3A in accordance with some embodiments. FIG. 3C is a cross-sectional diagram illustrating the cross section of the integrated continuous biomarker monitoring and treatment chip 300 along a line B-B' of FIG. 3A in accordance with some embodiments. FIG. 3D is a cross-sectional diagram illustrating the cross section of the integrated continuous biomarker monitoring and treatment chip 300 along a line C-C' of FIG. 3A in accordance with some embodiments. FIG. 3E is a diagram illustrating the use of the integrated continuous biomarker monitoring and treatment chip 300 of FIG. 3A in accordance with some embodiments. FIG. 3F is a flowchart illustrating a method 390 of operating the integrated continuous biomarker monitoring and treatment chip 300 of FIG. 3A in accordance with some embodiments.

As shown in FIGS. 3A-3D, the integrated continuous biomarker monitoring and treatment chip 300 may include, among other things, a complementary metal-oxide-semiconductor (CMOS) application-specific integrated circuit (ASIC) 348, a cap structure 362 attached to the back side of the CMOS ASIC 348, and a gas-liquid separation membrane 358. In the example shown in FIGS. 3A-3D, the cap structure 362 is attached to the CMOS ASIC 348 via wafer bonding structures 364, though other means of bonding may be employed. The example CMOS ASIC 348 has, among other things, a biosensor array 302 and a control sensor array 304 at the back side of the CMOS ASIC 348. The example cap structure 362 has, among other things, a fluid chamber 354 and multiple microneedles 350. The fluid chamber 354 may accommodate fluid which may contain biomarker molecules (e.g., glucose molecules) 360. The biosensor array 302 and the control sensor array 304 may detect the existence and density of the biomarker molecules 360 as explained above. The fluid enters the fluid chamber 354 via the multiple microneedles 350. The number of microneedles 350 may vary as needed. For each microneedle 350, there is a (silicon) microneedle channel 352 that connects the fluid chamber 354 with outside. The gas-liquid separation membrane 358 is configured to eliminate air bubbles in the fluid chamber 354 since only gas can pass the gas-liquid separation membrane 358.

Referring to FIGS. 3E and 3F, the integrated continuous biomarker monitoring and treatment chip 300 is used for continuous biomarker monitoring, and the method 390 of operating the integrated continuous biomarker monitoring and treatment chip 300 starts at step 391. At step 391, the microneedles 350 are inserted into a skin 368. Specifically, the microneedles 350 penetrate the skin 368 of a body (e.g., human body) 366. Biomarker molecules (e.g., glucose molecules) 360 may exist in the body 366 (beneath the skin 368, inside and around the blood vessel 370). At step 392, interstitial fluid may naturally flow into the fluid chamber 354 via the microneedle channels 352 of the microneedles 350 due to pressure. As a result, the biomarker molecules 360 enter the fluid chamber 354 as well. At step 393, the CMOS ASIC 348 with the biosensor array 302 and the control sensor array 304 continuously senses the biomarker molecules 360 and transmits data. Specifically, the biosensor array 302, along with the control sensor array 304, may detect the existence and density of the biomarker molecules 360. The detected signal is further processed (e.g., amplified, converted, etc.) by the CMOS ASIC 348. The result data may be transmitted via either the bonding pads 344 shown in FIG. 3A or alternatively the wireless transceiver module 140 shown in FIG. 1A. As such, the integrated continuous biomarker monitoring and treatment chip 300 may continuously sense the biomarker molecules 360, which in turn may be used for diagnose or treatment of certain diseases (e.g., diabetes) related to the biomarker molecules 360.

Figure 4A:
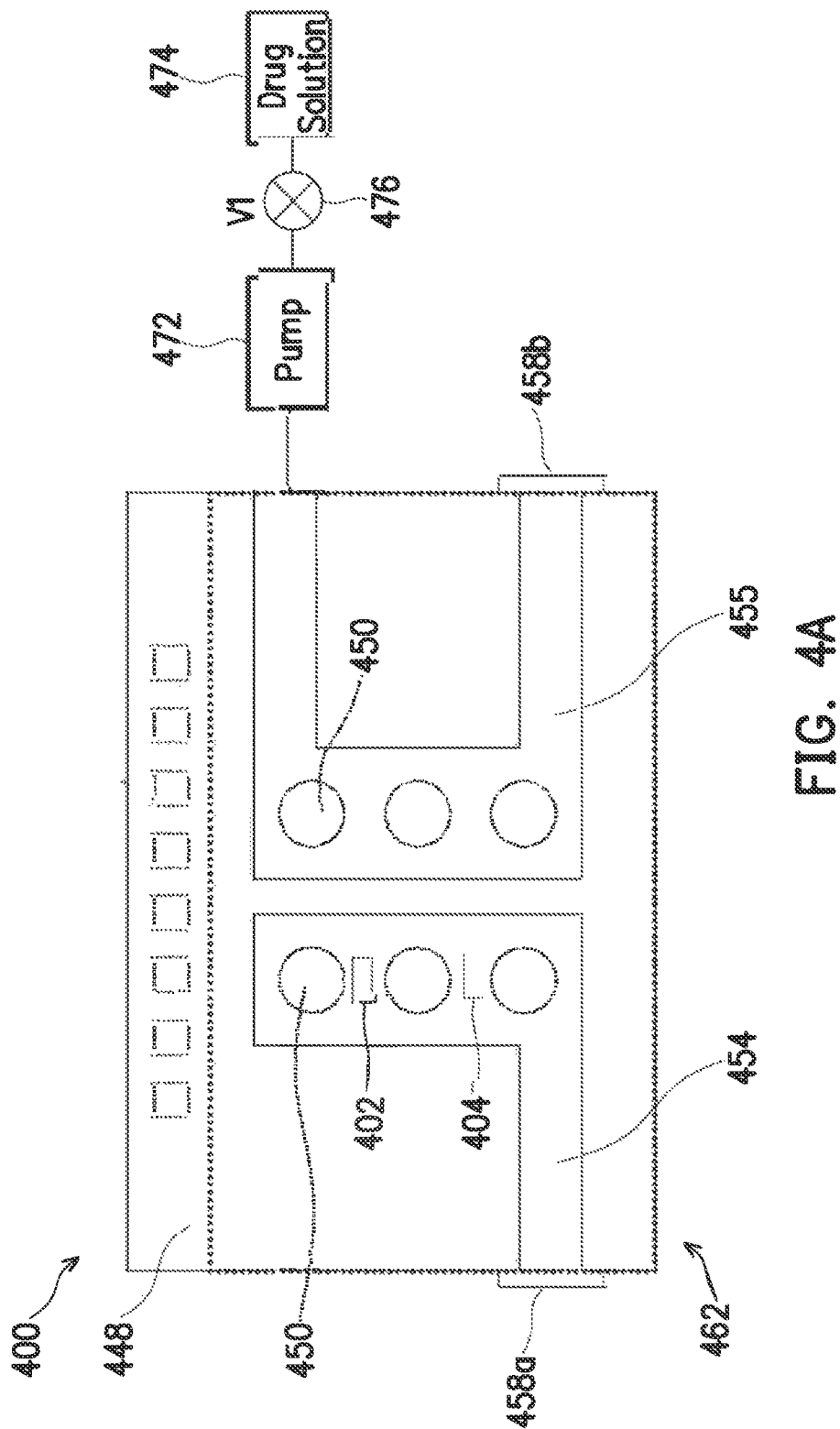
FIG. 4A is a top view of a simultaneously biomarker monitoring and drug releasing treatment chip and the application thereof in accordance with some embodiments.
Figure 4B:
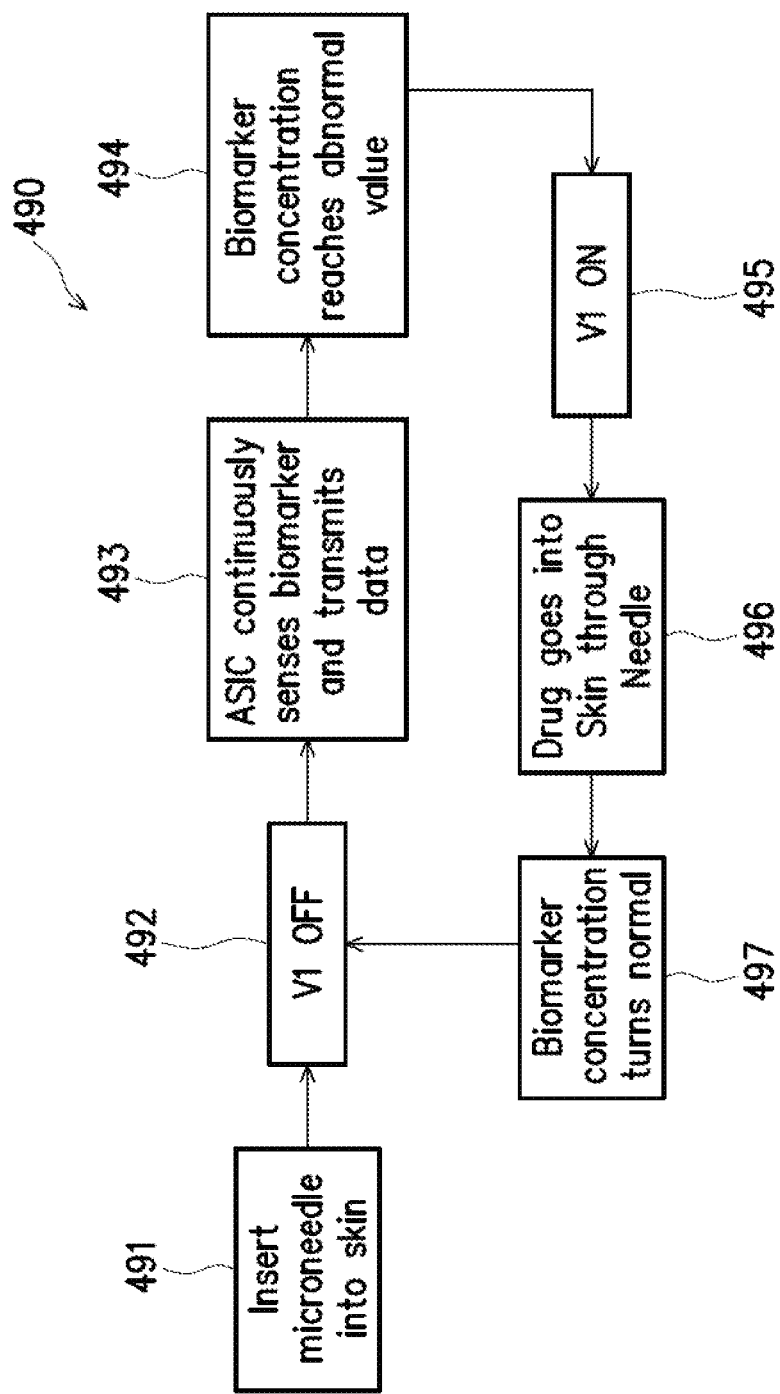
FIG. 4B is a flowchart illustrating a method for simultaneous biomarker monitoring and drug releasing treatment chip of FIG. 4A in accordance with some embodiments.

FIG. 4A is a top view of a simultaneously biomarker monitoring and drug releasing treatment chip 400 and the application thereof in accordance with some embodiments. FIG. 4B is a flowchart illustrating a method 490 for simultaneous biomarker monitoring and drug releasing treatment chip 400 of FIG. 4A in accordance with some embodiments.

As shown in FIG. 4A, the simultaneously biomarker monitoring and drug releasing treatment chip 400 may include, among other things, a CMOS ASIC 448, a cap structure 462 attached to the back of the CMOS ASIC 448, and two gas-liquid separation membranes 458*a* and 458*b*. In the example shown in FIG. 4A, the cap structure 462 is attached to the CMOS ASIC 448 via wafer bonding structures not shown, though other means of bonding may be employed. The example CMOS ASIC 448 has, among other things, a biosensor array 402 and a control sensor array 404 at the back of the CMOS ASIC 448. The example cap structure 462 has, among other things, a fluid chamber 454, a drug channel 455, and multiple microneedles 450. The fluid chamber 454 may accommodate fluid which may contain biomarker molecules (e.g., glucose molecules) not shown. The biosensor array 402 and the control sensor array 404 may detect the existence and density of the biomarker molecules as explained above. The fluid enters the fluid chamber 454 via the multiple microneedles 450. The number of microneedles 450 may vary as needed. On the other hand, the drug channel may accommodate drug solution 474 which is originally outside the simultaneously biomarker monitoring and drug releasing treatment chip 400. The drug solution 474, outside the simultaneously biomarker monitoring and drug releasing treatment chip 400, is connected to the drug channel 455 through a fluidics valve 476 and a pump 472. The fluidics valve 476 can be turned on and off based on control signals. When the fluidics valve 476 is turned on, the drug solution 474 can be pumped into the drug channel 455 for delivery via the microneedles 450. The gas-liquid separation membranes 458a and 458b are configured to eliminate air bubbles in the fluid chamber 454 and the drug channel 455, respectively.

Referring to FIG. 4B and FIG. 4A, the simultaneously biomarker monitoring and drug releasing treatment chip 400 is used for simultaneously biomarker monitoring and drug releasing treatment, and the method 490 for simultaneous biomarker monitoring and drug releasing treatment chip starts at step 491. At step 491, the microneedles 450 are inserted into a skin not shown. Specifically, the microneedles 450 penetrate the skin of a body (e.g., human body) not shown. Biomarker molecules (e.g., glucose molecules) not shown may exist in the body. Interstitial fluid not shown may naturally flow into the fluid chamber 454 via the microneedles 450 due to pressure. As a result, the biomarker molecules not shown may enter the fluid chamber 454 as well. At step 492, the fluidics valve 476 is turned off. As such, the drug solution 474 cannot flow into the drug channel 455. At step 493, the CMOS ASIC 448 with the biosensor array 402 and the control sensor array 404 continuously senses the biomarker molecules and transmits data. Specifically, the biosensor array 402, along with the control sensor array 404, may detect the existence and density of the biomarker molecules. The detected signal is further processed (e.g., amplified, converted, etc.) by the CMOS ASIC 448. At step 494, the CMOS ASIC 448 determines that the biomarker concentration reaches an abnormal value (e.g., above a threshold concentration). Then at step 495, the fluidics valve 476 is turned on. As a result, at step 496, the drug solution 474 flows into the drug channel 455 (e.g., pumped by the pump 472) and subsequently flows into the skin/body through the microneedles 450. As such, the drug solution 474 is delivered and the drug releasing treatment begins. On the other hand, the CMOS ASIC 448 still continuously senses the biomarker molecules and transmits data as at step 493. Due to the drug releasing treatment, the biomarker concentration becomes lower over time. At step 497, the CMOS ASIC 448 determines that the biomarker concentration turns normal (e.g., below the threshold concentration) again. As a result, the fluidics valve 476 is turned off again such that the drug solution 474 cannot flow into the drug channel 455. Accordingly, the method 490 can achieve simultaneous biomarker monitoring and drug releasing treatment with one integrated chip. In other words, the biomarker concentration is being constantly monitored and the drug releasing treatment is triggered automatically based on the real-time biomarker concentration.

Figure 5A:
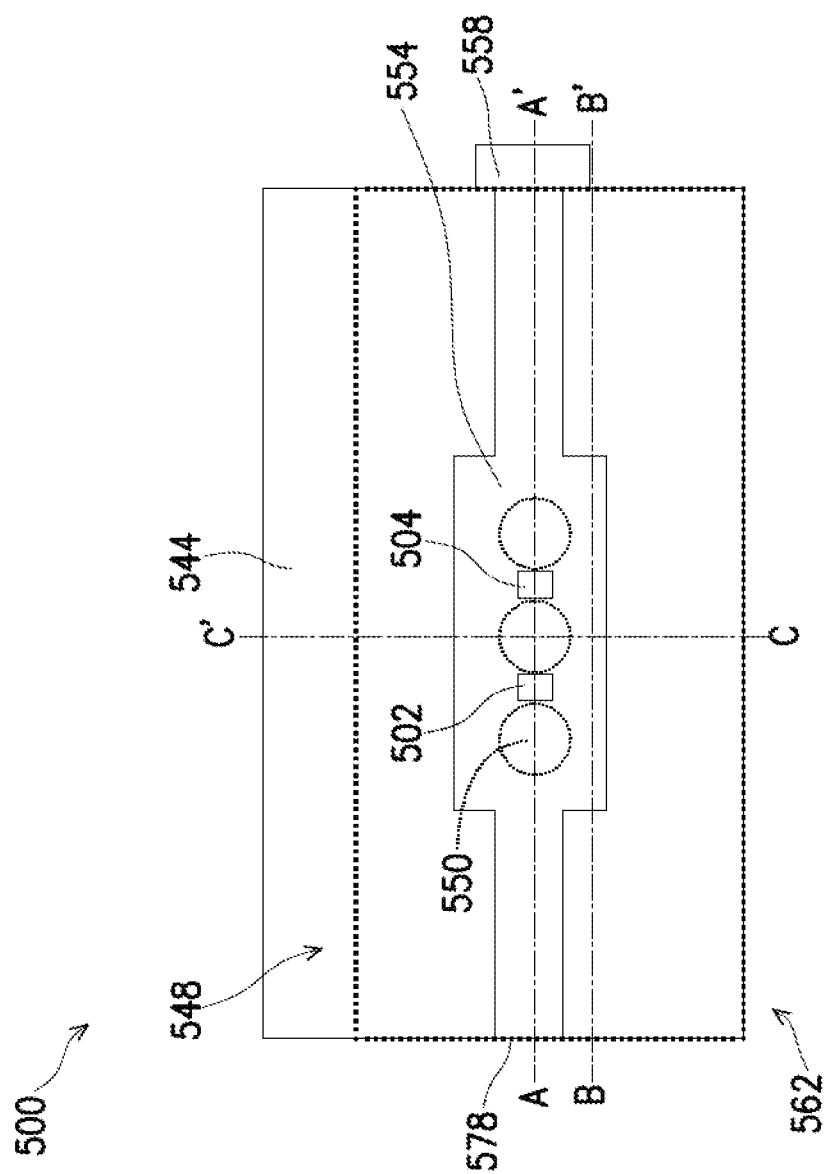
FIG. 5A is a top view of another integrated continuous biomarker monitoring and treatment chip in accordance with some embodiments.
Figure 5B:
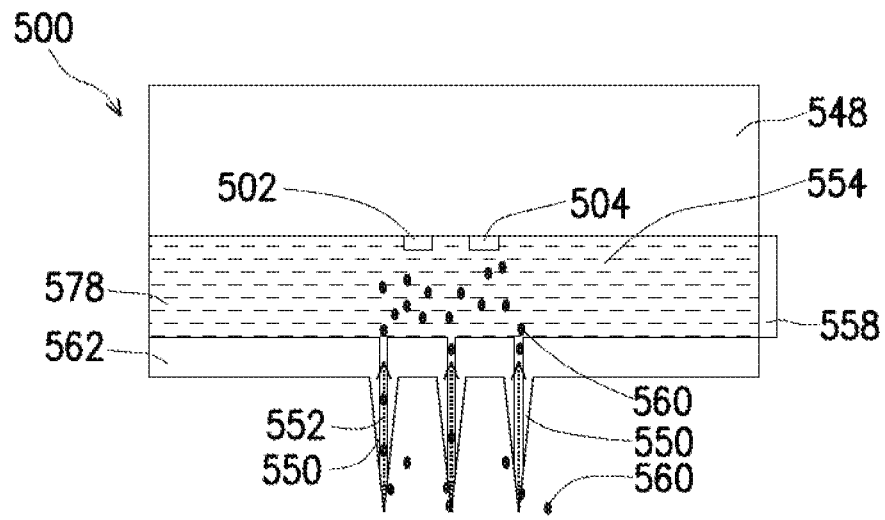
FIG. 5B is a cross-sectional diagram illustrating the cross section of the integrated continuous biomarker monitoring and treatment chip along a line A-A' of FIG. 5A in accordance with some embodiments.
Figure 5C:
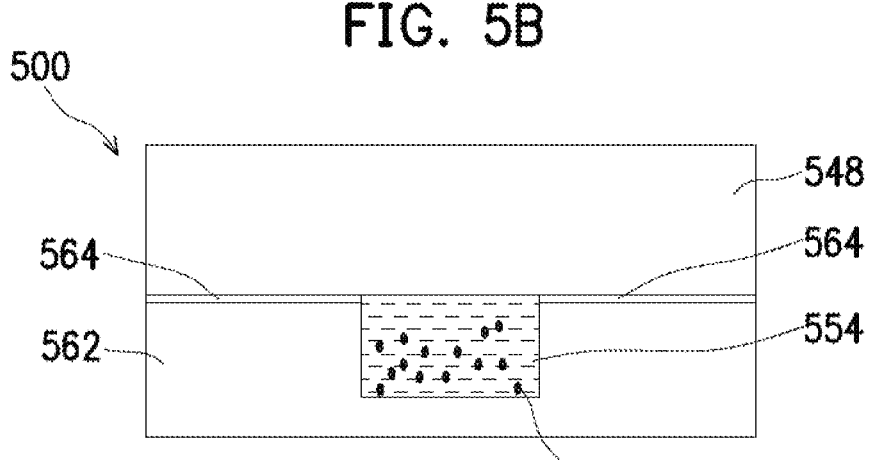
FIG. 5C is a cross-sectional diagram illustrating the cross section of the integrated continuous biomarker monitoring and treatment chip along a line B-B' of FIG. 5A in accordance with some embodiments.
Figure 5D:
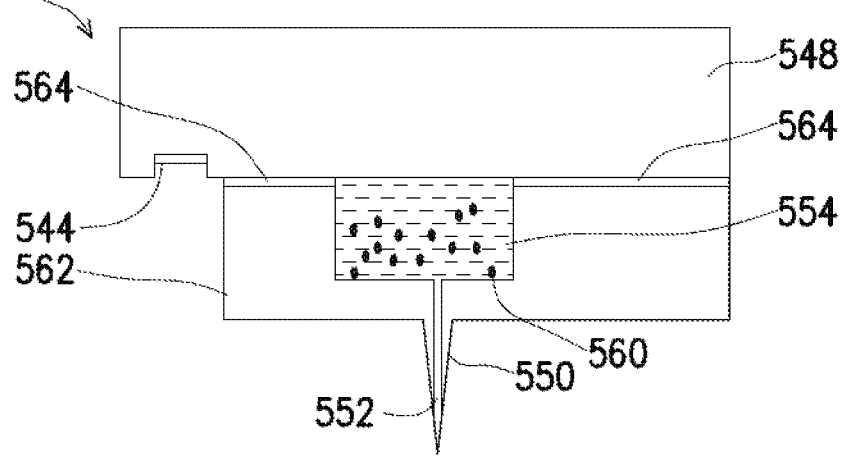
FIG. 5D is a cross-sectional diagram illustrating the cross section of the integrated continuous biomarker monitoring and treatment chip along a line C-C' of FIG. 5A in accordance with some embodiments.
Figure 5E:
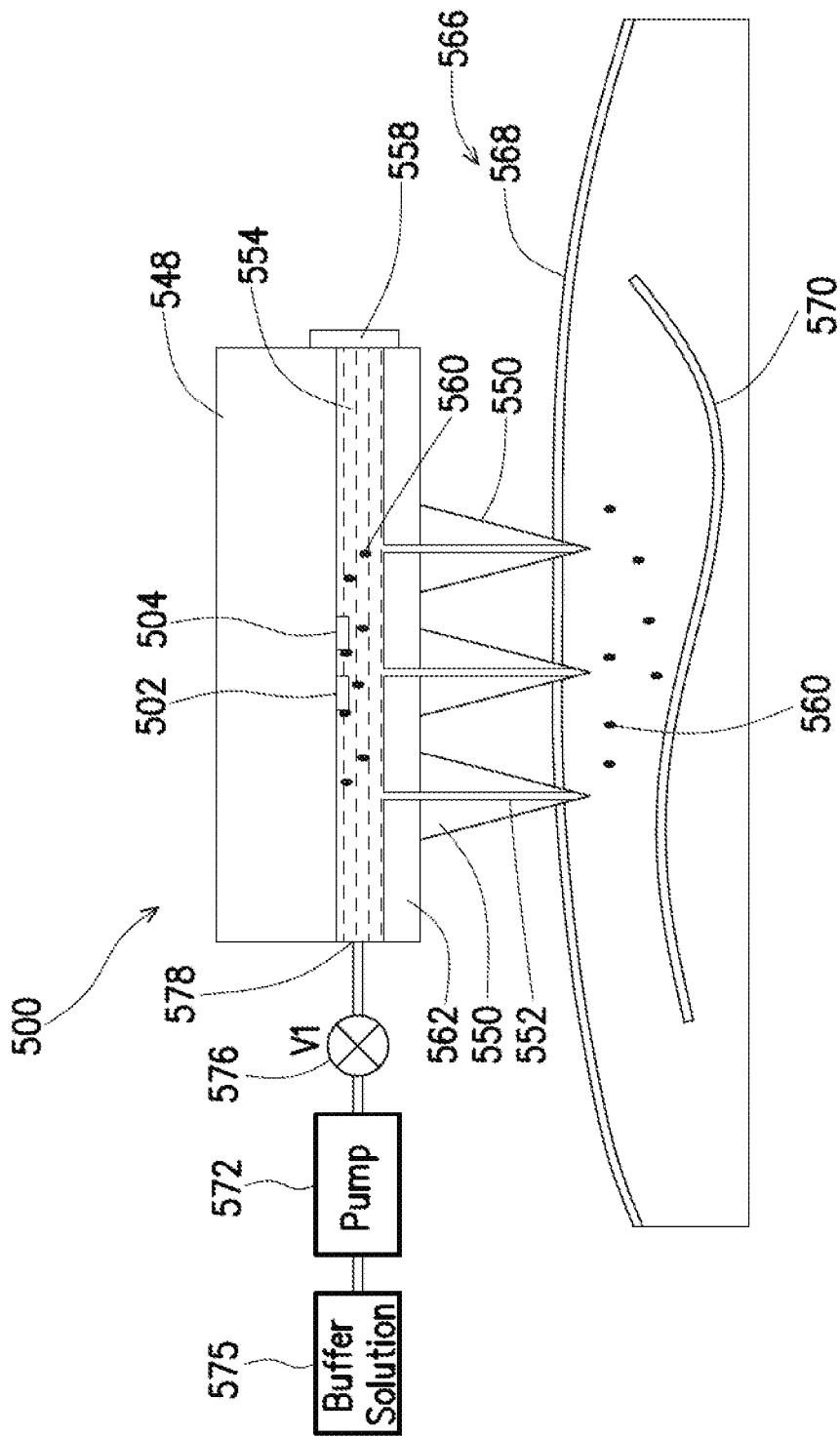
FIG. 5E is a diagram illustrating the use of the integrated continuous biomarker monitoring and treatment chip of FIG. 5A in accordance with some embodiments.
Figure 5F:
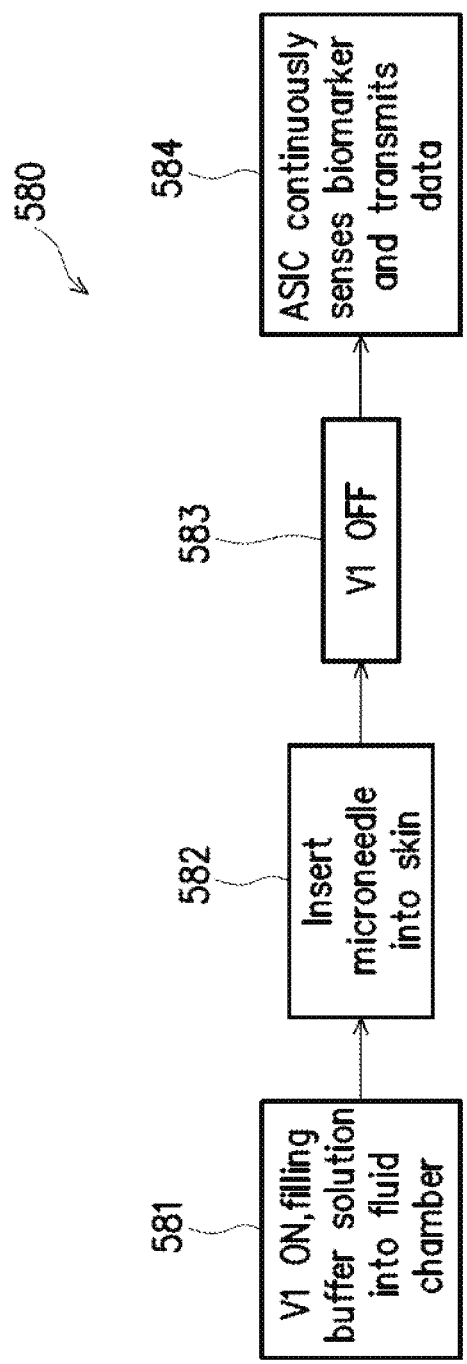
FIG. 5F is a flowchart illustrating a method for continuous biomarker monitoring in accordance with some embodiments.
Figure 5G:
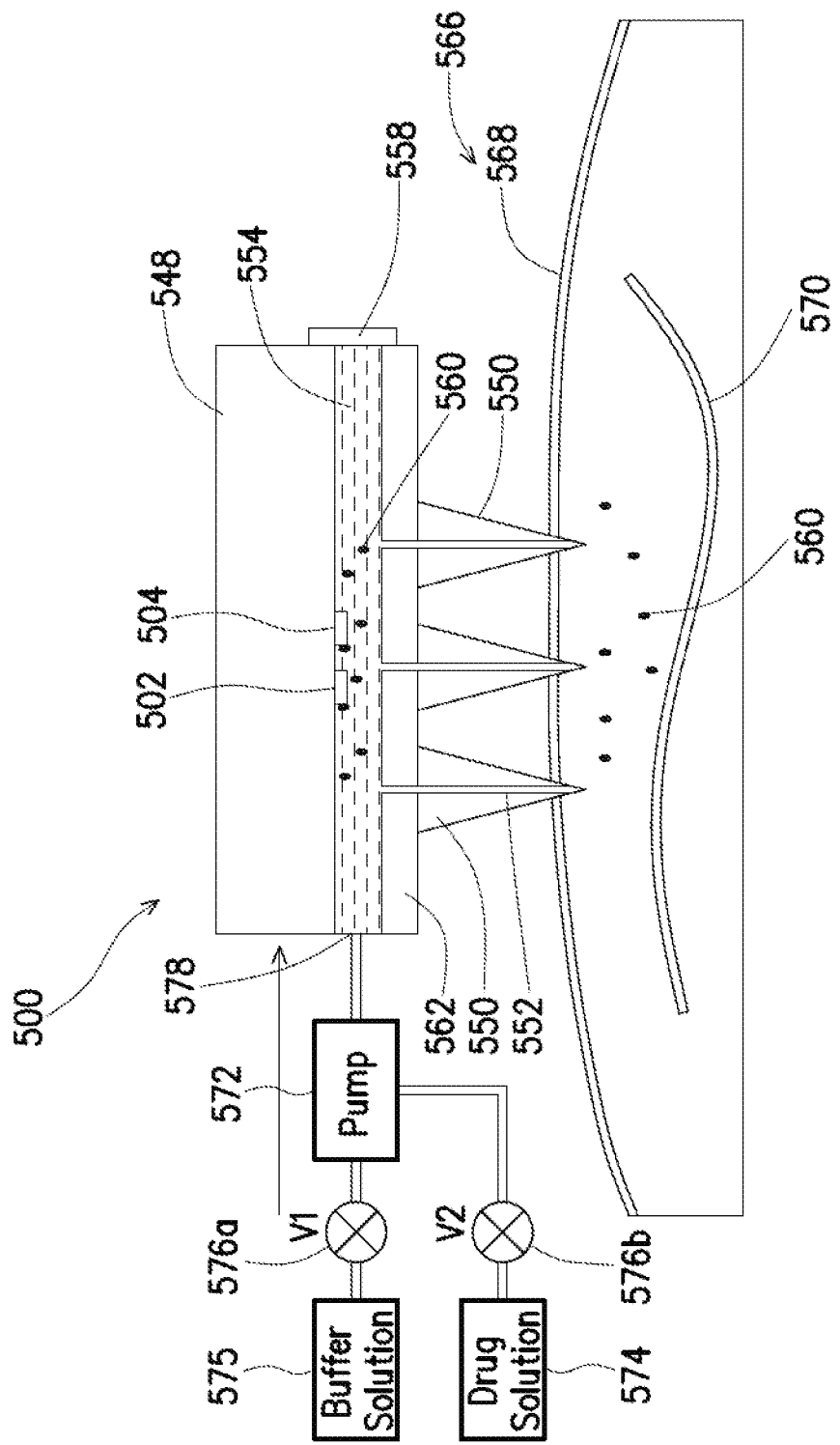
FIG. 5G is a diagram illustrating the use of the integrated continuous biomarker monitoring and treatment chip of FIG. 5A in accordance with some embodiments.
Figure 5H:
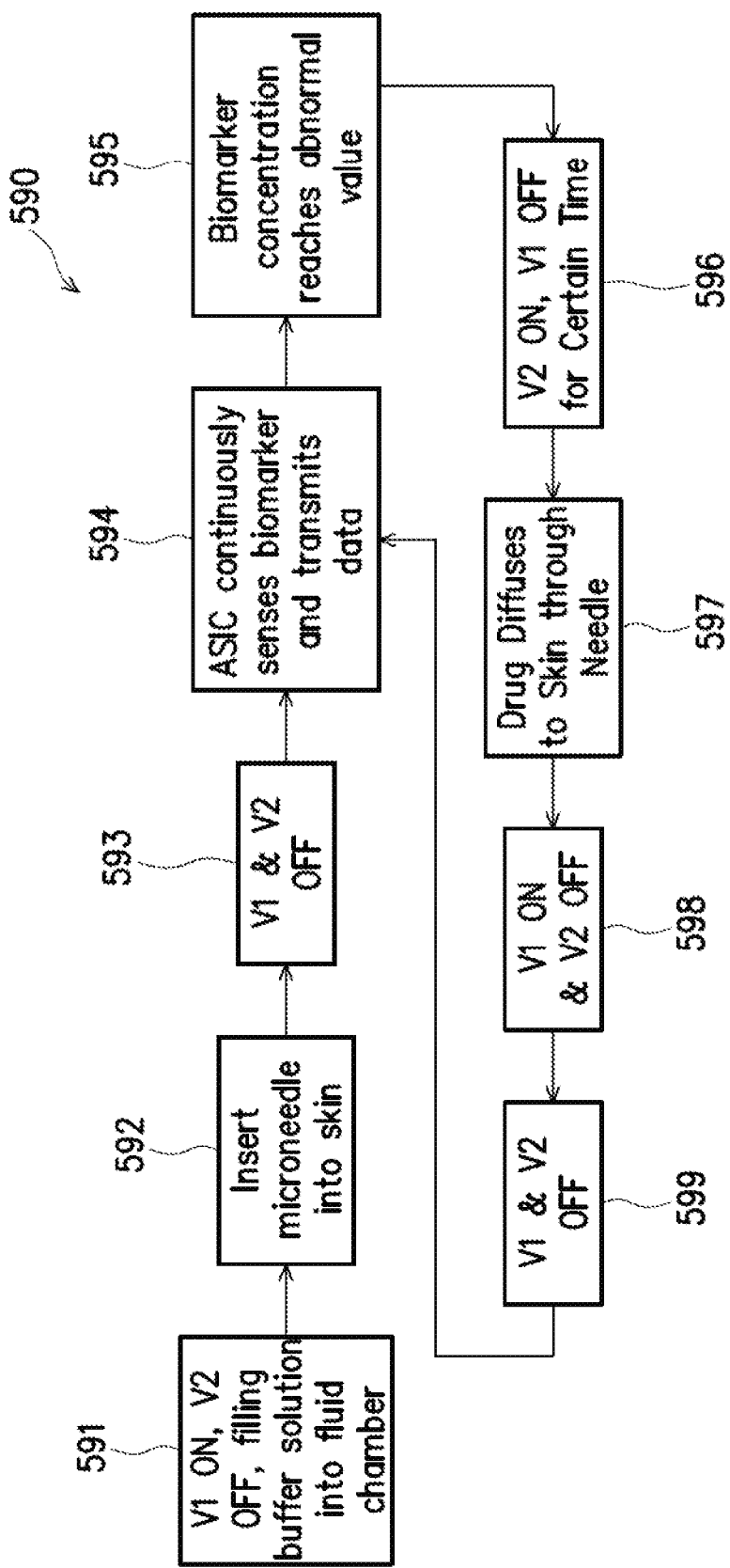
FIG. 5H is a flowchart illustrating a method for continuous biomarker monitoring with closed-loop drug releasing treatment in accordance with some embodiments.

FIG. 5A is a top view of another integrated continuous biomarker monitoring and treatment chip 500 in accordance with some embodiments. FIG. 5B is a cross-sectional diagram illustrating the cross section of the integrated continuous biomarker monitoring and treatment chip 500 along a line A-A' of FIG. 5A in accordance with some embodiments. FIG. 5C is a cross-sectional diagram illustrating the cross section of the integrated continuous biomarker monitoring and treatment chip 500 along a line B-B' of FIG. 5A in accordance with some embodiments. FIG. 5D is a cross-sectional diagram illustrating the cross section of the integrated continuous biomarker monitoring and treatment chip 500 along a line C-C' of FIG. 5A in accordance with some embodiments. FIG. 5E is a diagram illustrating the use of the integrated continuous biomarker monitoring and treatment chip 500 of FIG. 5A in accordance with some embodiments. FIG. 5F is a flowchart illustrating a method 580 for continuous biomarker monitoring in accordance with some embodiments. FIG. 5G is a diagram illustrating the use of the integrated continuous biomarker monitoring and treatment chip 500 of FIG. 5A in accordance with some embodiments. FIG. 5H is a flowchart illustrating a method 590 for continuous biomarker monitoring with closed-loop drug releasing treatment in accordance with some embodiments.

As shown in FIGS. 5A-5D, the integrated continuous biomarker monitoring and treatment chip 500 may include, among other things, a CMOS ASIC 548, a cap structure 562 attached to the back of the CMOS ASIC 548, an inlet 578, and a gas-liquid separation membrane 558. In the example shown in FIGS. 5A-5D, the cap structure 562 is attached to the CMOS ASIC 548 via wafer bonding structures 564, though other means of bonding may be employed. The example CMOS ASIC 548 has, among other things, a biosensor array 502 and a control sensor array 504 at the back of the CMOS ASIC 548. The example cap structure 562 has, among other things, a fluid chamber 554 and multiple microneedles 550. The fluid chamber 554 may accommodate fluid which may contain biomarker molecules (e.g., glucose molecules) 560. The biosensor array 502 and the control sensor array 504 may detect the existence and density of the biomarker molecules 560 as explained above. The fluid may enter the fluid chamber 554 via the inlet 578 and/or the multiple microneedles 550. The number of microneedles 550 may vary as needed. For each microneedle 550, there is a (silicon) microneedle channel 552 that connects the fluid chamber 554 with outside. The gas-liquid separation membrane 558 is configured to eliminate air bubbles in the fluid chamber 554 since only gas can pass the gas-liquid separation membrane 558.

Referring to FIGS. 5E and 5F, the integrated continuous biomarker monitoring and treatment chip 500 is used for continuous biomarker monitoring. As shown in FIG. 5E, the fluid chamber 554 is connected to buffer solution 575 through a fluidics valve 576 and a pump 572. A buffer solution is an aqueous solution consisting of a mixture of a weak acid and its conjugate base, or vice versa. In one example, the buffer solution 575 is 1×PBS (1× Physiological Saline Solution) or PBS with lower concentrations such as 0.1×PBS or 0.01×PBS. In another example, the buffer solution 575 is HEPES [(4-(2-hydroxyethyl)-1-piperazineethanesulfonic acid)]. In yet another example, the buffer solution 575 is TRIS [tris(hydroxymethyl) aminomethane]. At step 581, the fluidics valve 576 is turned on and the buffer solution 575 is filled in the fluid chamber 554. At step 582, the microneedles 550 are inserted into a skin 568. Specifically, the microneedles 550 penetrate the skin 568 of a body (e.g., human body) 566. Biomarker molecules (e.g., glucose molecules) 560 may exist in the body 566 (beneath the skin 568, inside and around the blood vessel 570). Interstitial fluid may naturally flow into the fluid chamber 554 via the microneedle channels 552 of the microneedles 550 due to pressure. As a result, the biomarker molecules 560 enter the fluid chamber 554 as well. At step 583, the fluidics valve 576 is turned off. At step 584, the CMOS ASIC 548 with the biosensor array 502 and the control sensor array 504 continuously senses the biomarker molecules 560 and transmits data. Specifically, the biosensor array 502, along with the control sensor array 504, may detect the existence and density of the biomarker molecules 560. The detected signal is further processed (e.g., amplified, converted, etc.) by the CMOS ASIC 548. The result data may be transmitted via either the bonding pads 544 shown in FIG. 5A or alternatively the wireless transceiver module 140 shown in FIG. 1A. As such, the integrated continuous biomarker monitoring and treatment chip 500 may continuously sense the biomarker molecules 560, which in turn may be used for diagnose or treatment of certain diseases (e.g., diabetes) related to the biomarker molecules 560.

On the other hand, referring to FIGS. 5G and 5H, the integrated continuous biomarker monitoring and treatment chip 500 is used for continuous biomarker monitoring with closed-loop drug releasing treatment. As shown in FIG. 5G, the fluid chamber 554 is connected to a pump 572 via the inlet 578, which is further connected to both buffer solution 575 and drug solution 574 through a fluidics valve 576a ("V1") and another fluidics valve 576b ("V2"), respectively. At step 591, the fluidics valve 576a is turned on and the fluidics valve 576b is turned off. As a result, the buffer solution 575 is filled into the fluid chamber 554. At step 592, the microneedles 550 are inserted into a skin 568. Specifically, the microneedles 550 penetrate the skin 568 of a body (e.g., human body) 566. Biomarker molecules (e.g., glucose molecules) 560 may exist in the body 566 (beneath the skin 568, inside and around the blood vessel 570). Interstitial fluid may naturally flow into the fluid chamber 554 via the microneedle channels 552 of the microneedles 550 due to pressure. As a result, the biomarker molecules 560 enter the fluid chamber 554 as well. At step 593, both the fluidics valve 576a and the fluidics valve 576b are turned off. At step 594, the CMOS ASIC 548 with the biosensor array 502 and the control sensor array 504 continuously senses the biomarker molecules 560 and transmits data. Specifically, the biosensor array 502, along with the control sensor array 504, may detect the existence and density of the biomarker molecules 560. The detected signal is further processed (e.g., amplified, converted, etc.) by the CMOS ASIC 548. The result data may be transmitted via either the bonding pads 544 shown in FIG. 5A or alternatively the wireless transceiver module 140 shown in FIG. 1A. At step 595, the CMOS ASIC 548 determines that the biomarker concentration reaches an abnormal value (e.g., above a threshold concentration). Then at step 596, the fluidics valve 576b is turned on and the fluidics valve 576a keeps off for a certain period of time. As a result, at step 597, the drug solution 574 flows into the drug channel fluid chamber 554 (e.g., pumped by the pump 572) and subsequently flows into the skin/body through the microneedles 550. As such, the drug solution 474 is delivered and the drug releasing treatment begins. On the other hand, the CMOS ASIC 448 still continuously senses the biomarker molecules and transmits data as at step 594. Due to the drug releasing treatment, the biomarker concentration becomes lower over time. After the certain period of time, at step 598, the fluidics valve 576b is turned off while the fluidics valve 576a is turned on. As a result, the buffer solution 575 can flow into the fluid chamber 554. Then at step 599, both the fluidics valve 576a and the fluidics valve 576b are turned off. The method 590 then loops back to step 594. Accordingly, the method 590 can achieve simultaneous biomarker monitoring with closed-loop drug releasing treatment. In other words, the biomarker concentration is being constantly monitored and the drug releasing treatment is triggered automatically based on the real-time biomarker concentration. The buffer solution 575 is added to the fluid chamber 554 every time the drug solution 574 is delivered.

As mentioned above, the biosensor system package 200a of FIG. 2A and the biosensor system package 200b of FIG. 2B are fabricated by the method 600 of FIGS. 6A-6B.

The method 600 begins at step 602 where a substrate is provided. The substrate may be a semiconductor substrate (e.g., wafer). The semiconductor substrate may be a silicon substrate. Alternatively, the substrate may comprise another elementary semiconductor, such as germanium; a compound semiconductor including silicon carbide, gallium arsenic, gallium phosphide, indium phosphide, indium arsenide, and/or indium antimonide; an alloy semiconductor including SiGe, GaAsP, AlInAs, AlGaAs, GaInAs, GaInP, and/or GaInAsP; or combinations thereof. In embodiments shown in FIGS. 6A-6E and FIGS. 7-38, the substrate is a semiconductor on insulator (SOI) substrate 202. The SOI substrate 202 shown in FIG. 7 includes a bulk silicon layer 204, a buried oxide (BOX) layer 206, and a semiconductor layer 208 (i.e., an active layer 208). The buried oxide layer 206 may be formed by a process such as separation by implanted oxygen (SIMOX), and/or other suitable processes. The semiconductor layer 208 may include doped regions, such as p-wells and n-wells.

The method then proceeds to step 604 where a transistor structure and a temperature sensor are formed on the substrate. The transistor structure (i.e., the FET) may include a gate structure, a source region, a drain region, and a channel region interposing the source and drain regions. It should be noted that in some embodiments, the transistor structure (i.e., the FET) may be an array of transistor structures. For simplicity, only one transistor structure is used as an example in the description below. As shown in the example in FIG. 7, the source, drain, and/or channel region of the FET 210 may be formed on an active region in the semiconductor layer 208. The FET 210 may be an n-type FET (nFET) or a p-type FET (pFET). For example, the source/drain regions may comprise n-type dopants or p-type dopants depending on the FET configuration. The gate structure may include a gate dielectric layer, a gate electrode layer, and/or other suitable layers. In an embodiment, the gate electrode is polysilicon. Other exemplary gate electrodes include metal gate electrodes including material such as, Cu, W, Ti, Ta, Cr, Pt, Ag, Au; suitable metallic compounds like TiN, TaN, NiSi, CoSi; combinations thereof; and/or other suitable conductive materials. In an embodiment, the gate dielectric is silicon oxide. Other exemplary gate dielectrics include silicon nitride, silicon oxynitride, a dielectric with a high dielectric constant (high-k), and/or combinations thereof. Examples of high-k materials include hafnium silicate, hafnium oxide, zirconium oxide, aluminum oxide, tantalum pentoxide, hafnium dioxide-alumina ($HfO_2$—$Al_2O_3$) alloy, or combinations thereof. The FET 210 may be formed using typical CMOS processes such as, photolithography; ion implantation; diffusion; deposition including physical vapor deposition (PVD), metal evaporation or sputtering, chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), atomic layer deposition (ALD), spin on coating; etching including wet etching, dry etching, and plasma etching; and/or other suitable CMOS processes.

The temperature sensor may detect the temperature of the chamber 244 in FIGS. 2A and 2B. As shown in the example in FIG. 7, the temperature sensor 211 is formed in the semiconductor layer 208. In some embodiments, the temperature sensor 211 may include a thermal coupling element (e.g., a platinum thermocouple).

The method 600 then proceeds to step 606 where a multi-layer interconnect (MLI) structure is formed above the transistor structure. The MLI structure may include conductive lines, conductive vertical interconnect accesses (vias), and/or interposing dielectric layers (e.g., interlayer dielectric (ILD) layers). The MLI structure may provide physical and electrical connection to the transistor (i.e., the FET), described above with reference to step 604. The conductive lines may comprise copper, aluminum, tungsten, tantalum, titanium, nickel, cobalt, metal silicide, metal nitride, poly silicon, combinations thereof, and/or other materials possibly including one or more layers or linings. The interposing dielectric layers (e.g., ILD layers) may comprise silicon dioxide, fluorinated silicon glass (FGS), SILK (a product of Dow Chemical of Michigan), BLACK DIAMOND (a product of Applied Materials of Santa Clara, Calif.), and/or other suitable insulating materials. The MLI structure may be formed by suitable processes typical in CMOS fabrication such as CVD, PVD, ALD, plating, spin-on coating, and/or other processes.

Figure 7:
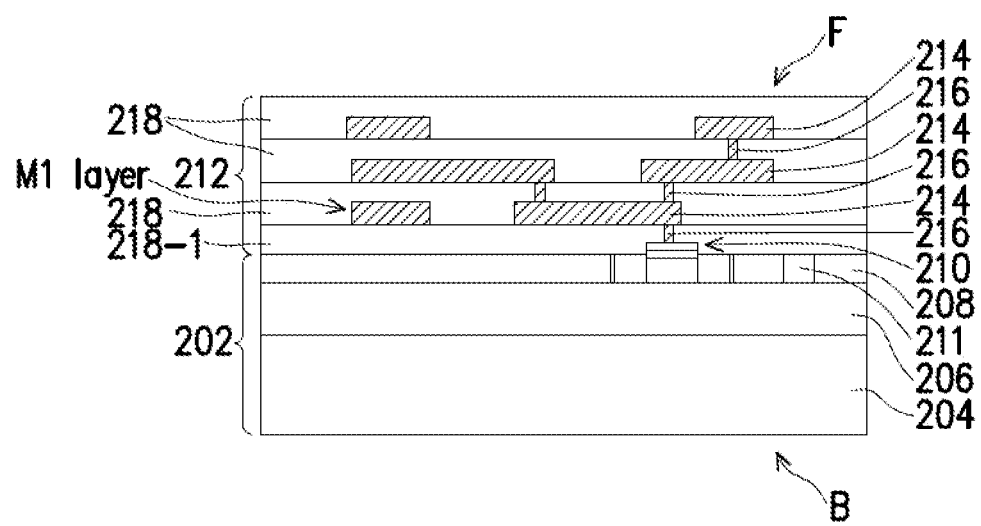
FIGS. 7-38 are cross-sectional diagrams illustrating the biosensor system package constructed according to one or more steps of the method of FIG. 6A and FIG. 6B in accordance with some embodiments.
Figure 8:
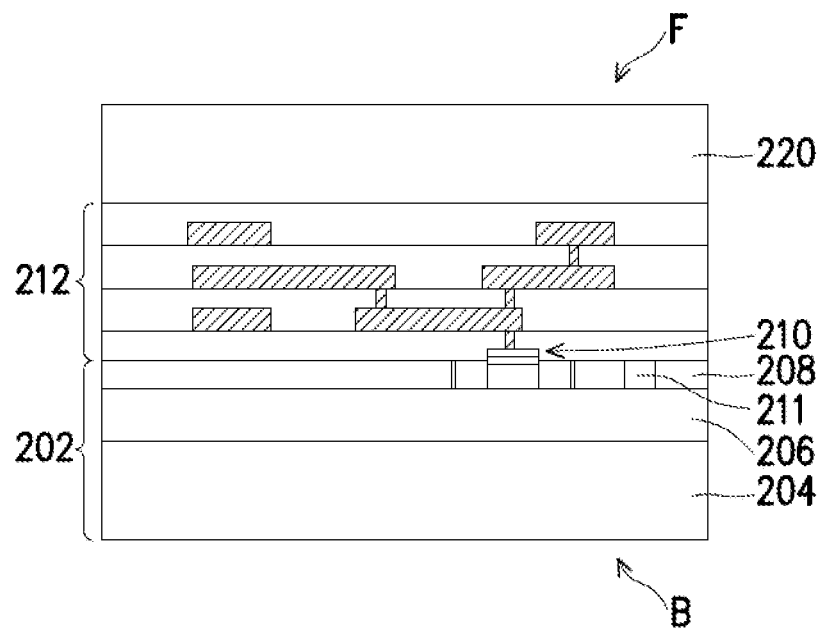

As shown in the example in FIG. 7, an MLI structure 212 is disposed on the substrate 202 and above the FET 210 and the temperature sensor 211. The MLI structure 212 includes a plurality of conductive lines 214 connected by conductive vias or plugs 216. In one embodiment, the conductive lines 214 include aluminum and/or copper. In one embodiment, the vias or plugs 216 include tungsten. In another embodiment, the vias or plugs 216 include copper. In one embodiment, the interposing dielectric layers 218 are disposed on the substrate 202 including interposing the conductive features of the MLI structure 212. The interposing dielectric layers 218 may be ILD layers. In another embodiment, the dielectric layer 218 is a single ILD layer. In one embodiment, each of the interposing dielectric layer 218 includes silicon oxide. The MLI structure 212 may provide electrical connection to the gate and/or the source/drain of the FET 210. As shown in the example in FIG. 7, the MLI structure 212 is at the front side (F) while the substrate 202 is at the back side (B).

Additionally, conductive line(s) in the first metal layer ("M1 layer") may be used as the heater 142 as shown in FIG. 1A. In other words, conductive line(s) can be an embedded (electric-resistive) heater used to generate heat. In some embodiments, the heater may have multiple zones that are individually controllable, and/or is made of materials such as Al, Cu, TiAlN, though other material may also be employed. Alternatively, the heater maybe arranged under a semiconductor substrate and made of silicon or polysilicon. By using an embedded heater, temperature control and uniformity may be improved.

The method 600 then proceeds to step 608 where a carrier substrate is attached to the front side (F). In other words, the carrier substrate is attached to the MLI structure. The carrier substrate may protect the front side (F) during subsequent steps. In one embodiment, the carrier substrate is bonded to the MLI structure. In another embodiment, the carrier substrate is bonded to a passivation layer formed on the MLI structure. The carrier substrate may be attached using fusion, diffusion, eutectic, and/or other suitable bonding methods. Exemplary compositions for the carrier substrate include silicon, glass, and quartz. It should be noted that other compositions are possible and within the scope of the present disclosure. As shown in the example in FIG. 8, a carrier substrate 220 is attached to the MLI structure 212. In some embodiments, the carrier substrate 220 may include functionalities such as, interconnect features, wafer bonding sites, defined cavities, and/or other suitable features.

Figure 9:
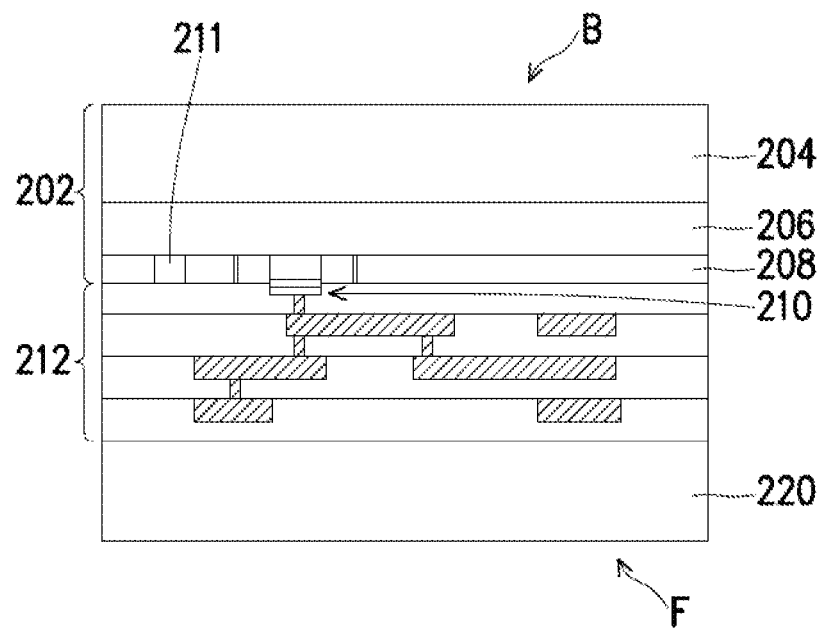
Figure 10:
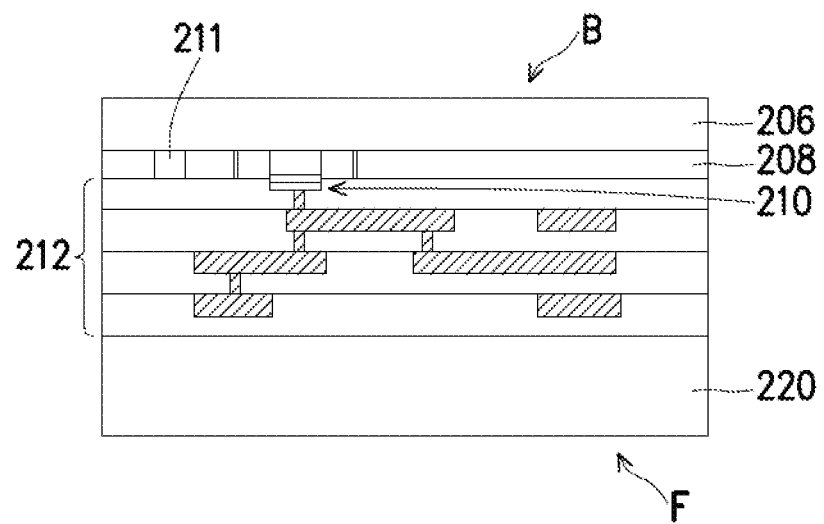

The method 600 then proceeds to step 610 where the wafer is flipped. As shown in FIG. 9, the back side (B) is on the top. In other words, the bulk silicon layer 204 is on the top. The method 600 then proceeds to step 612 where the bulk silicon layer 204 is removed. The removal may be accomplished by mechanical or chemical means. For example, a mechanical means includes polishing or grinding, such as chemical mechanical polishing (CMP). A chemical means includes wet etch, such as HF/nitric/acetic acid (HNA) or tetramethylammonium hydroxide (TMAH) or dry etch including plasma and non-plasma etch. As shown in the example in FIG. 10, the bulk silicon layer 204 in FIG. 9 is removed. The buried oxide layer 206 is on the top at the back side (B).

The method 600 then proceeds to step 614 where the buried oxide layer is patterned to form an opening at the back side (B). A photoresist pattern is formed on the buried oxide layer. In some embodiments, the photoresist pattern protects some of the buried oxide layer from a subsequent non-plasma etch to expose the backside (B) of the biosensor system package. Specifically, the photoresist pattern protects some of the buried oxide layer from the subsequent non-plasma etch to expose the active region of the transistor structure formed at step 604. The non-plasma etch may be a wet etch or a dry etch that does not involve plasma. In some embodiments, a two-step etch process may be employed to form the opening at the back side (B). The first etching step contains plasma and the second etching step is a non-plasma etch. As shown in the example in FIG. 11, the non-plasma etch forms a trench 222 having a bottom exposing the channel region of the FET 210. A non-plasma etch is used to avoid plasma-induced damage (PID) at the exposed surface of the channel region 219. In a non-limiting example, the height of the trench 222 may range between 0.3 µm to 1 µm, while the width of the trench 222 may range between 0.5 µm to 200 µm (in some extreme cases). In some embodiments, the sidewall profile of the trench 222 is substantially straight. After the non-plasma etch, the photoresist pattern is removed. A PID-less photoresist removal process such as stripping and ozone ashing may be used. Because the exposed surface of the trench 222 and the exposed surface of the channel region of the FET 210 are susceptible to plasma-induced damage (PID), some plasma ashing processes may not be used to remove the photoresist pattern.

The method 600 then proceeds to step 616. At step 616, an interface layer is deposited. In one embodiment, the interface layer is a high-k material layer. The interface layer is compatible (e.g., friendly) for biomolecules or bio-entities binding. For example, the interface layer may include a capture reagent layer, which is a layer of capture reagent capable of binding a target analyte in the fluid samples. In some embodiments, the interface layer includes a plurality of layers. For instance, the interface layer may include a dielectric material (e.g., a high-k material), a conductive material, and/or other suitable material for holding a receptor. Exemplary interface materials include high-k dielectric films, metals, metal oxides, dielectrics, and/or other suitable materials. As a further example, exemplary interface layer materials include $HfO_2$, $Ta_2O_5$, Pt, Au, W, Ti, Al, Cu, oxides of such metals, $SiO_2$, $Si_3N_4$, $Al_2O_3$, $TiO_2$, TiN, $ZrO_2$, SnO, $SnO_2$; and/or other suitable materials. The interface layer may be formed using CMOS processes such as, for example, physical vapor deposition (PVD) (sputtering), chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), or atomic layer CVD (ALCVD). A photoresist pattern is formed over the interface layer to protect a portion of the interface layer. The portion over the channel region of the FET is protected. Unprotected portions of the interface layer are removed in a subsequent etch process. The etch process may involve any known etch process including plasma etch, since the portion susceptible to PID is protected. The interface layer completely covers the channel region and may partially cover the source region and drain region. The partial coverage of the source and drain region may be adjusted based on the FET design and area requirements for the interface layer. In some embodiments, the interface layer may not be patterned and etched and remains over the respective surfaces of the FET.

Figure 11:
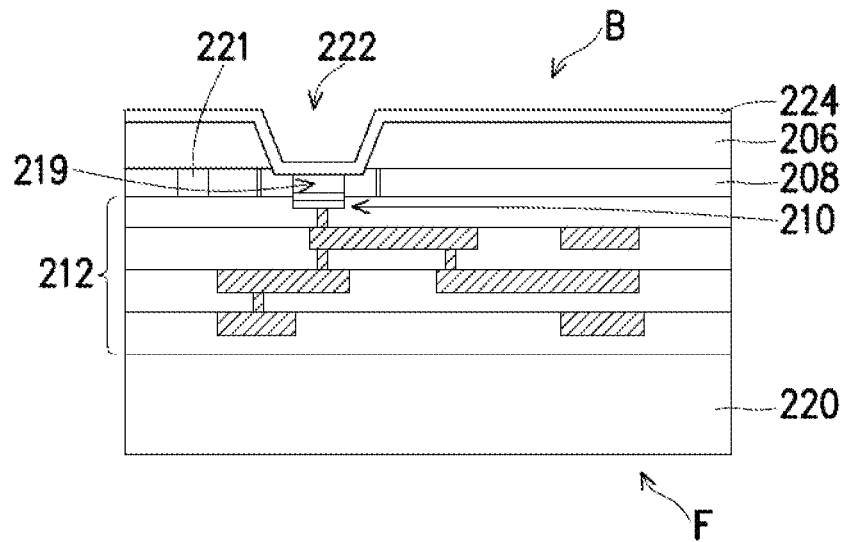

As shown in the example in FIG. 11, an interface layer 224 (e.g., a high-k material layer) is formed on the exposed surface of the trench 222 and the exposed surface of the active region 219 of the FET 210. Additionally, the interface layer 224 is deposited over the entire surface of the buried oxide layer 206.

Alternatively at step 618, an interface layer is deposited while some bonding sites are exposed. The boding sites are used for bonding a microfluidic channel cap structure to the back side (B), which will be described in detail below at step 626. It should be noted that whether bonding sites are required depends on specific bonding requirements. Similar to step 616, the interface layer may be formed using CMOS processes such as, for example, PVD (sputtering), CVD, PECVD, APCVD, LPCVD, HDPCVD, or ALCVD. A photoresist pattern is formed over the interface layer to protect a portion of the interface layer, and the bonding sites are not protected. Unprotected portions of the interface layer are removed in a subsequent etch process. The etch process may involve any known etch process including plasma etch, since the portion susceptible to PID is protected. After etching and optionally adding a passivating or blocking agent, the photoresist is removed in a PID-free photoresist removal process.

Figure 12:
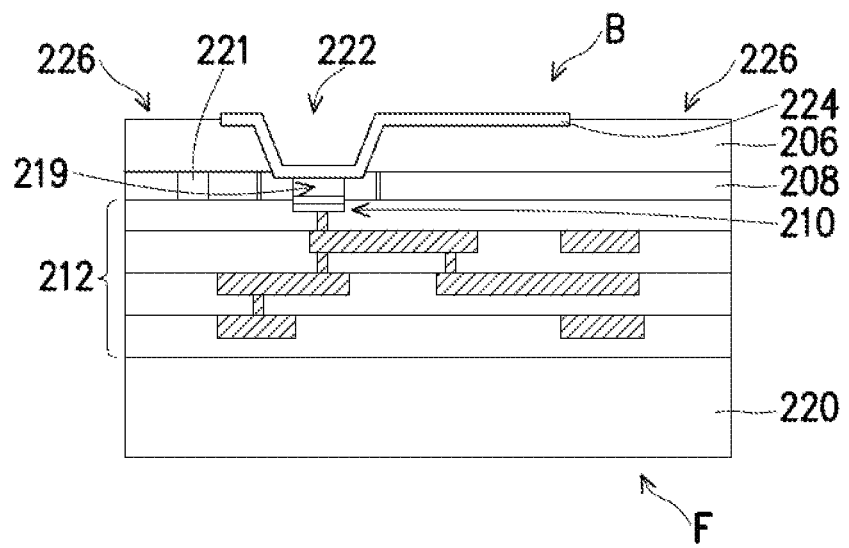

As shown in the example in FIG. 12, the interface layer 224 (e.g., a high-k material layer) is formed on the exposed surface of the trench 222 and the exposed surface of the active region 219 of the FET 210, while two bonding sites 226 are exposed. In other words, the buried oxide layer 206, except for the two bonding sites 226, are covered by the interface layer 224. It should be noted that the shape of the bonding sites may vary depending on the shape of the microfluidic channel cap structure.

Figure 13:
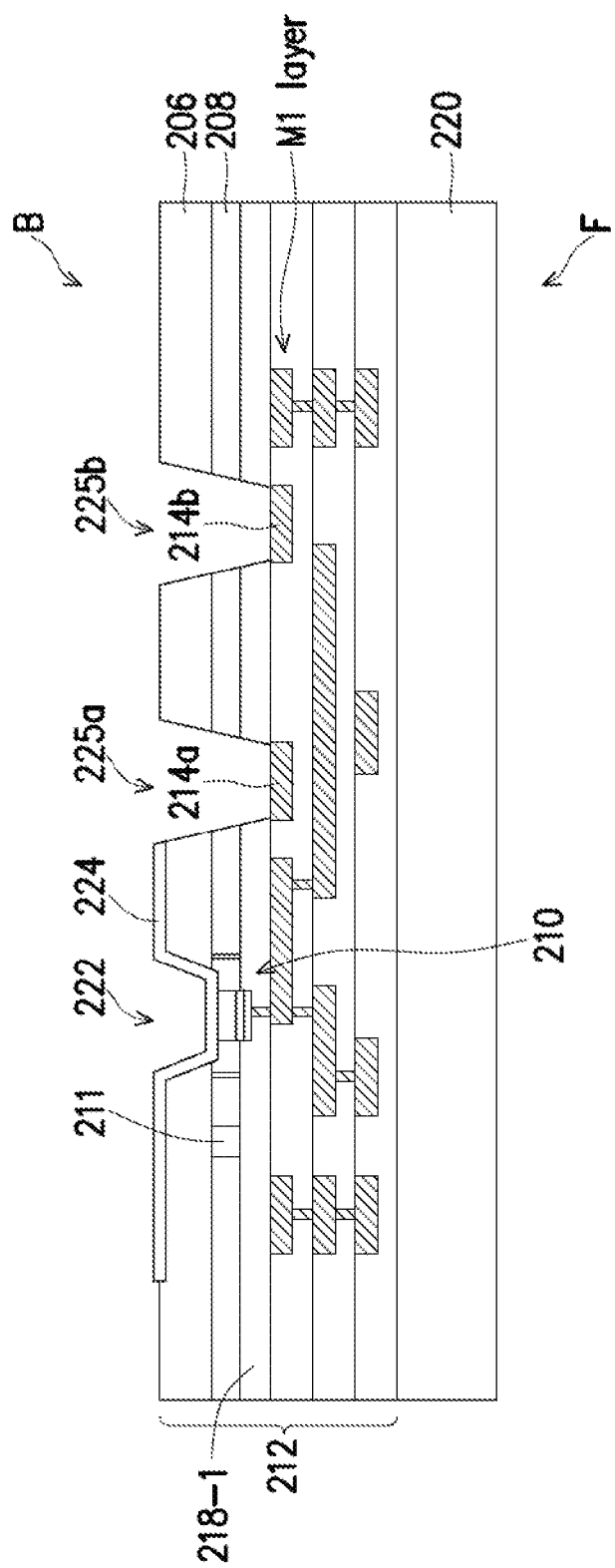

The method 600 then proceeds to step 620. At step 620, the buried oxide layer, the semiconductor layer, and the first interposing dielectric layer are patterned and etched to form opening(s) at the back side (B) to expose conductive line(s) at the first metal layer ("M1 layer"). A photoresist pattern is formed on the buried oxide layer and the interface layer deposited at step 616 or 618. Similar to step 614, the photoresist pattern protects the interface layer and some of the buried oxide layer from a subsequent etch to expose the backside (B) of the biosensor system package in some embodiments. As shown in the example in FIG. 13, two openings 225a and 225b (collectively 225) are formed at the back side (B). The number of openings 225 may vary as needed. In the example shown in FIG. 13, the opening 225a is used for depositing a reference electrode while the opening 225b is used for subsequent wire bonding. In another example, there is only one opening 225 used for depositing a reference electrode. In other words, no opening 225 is formed for wire bonding. As shown in FIG. 13, the openings 225a and 225b are formed in the buried oxide layer 206, the semiconductor layer 208, and the first interposing dielectric layer 218-1, and have bottoms exposing the conductive lines 214a and 214b, respectively, at the M1 layer. In some embodiments, the sidewall profile of the trench 222 is substantially straight. After the etch process, the photoresist pattern is removed.

Figure 14:
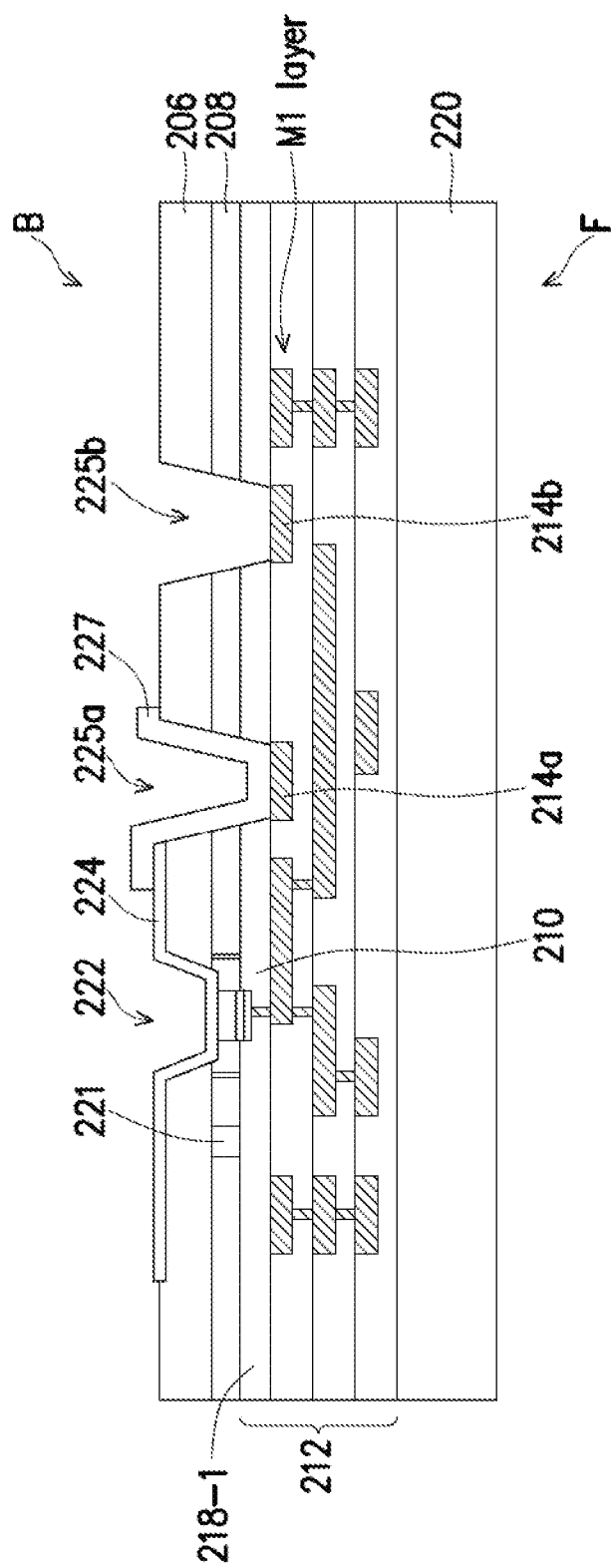
Figure 15:
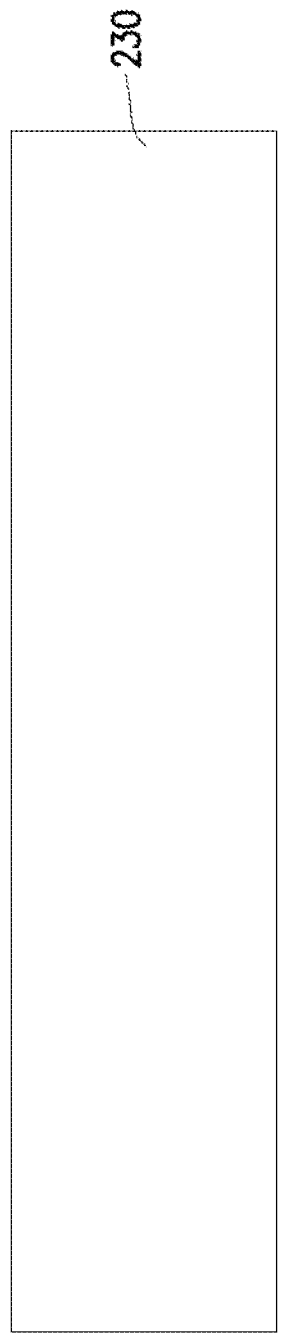
Figure 16:
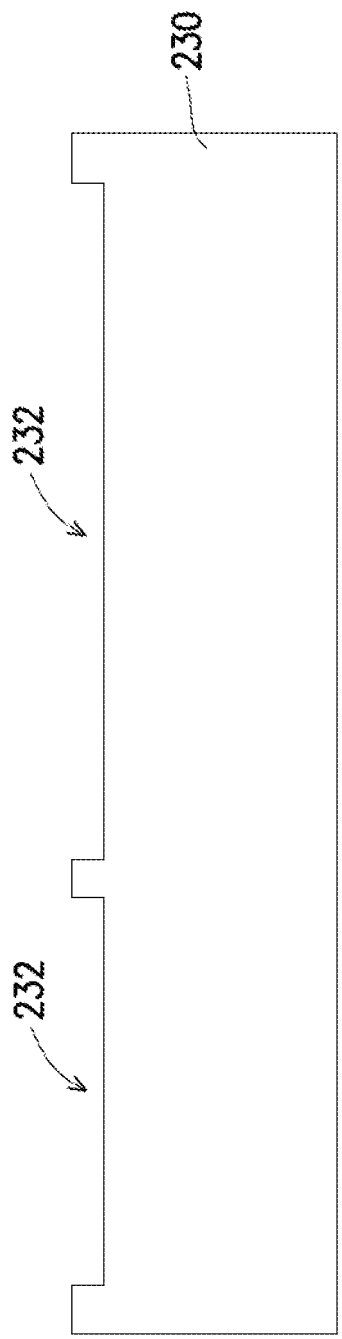
Figure 17:
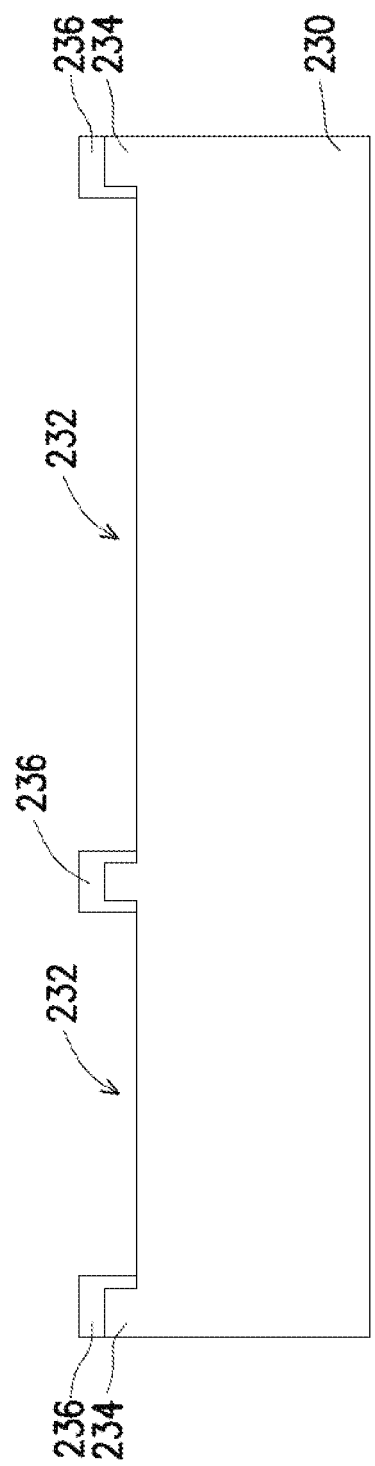
Figure 18:
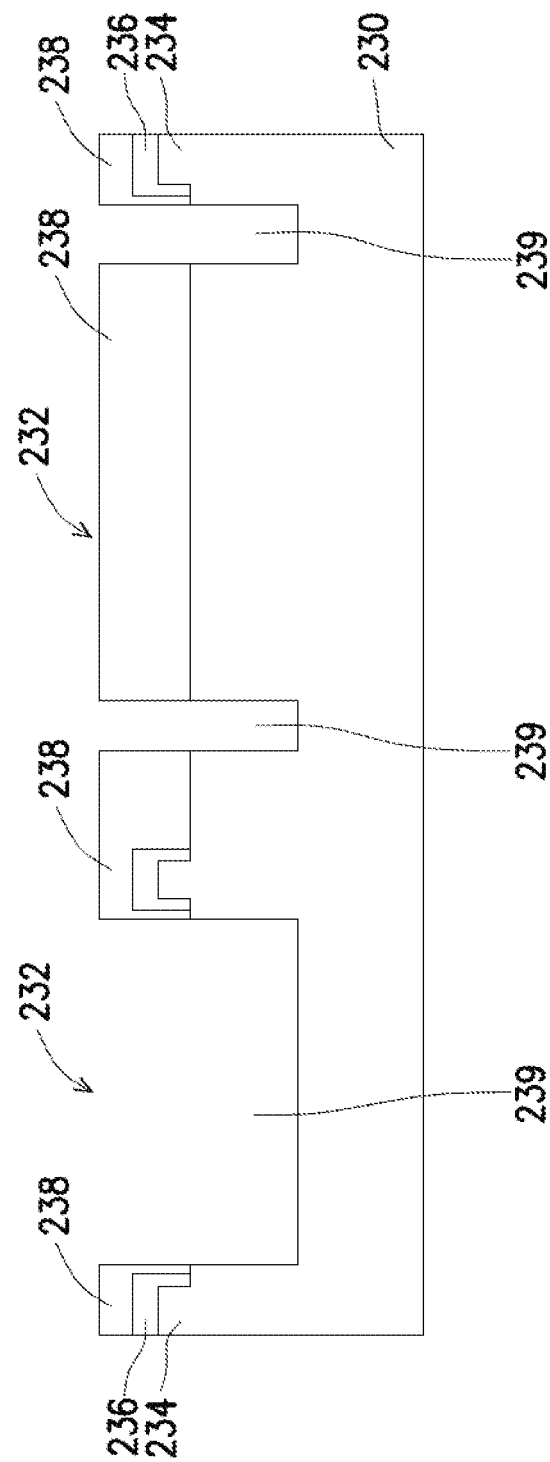
Figure 19:
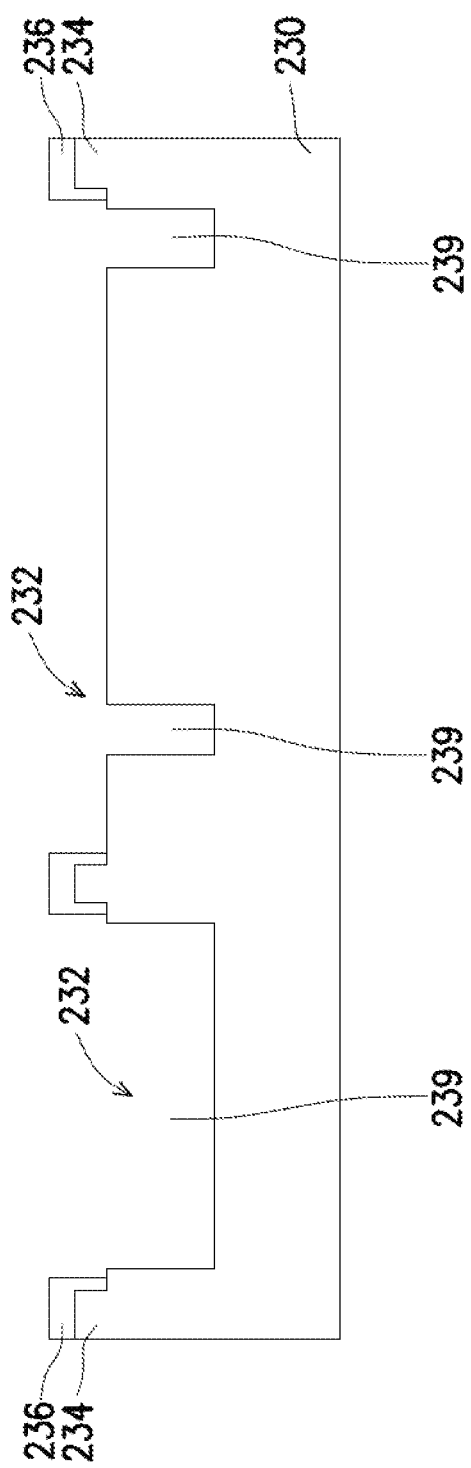
Figure 20:
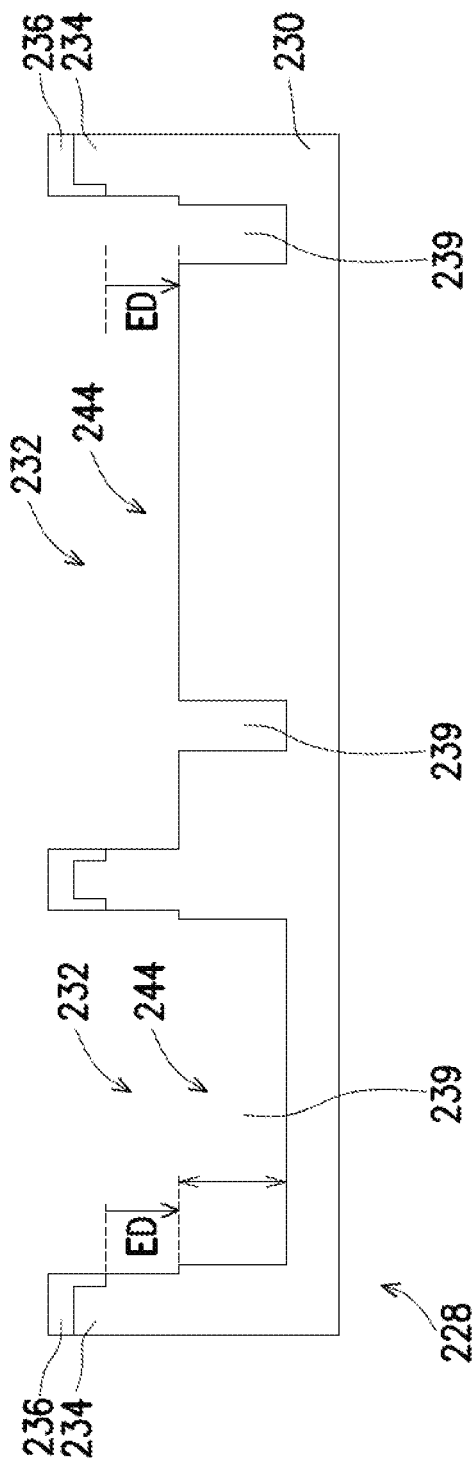
Figure 21:
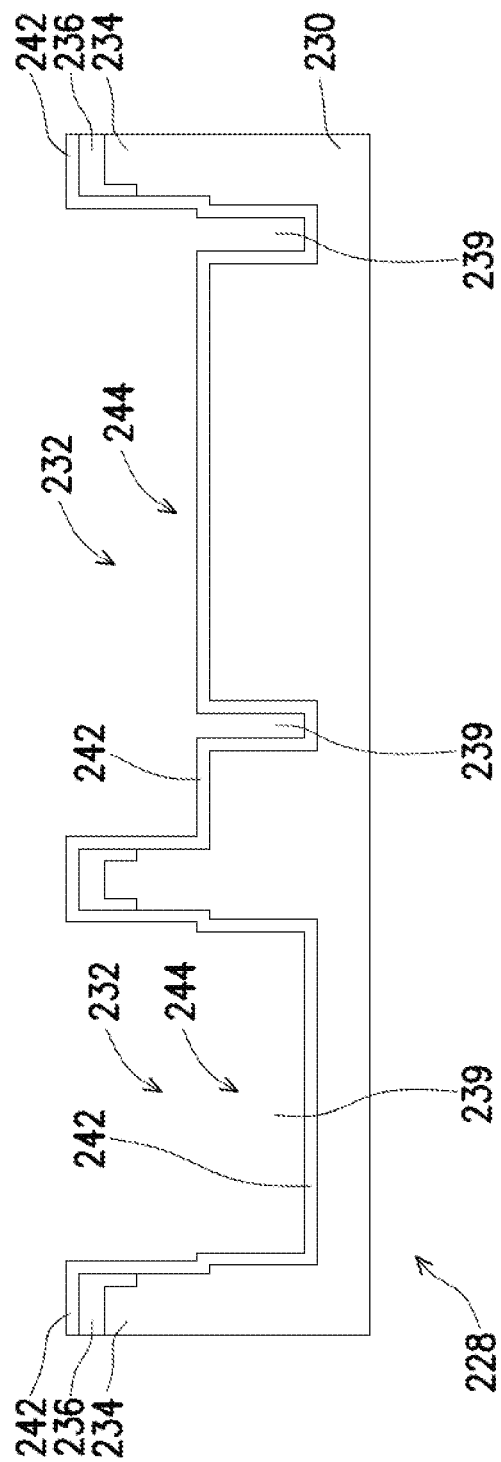
Figure 22:
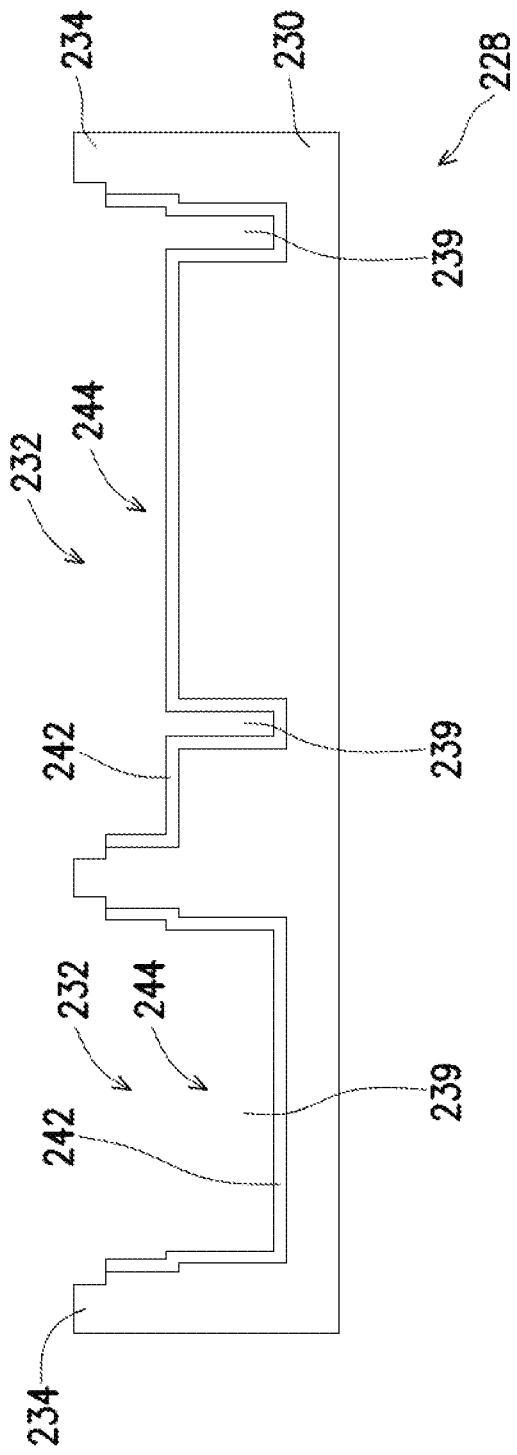

The method 600 then proceeds to step 622. At step 622, a reference electrode is deposited in one of the opening(s). As a result, the reference electrode is connected to one conductive line exposed in the opening at step 620. As mentioned above, the reference electrode may be made of one of the following materials: Ag/AgCl, Cu/CuSO$_4$, AgCl, Au, and P. For Ag/AgCl, a chemical treatment may be required on the deposited and patterned Ag layer to create the AgCl. For Cu/CuSO$_4$, a chemical treatment may be required on the deposited and patterned Cu layer to create the CuSO$_4$. As shown in FIG. 14, the reference electrode 227 is deposited in the opening 225a formed at step 620. The electrode 227 is connected to the conductive line 214a exposed in the opening 225a.

The method 600 then proceeds to step 624. At step 624, a cap structure is fabricated. FIG. 6C is a flowchart diagram illustrating the step 624 of the method 600 of FIG. 6B in accordance with some embodiments. The step 624 is a CMOS-compatible process flow. At step 652, a cap structure substrate is provided. The cap structure substrate may be a silicon substrate, though other suitable materials may be employed. As shown in the example in FIG. 15, a silicon substrate 230 is provided.

At step 654, the cap structure substrate is patterned and etched to predefine global cavity regions. The global cavity region corresponds to the microfluidic channel. A photoresist pattern is formed on the cap structure substrate. The photoresist pattern protects some of the cap structure substrate from a subsequent etch to predefine the global cavity region. After patterning the cap structure substrate, the global cavity regions are predefined by etching the cap structure substrate. The etching process may be a wet etch, such as HF/nitric/acetic acid (HNA) or tetramethylammonium hydroxide (TMAH) or dry etch including plasma and non-plasma etch. Afterwards, the photoresist is removed. As shown in the example in FIG. 16, two global cavity regions 232 are predefined at the top surface of the cap structure substrate 230, and the cap structure substrate 230 has been etched from 0.11 μm to 0.51 μm in this example.

At step 656, a hard mask is deposited on bonding areas of the cap structure substrate. In some embodiments, the bonding areas of the cap structure substrate correspond to the bonding sites on the buried oxide layer at step 618. Specifically, the bonding areas of the cap structure substrate interface with the bonding sites on the buried oxide layer, and the cap structure is bonded to the buried oxide layer (or any appropriate intermediate bonding layer deposited and patterned on the buried oxide layer), which will be described in detail below at step 626. The hard mask can protect the bonding areas from subsequent etching processes. In some embodiments, the hard mask may be formed of oxide. In some embodiments, the hard mask may be formed of poly silicon. The hard mask is formed using suitable processes such as CVD and/or the like. In a non-limiting example, the thickness of the hard mask ranges from 0.3 μm to 1 μm. As shown in the example in FIG. 17, the hard masks 236 (e.g., oxide hard mask) are deposited on the bonding areas 234 of the cap structure substrate 230. The hard masks 236 may protect the bonding areas 234 from subsequent etching processes.

At step 658, certain regions of the global cavity regions are patterned and etched. A photoresist pattern is formed on the hard mask and portions of the global cavity regions. The photoresist pattern protects the hard mask and portions of the global cavity region from a subsequent etch. Subsequently, the cap structure substrate is etched. The etching process may be a wet etch, such as HF/nitric/acetic acid (HNA) or tetramethylammonium hydroxide (TMAH) or dry etch including plasma and non-plasma etch. Afterwards, the photoresist is removed. As shown in the example in FIG. 18, the photoresist pattern 238 is on the hard mask 236 and portions of the global cavity regions 232. The exposed portions of the global cavity region 232 are etched to form deep regions 239. The photoresist pattern 238 is then removed, and the structure is as shown in the example in FIG. 19. The entire global cavity regions 232, including the deep regions 239, are exposed, while the bonding areas 234 are covered by the hard masks 236.

At step 660, the entire global cavity regions are blanket etched. Specifically, the entire global cavity regions, including the deep regions, are etched back evenly by a certain depth, to form the chambers of the cap structure. The chambers of the cap structure may be used as either fluid chambers (e.g., the fluid chamber 454 as shown in FIG. 4A) or drug channels (e.g., the drug channel 455 as shown in FIG. 4A). On the other hand, the bonding areas covered by the hard masks are protected during the blanket etch. The blanket etching process may be any suitable etching processes such as wet etch or dry etch including plasma and non-plasma etch. As shown in the example in FIG. 20, the entire global cavity regions 232 of the cap structure substrate 230, including the deep regions 239, are etched by a predefined etch depth ED. The predefined etch depth ED corresponds to the desired height of the chambers 244 of the cap structure 228.

Optionally at step 662, a high-k dielectric material layer is deposited on the global cavity regions and the hard masks. Step 662 is optional depending on applications. The high-k dielectric material layer may be formed using CMOS processes such as, for example, PVD (sputtering), CVD, PECVD, APCVD, LPCVD, HDPCVD, or ALCVD. In one non-limiting example, the high-k dielectric material layer has a thickness of 2 nm to 3 nm. As shown in the example in FIG. 21, the high-k dielectric material layer 242 is deposited on the global cavity regions 232 (thus the chambers 244) and the hard masks 236. The high-k dielectric material layer 242 covers the bottom and sidewalls of the chambers 244, the bottom and sidewalls of the deep regions 239, and the hard mask 236.

Optionally at step 664, the interface layer on the top of the hard mask is removed. In one embodiment, a photoresist spray coater may be sprayed, by a spray coating process, to cover the global cavity region. The photoresist spray coater protects the high-k dielectric material layer when the high-k dielectric material layer on the hard mask is removed. The interface layer on the top of the hard mask is removed by suitable processes such as plasma etching. In an example plasma etching process, a mixture of gasses comprising oxygen, a fluorine-containing material and an inert gas is provided, and a high-speed stream of glow discharge (plasma) of the mixture of gasses is shot (in pulses) at the high-k dielectric material layer. The spray coating process is used to coat photoresist over a region with deep features. In the spray coating process, fine droplets of photoresist are deposited onto the structure. The angle at which the photoresist droplets are sprayed permits the photoresist to make its way into the deep trenches and sidewalls.

At step 666, the hard mask is removed. The hard mask is removed by any suitable processes. In one embodiment, the hard mask is removed by wet etch. In some embodiments, the wet etch is a fluorine containing etch, such as dilute hydrofluoric acid (HF). In some embodiments, the wet etch is an ammonia hydroxide/hydrogen peroxide etch. The wet etch removes the hard mask without substantially removing or harming the high-k dielectric material layer. As shown in the example in FIG. 22, the optional high-k dielectric material layer 242 on the hard mask 236 and the hard mask 236 are removed at step 664 and step 666, respectively. The bonding areas 234 are exposed. The bottom and sidewalls of the global cavity regions 232 and deep regions 239 are covered with the high-k dielectric material layer 242. As such, the cap structure 228 is fabricated.

Referring back to FIG. 6B, the method 600 proceeds to step 626 where the cap structure is bonded to the backside of the biosensor system package. Specifically, the cap structure is bonded to the buried oxide layer. In some embodiments, the bonding sites of the buried oxide layer interface with the bonding areas of the cap structure substrate. In other embodiments, an intermediate bonding layer, that is deposited and patterned on the buried oxide layer, interfaces with the bonding areas of the cap structure substrate. The cap structure may be bonded to the backside of the biosensor system package using fusion bond, eutectic bond, anodic bond, and/or other suitable bonding methods. Fusion bonding utilizes temperature and pressure to join semiconductor materials. In one non-limiting example, in a room-temperature fusion bonding process, a bonder device forces the cap structure and the backside of the biosensor system package together. This is followed by an annealing process to increase the bond strength. In a eutectic bond, an intermediate metal layer that can produce a eutectic system is utilized. The eutectic metals are alloys that transform directly from solid to liquid state, or vice versa from liquid to solid state, at a specific composition and temperature without passing a two-phase equilibrium. As the eutectic temperature can be much lower than the melting temperature of the two or more pure elements, the eutectic bond may have the benefits of low processing temperatures, low resultant stress induced in final assembly, high bonding strength, large fabrication yield and a good reliability. In an anodic bond, glasses are sealed to either silicon or metal without introducing an intermediate layer.

Figure 23:
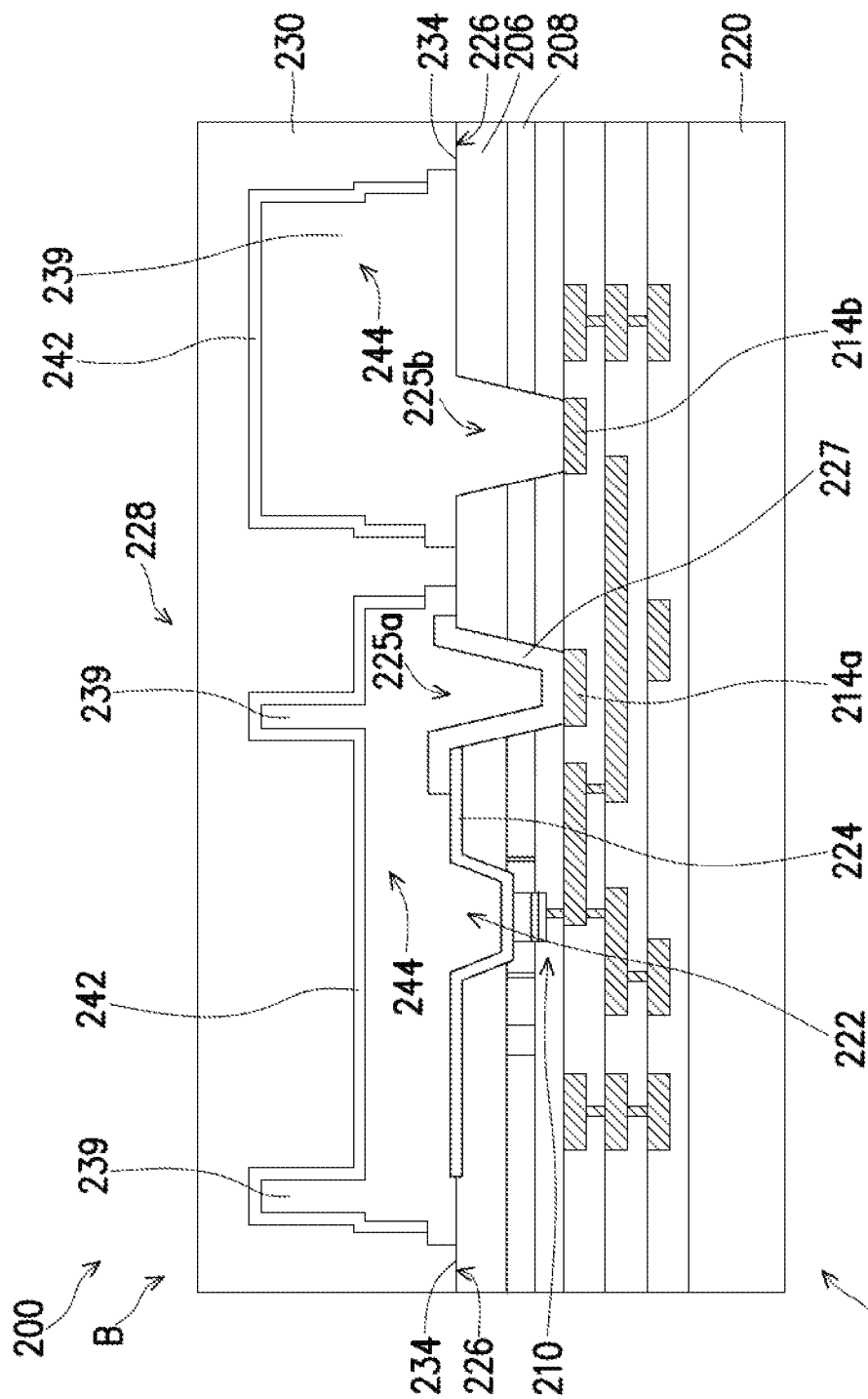

As shown in the example in FIG. 23, the cap structure 228 is bonded to the backside (B) of the biosensor system package 200. Specifically, the cap structure 228 is bonded to the buried oxide layer 206. The bonding sites 226 of the buried oxide layer 206 interface with the boding areas 234 of the cap structure substrate 230. In the example shown in FIG. 23, the conductive line 214b, as mentioned above with reference to FIG. 14, may be used for wire bonding later.

Figure 24:
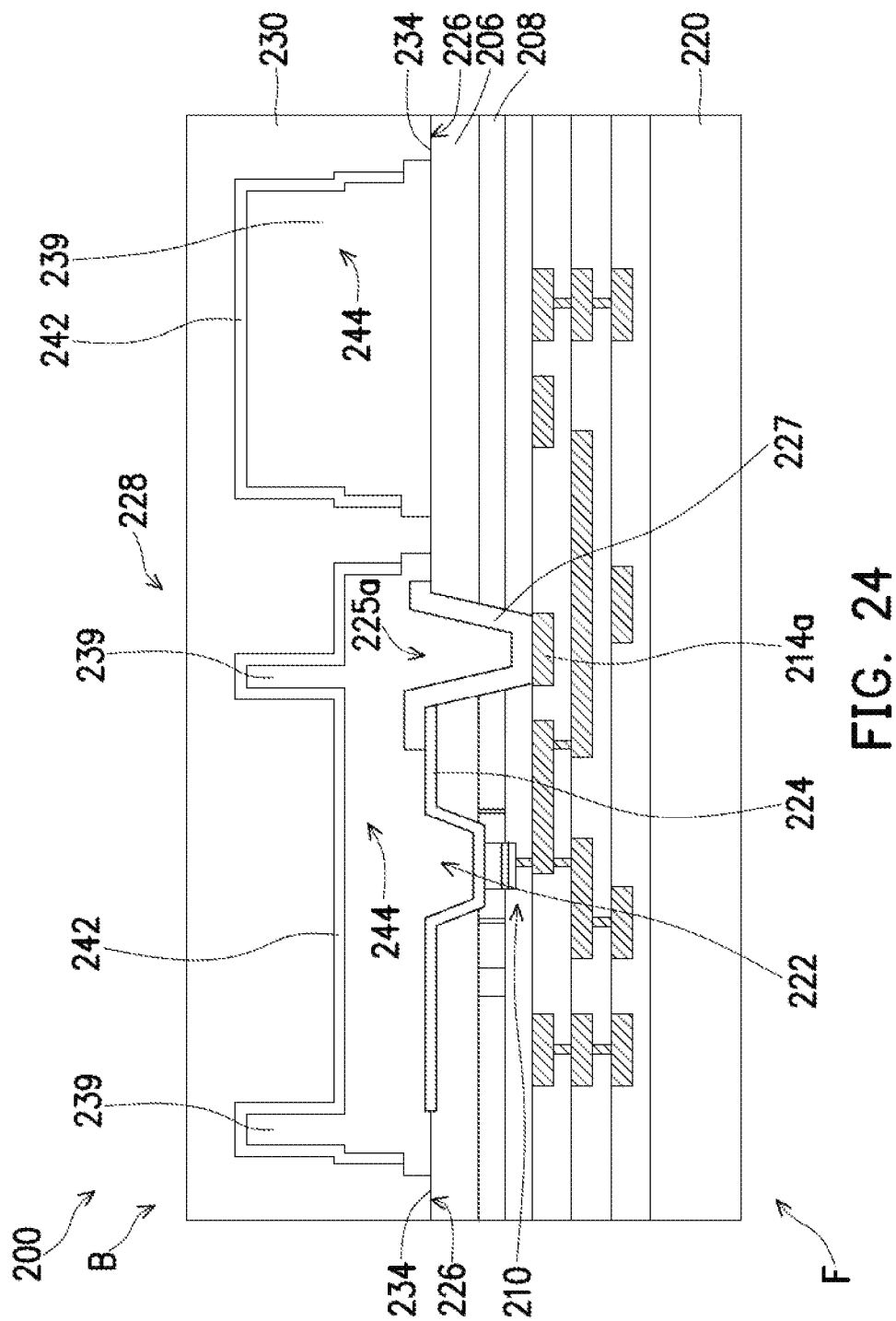

Alternatively, as shown in the example in FIG. 24, the cap structure 228 is bonded to the backside (B) of the biosensor system package 200. Different from the example shown in FIG. 23, a through-substrate via (TSV) structure rather than a wire bonding is used for connecting the biosensor system package 200 with a separate chip later. The TSV structure will be described in detail below.

Figure 25:
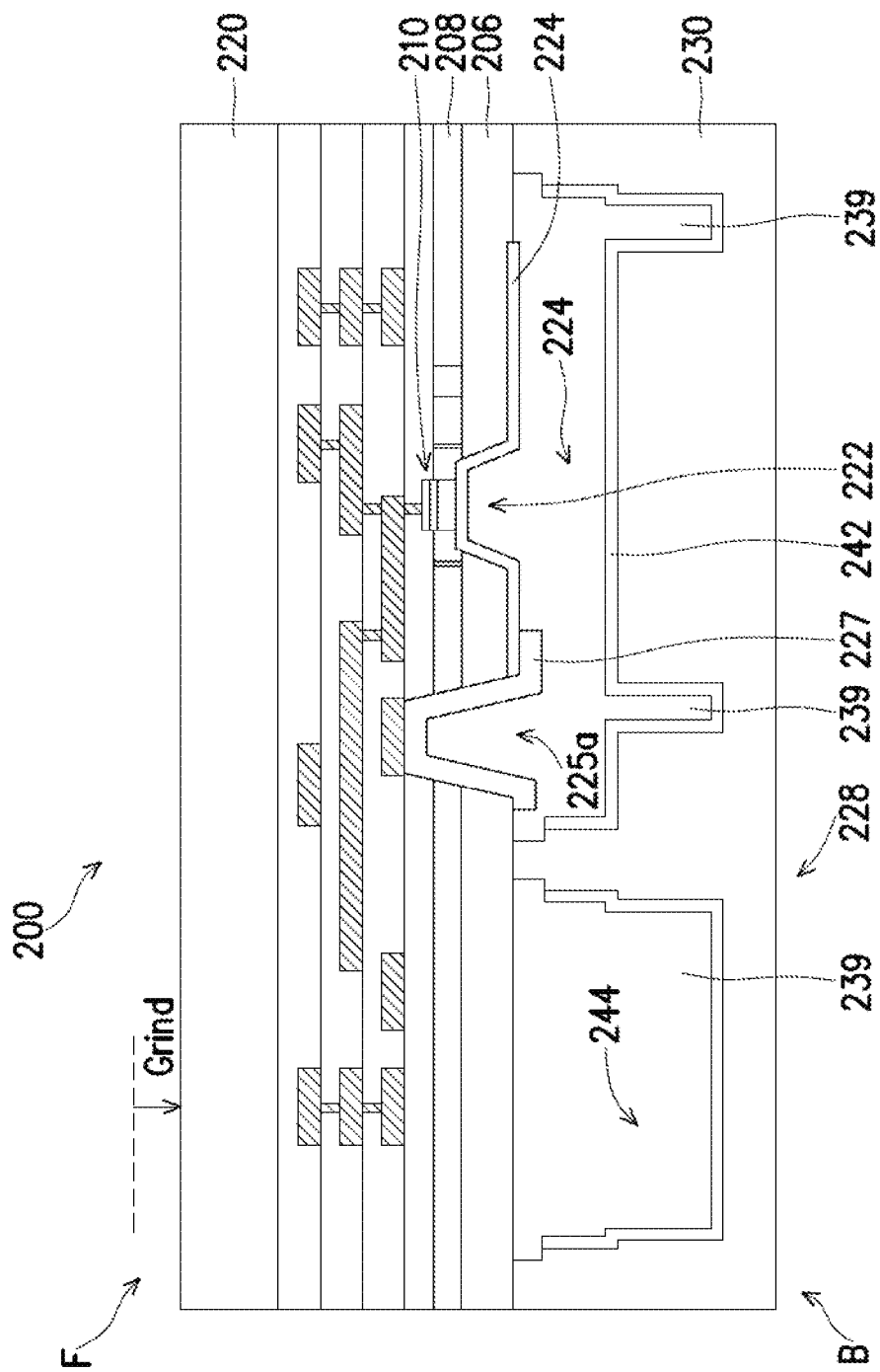
Figure 26:
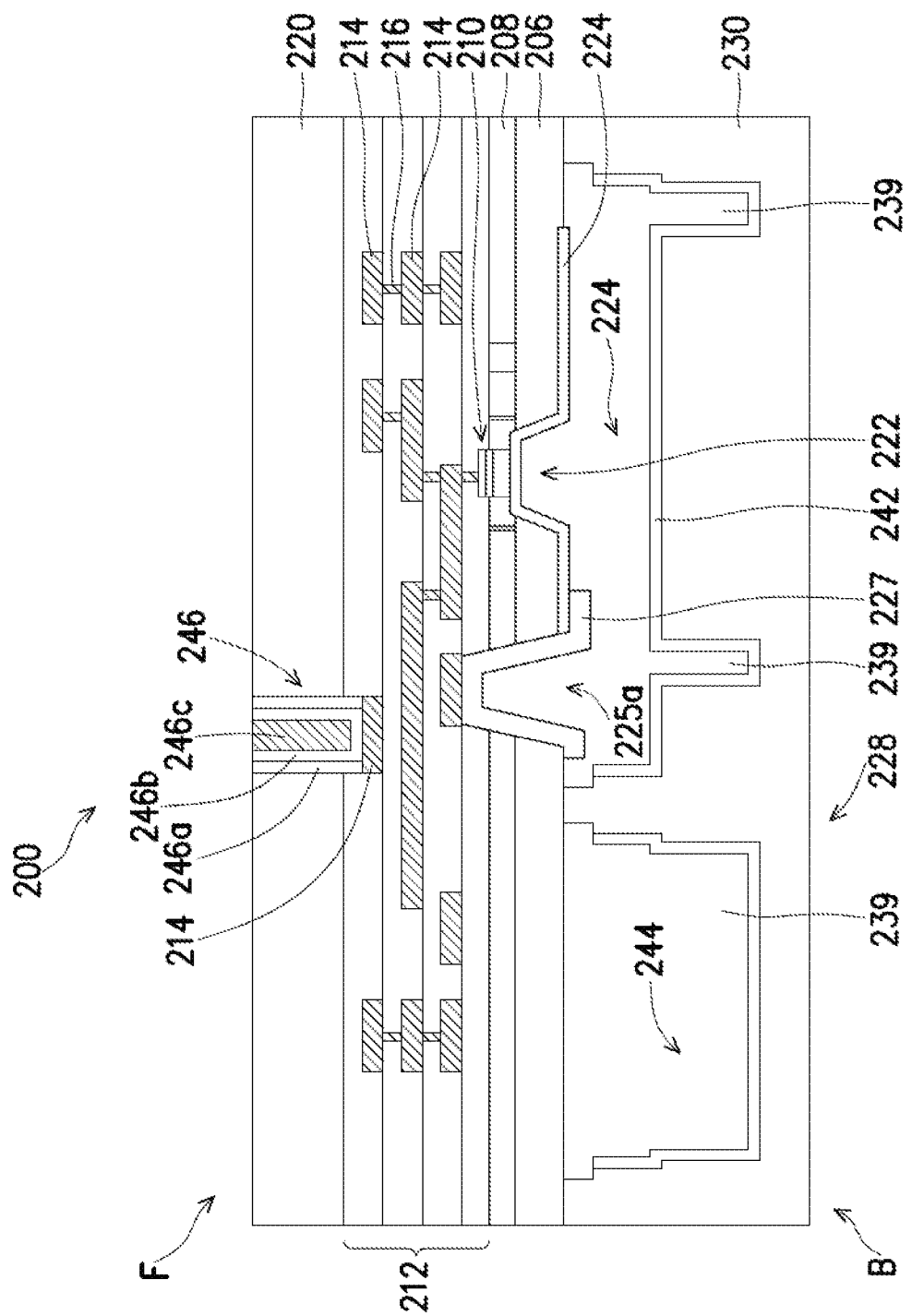
Figure 27:
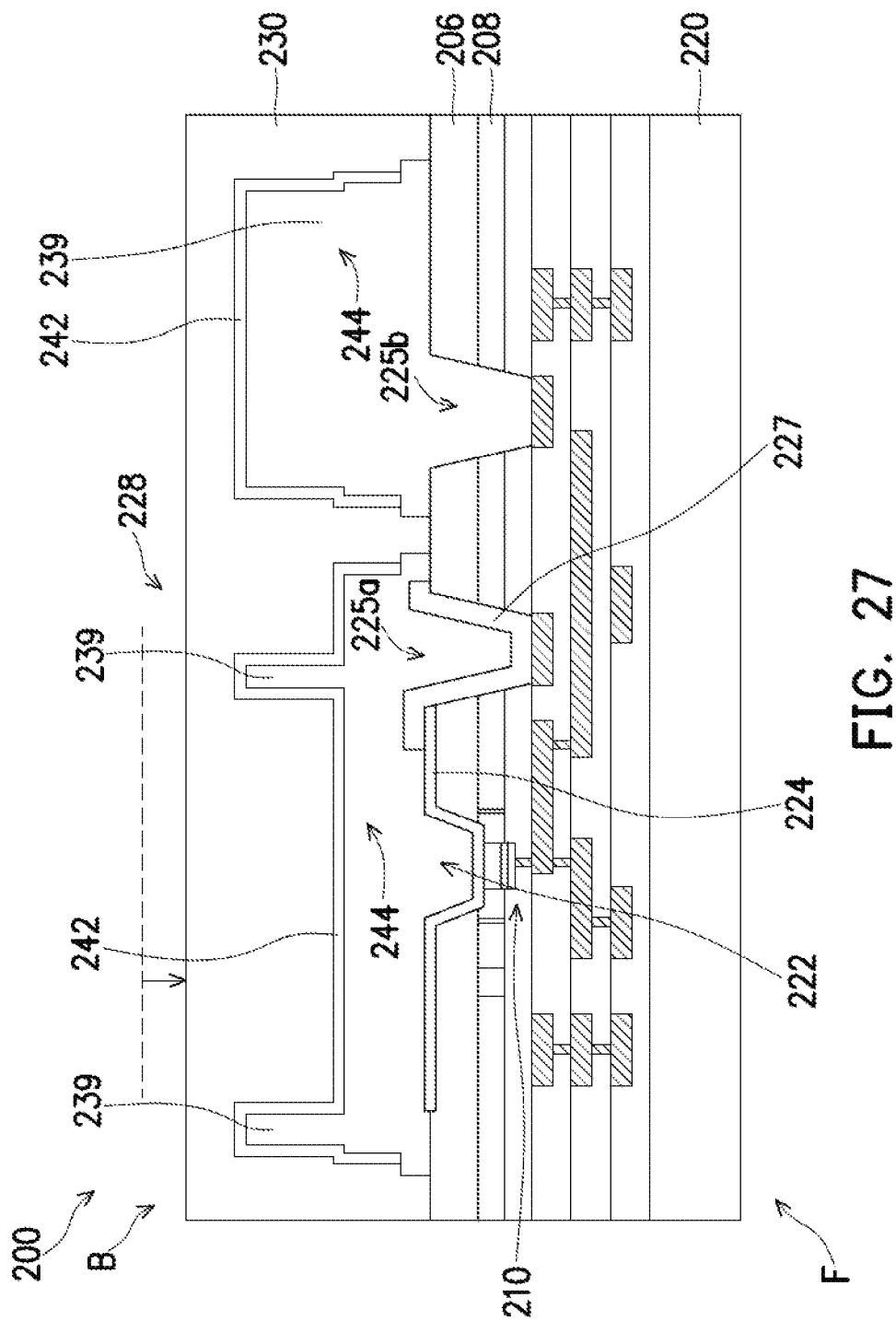
Figure 28:
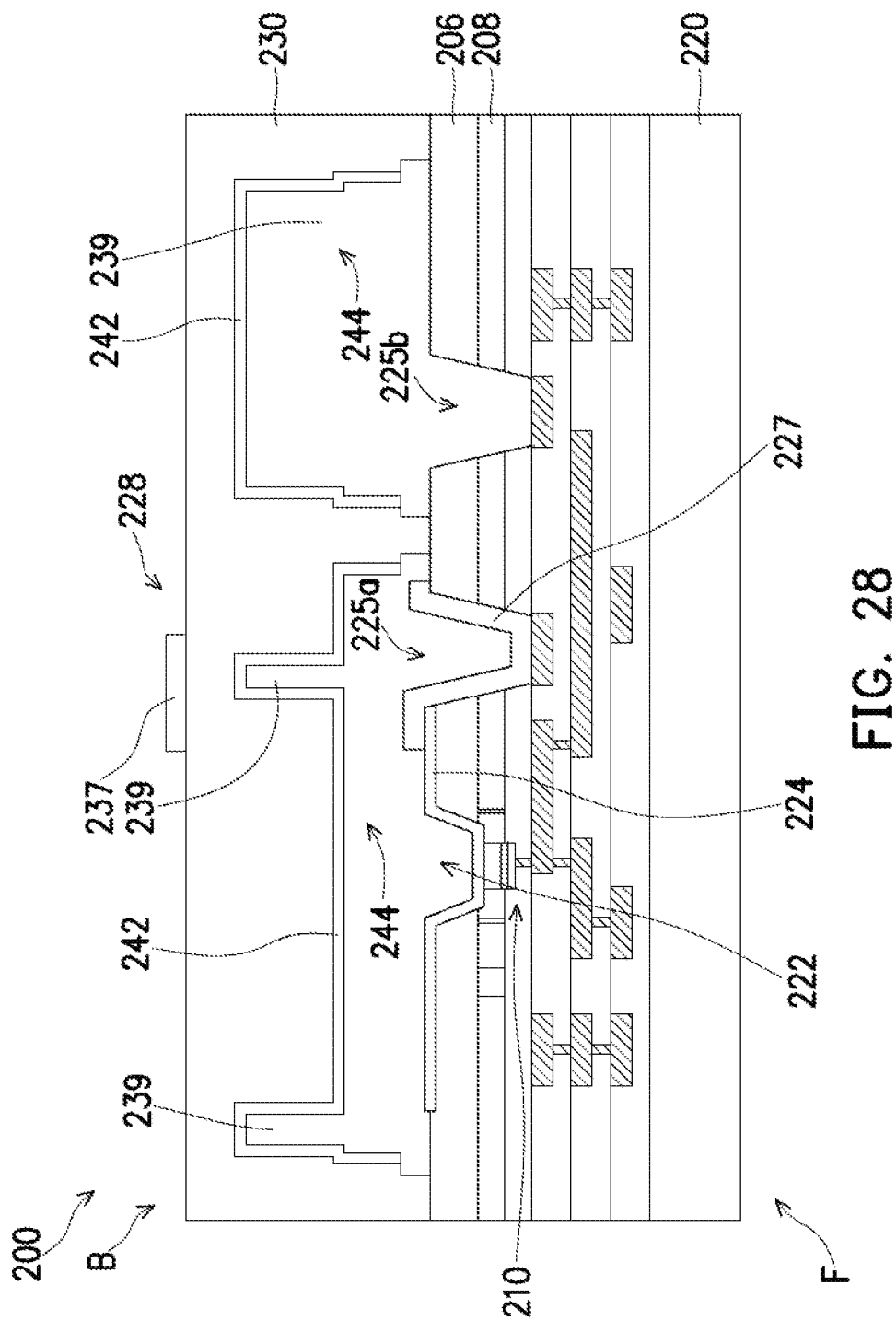

For embodiments with TSV structures as mentioned above, the method 600 then optionally proceeds to step 628 where the wafer is flipped. Afterwards, the carrier substrate which is at the front side (F) of the biosensor system package is now on the top. The method 600 then optionally proceeds to step 630 where the carrier substrate is thinned. In one example, the carrier substrate is thinned by grinding. The grinding process may include rotating a disk holding the biosensor system package lined with an appropriate grinding material. It should be noted that other processes such as CMP may also be employed. As shown in FIG. 25, the carrier substrate 220 has been thinned. The thickness of the carrier substrate is selected in accordance with step 632 which will be discussed below.

The method 600 then optionally proceeds to step 632 where a through-substrate via (TSV) structure is created through the carrier substrate and connected to the MLI structure. The TSV is used to provide electrical connections and for heat dissipation for the biosensor system package 200. As shown in the example in FIG. 26, a TSV structure 246 is created through the carrier substrate 220 and connected to the MLI structure 212. Although only one TSV structure 246 is shown in the example in FIG. 26, more than one TSV structure may be formed to pass through the carrier substrate 220. The TSV structure 246 includes a liner 246a, a diffusion barrier layer 246b, and a conductive material 246c. In one embodiment, the TSV structure 246 is formed by the following operations. Firstly, a TSV opening is formed extending to a conductive line 214 of the MLI structure 212 by one or more etching processes. After the TSV opening is formed, the liner 246a is formed on sidewalls of the TSV opening to act as an isolation layer, such that the conductive material 246c of the TSV structure 246 and the carrier substrate 220 do not directly contact with each other. Afterwards, the diffusion barrier layer 246b is conformally formed on the liner 246a and on the bottom of the TSV opening. The diffusion barrier layer 246b is used to prevent the conductive material 246c, which will be formed later, from migrating to undesired regions. After the diffusion barrier layer 246b is formed, the conductive material 246c is used to fill into the TSV opening. Afterwards, excess liner 246a, diffusion barrier layer 246b, and conductive material 246c, which are on the outside of the TSV opening, are removed by a planarization process, such as a chemical mechanical polishing (CMP) process, although any suitable removal process may be used.

The liner 246a is made of an insulating material, such as oxides or nitrides. The liner 246a may be formed by using a PECVD process or other applicable processes. The liner 246a may be a single layer or multi-layers. In some non-limiting examples, the liner 246a has a thickness in a range from about 100 Å to about 5000 Å. The diffusion barrier layer 246b is made of Ta, TaN, Ti, TiN or CoW. In some embodiments, the diffusion barrier layer 246b is formed by a PVD process. In some embodiments, the diffusion barrier layer 246b is formed by plating. In some embodiments, the conductive material 246c is made of copper, copper alloy, aluminum, aluminum alloys, or combinations thereof. Alternatively, other applicable materials may be used. The width, depth, and aspect ratio of the TSV structure 246 may be selected under different circumstances. Since the carrier substrate 220 is thinned at step 630, the TSV structure 246 has a relatively small aspect ratio. As such, the void problems and the extrusion or diffusion problems resulting from a high aspect ratio of the TSV structure are resolved or greatly reduced. In addition, the overall package height of the biosensor system package 200 is reduced to meet advanced packaging requirements. As such, the biosensor system package 200 may achieve a small form factor.

The method 600 then proceeds to optional step 634 where the wafer is flipped for the case where a TSV structure was created. Afterwards, the cap structure is on the top, whereas the TSV structure is at the bottom. The method 600 then proceeds to step 636 where microneedle(s) are created at the back side (B) of the biosensor system package. FIG. 6D is a flowchart diagram illustrating the step 636 of the method 600 of FIG. 6B in accordance with some embodiments. FIG. 6E is another flowchart diagram illustrating the step 636 of the method 600 of FIG. 6B in accordance with some embodiments. The step 636 is a CMOS-compatible process flow.

Referring to FIG. 6D, the method 636 starts optionally at step 672 where the cap structure substrate is thinned. Step 672 is optional and depends on microneedle height(s). The cap structure substrate is thinned by any suitable processes such as grinding and CMP. In the example shown in FIG. 27, the cap structure substrate 230 is thinned by grinding the top part of the cap structure 228.

The method 636 then proceeds to step 674. At step 674, hard mask(s) are deposited at microneedle position(s). For simplicity, the situation of one microneedle is described below. The hard mask at the microneedle position can protect the microneedle position from subsequent etching processes. In some embodiments, the hard mask may be formed of oxide. In some embodiments, the hard mask may be formed of polysilicon. The hard mask is formed using suitable processes such as CVD and/or the like. As shown in the example in FIG. 28, the hard masks 237 (e.g., oxide hard mask) are deposited on the cap structure substrate 230 at the microneedle position. The hard masks 237 may protect the microneedle position from subsequent etching processes.

In one embodiment, the method 636 then proceeds to step 676 and step 678. At step 676, the cap structure substrate is etched using isotropic etching and anisotropic etching in an alternate manner (i.e., multiplexing). In other words, the etching process is switching between isotropic etching and anisotropic etching. Isotropic etching is an etching process that removes a material in multiple directions, and therefore any horizontal components of the etch direction may result in undercutting of patterned areas. Anisotropic etching, on the other hand, is an etching process that aims to preferentially remove a material in specific directions to obtain intricate and often flat shapes. In one embodiment, the anisotropic etching used here is anisotropic deep reactive ion etching (DRIE) while the isotropic etching used here is sulfur hexafluoride ($SF_6$) plasma etching. Specifically, the Bosch process (i.e., pulsed or time-multiplexed etching) is used. In some embodiments, after the etching process, the apex of the microneedle is sharpened by a final wet oxidation following by a consecutive oxide strip. The oxidation is made with the hard mask still being on the microneedle, which may result in a sharp apex. In the example shown in FIG. 29, after step 676, the deep regions 239 are opened, and the chambers 244 can therefore be connected outside. A microneedle 241 is formed at the microneedle position.

Figure 29:
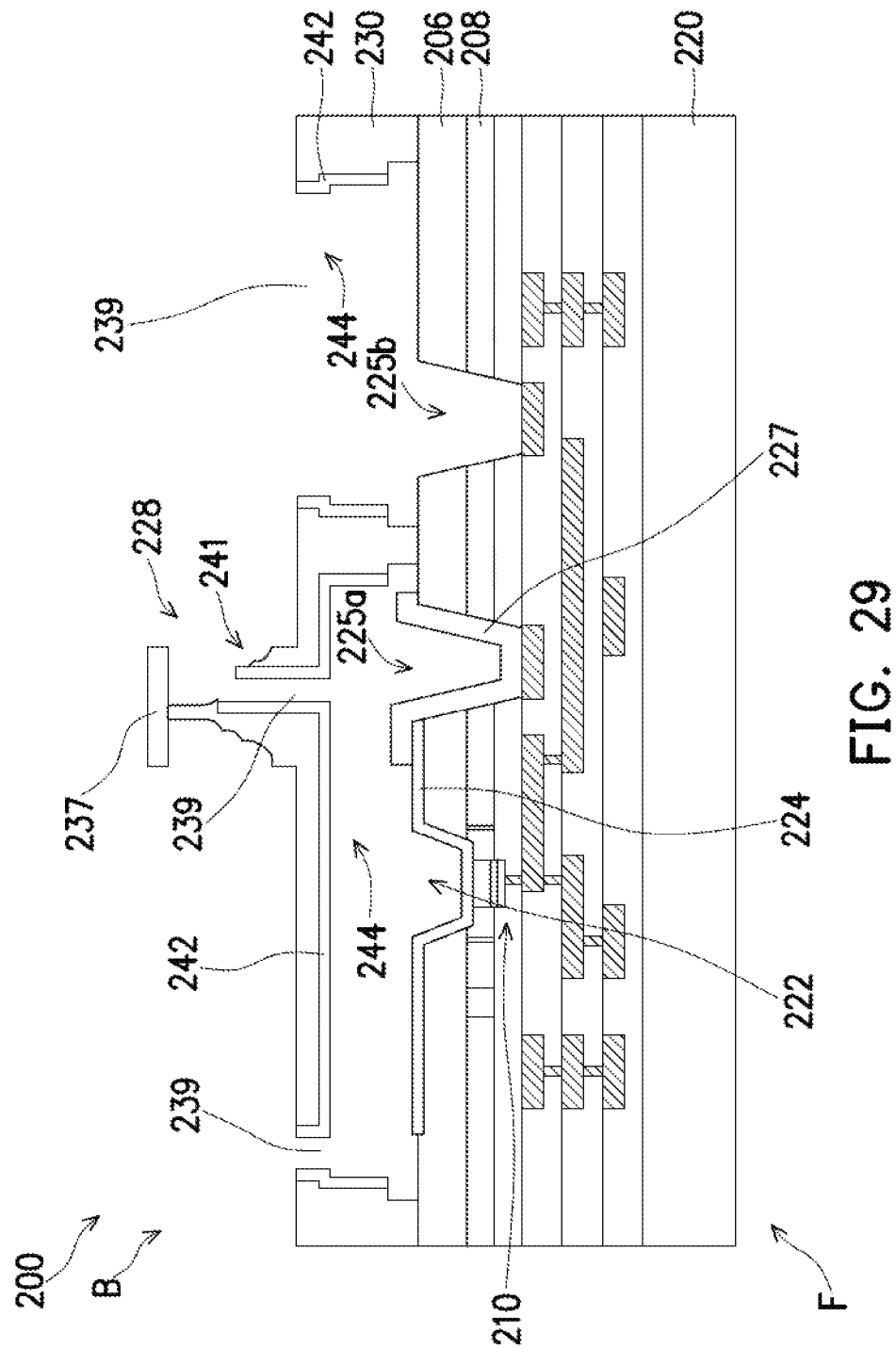
Figure 30:
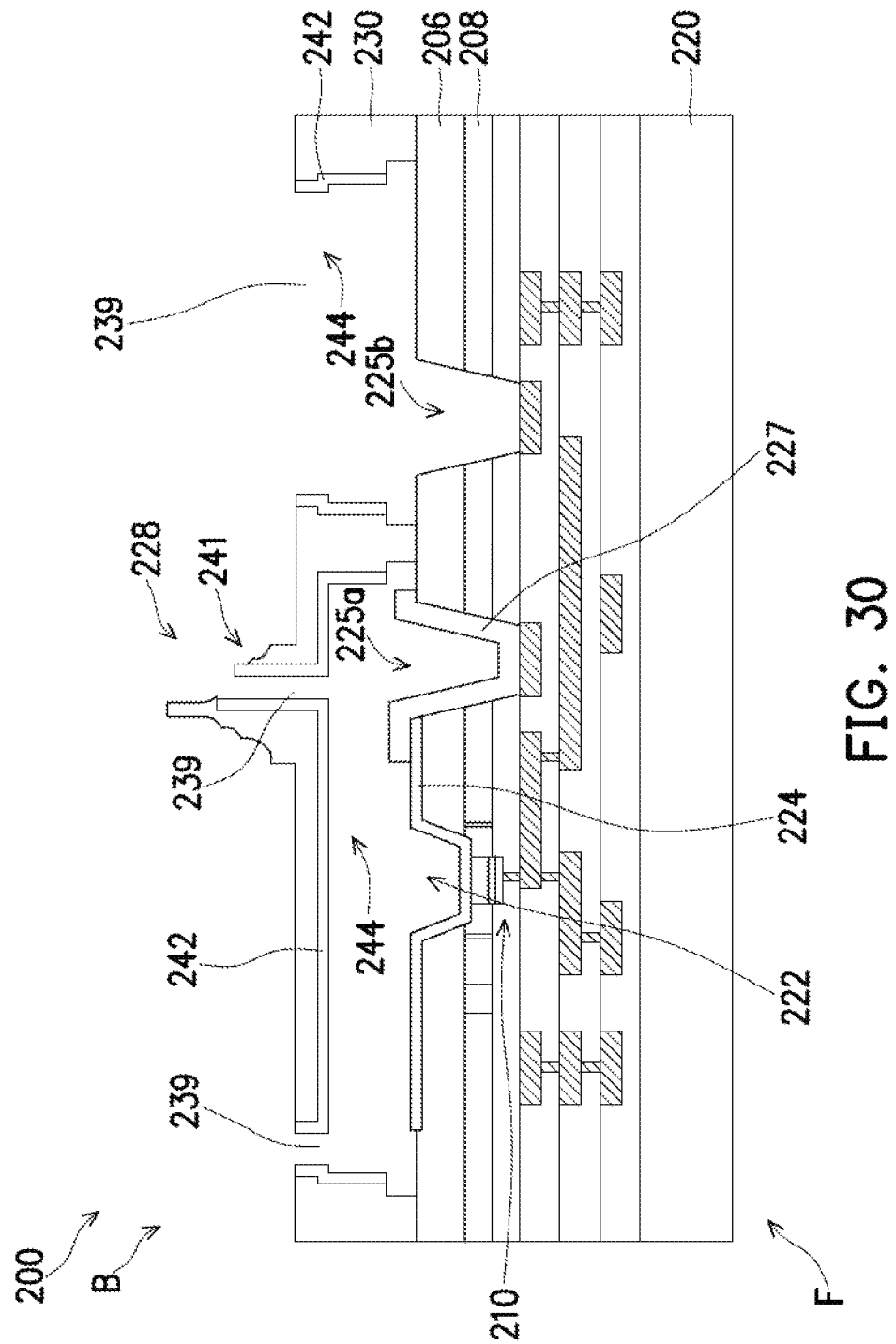

The method 636 then proceeds to step 678, where the hard mask(s) are removed. The hard mask is removed by any suitable processes. In one embodiment, the hard mask is removed by wet etch. In some embodiments, the wet etch is a fluorine containing etch, such as dilute hydrofluoric acid (HF). In some embodiments, the wet etch is an ammonia hydroxide/hydrogen peroxide etch. As shown in the example in FIG. 30, the hard mask 237 shown in FIG. 29 is removed at step 678. The apex of the microneedle 241 is therefore exposed. As such, the microneedle 241 is fabricated.

Alternatively in another embodiment, the method 636 may proceed to steps 680, 682, and 684. At step 680, the cap structure substrate is etched using anisotropic etching by a predetermined depth. The predetermined depth is approximate to a height of a microneedle. In one embodiment, the anisotropic etching used here is anisotropic deep reactive ion etching (DRIE). At step 682, the hard mask is removed. The hard mask is removed by any suitable processes. In one embodiment, the hard mask is removed by wet etch. In some embodiments, the wet etch is a fluorine containing etch, such as dilute hydrofluoric acid (HF). In some embodiments, the wet etch is an ammonia hydroxide/hydrogen peroxide etch. Then at step 684, the cap structure substrate is etched using isotropic etching to form apex(es) of the microneedle(s). In some embodiments, the isotropic etching used here is sulfur hexafluoride (SF$_6$) plasma etching. The horizontal removal of the cap structure substrate 230 help form apex(es) of the microneedle(s).

Figure 31:
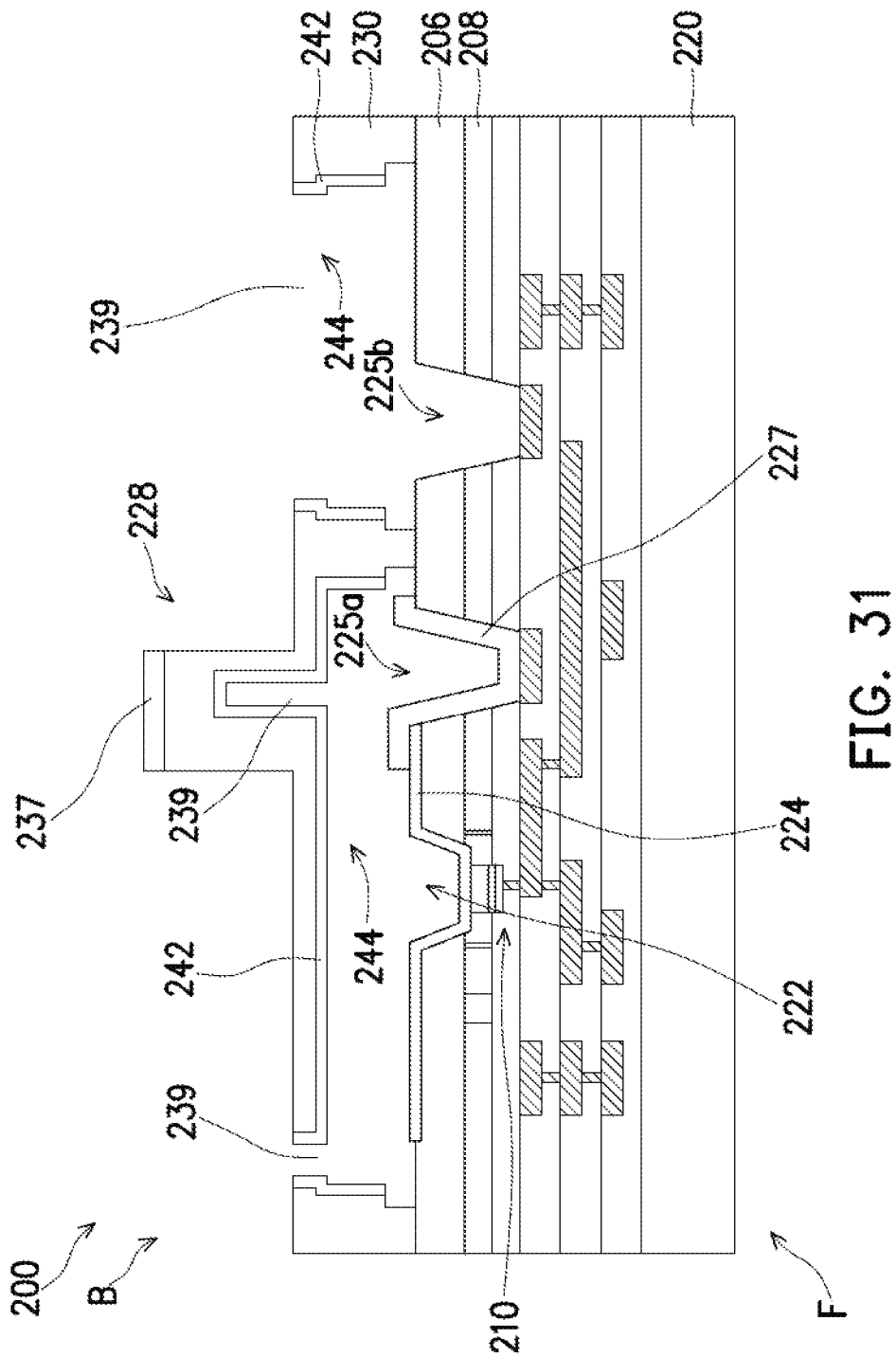
Figure 32:
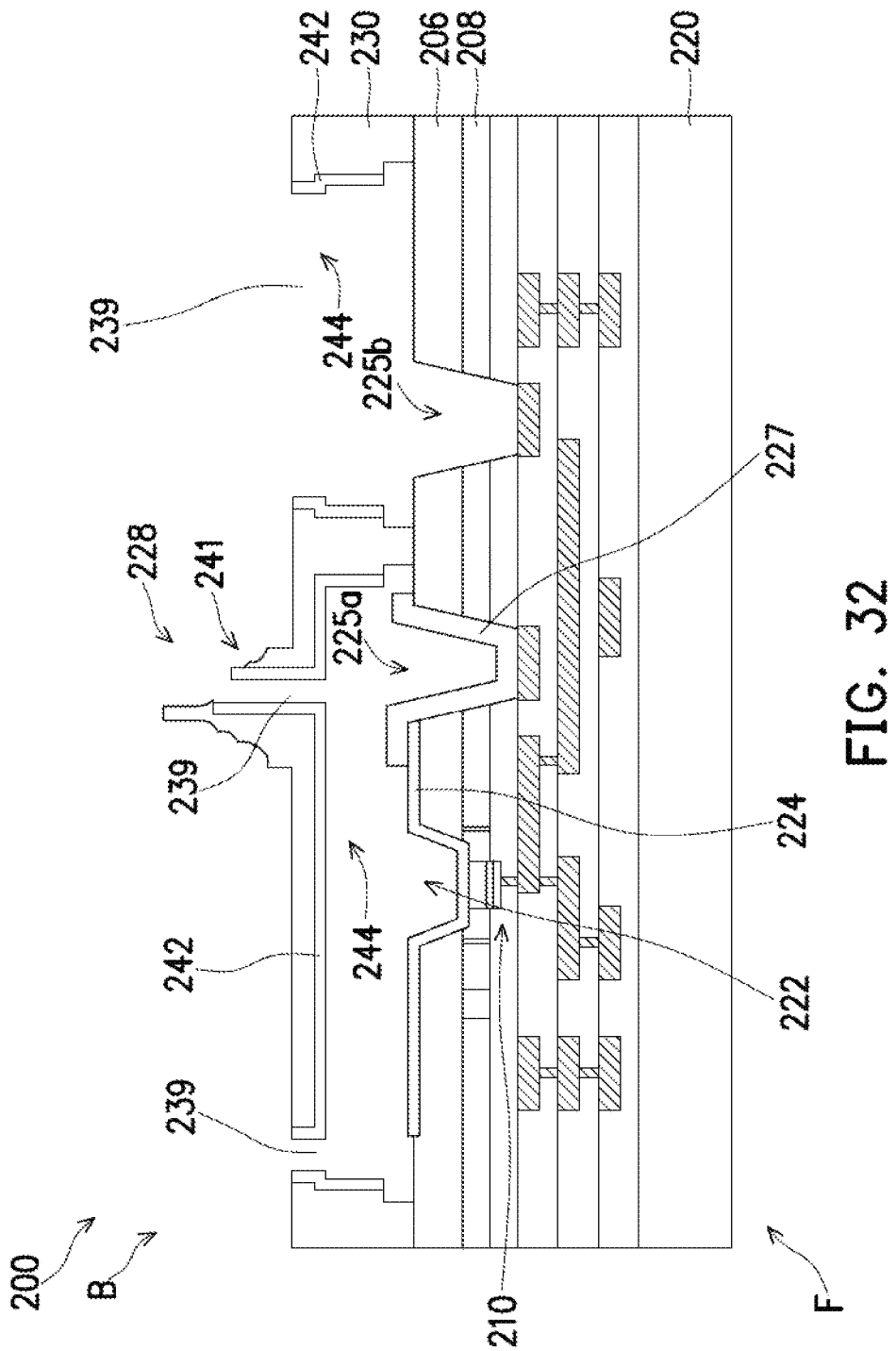
Figure 33:
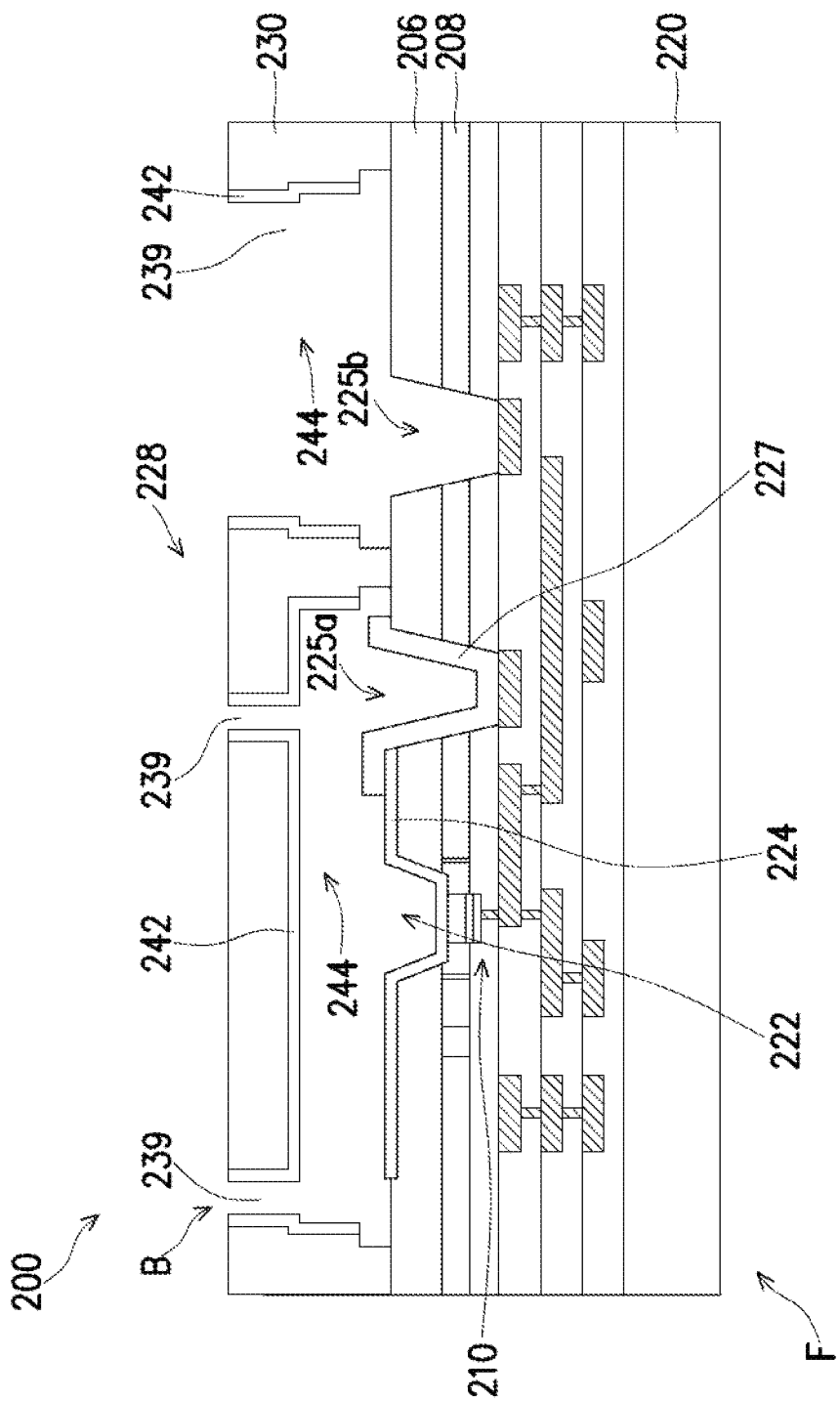
Figure 34:
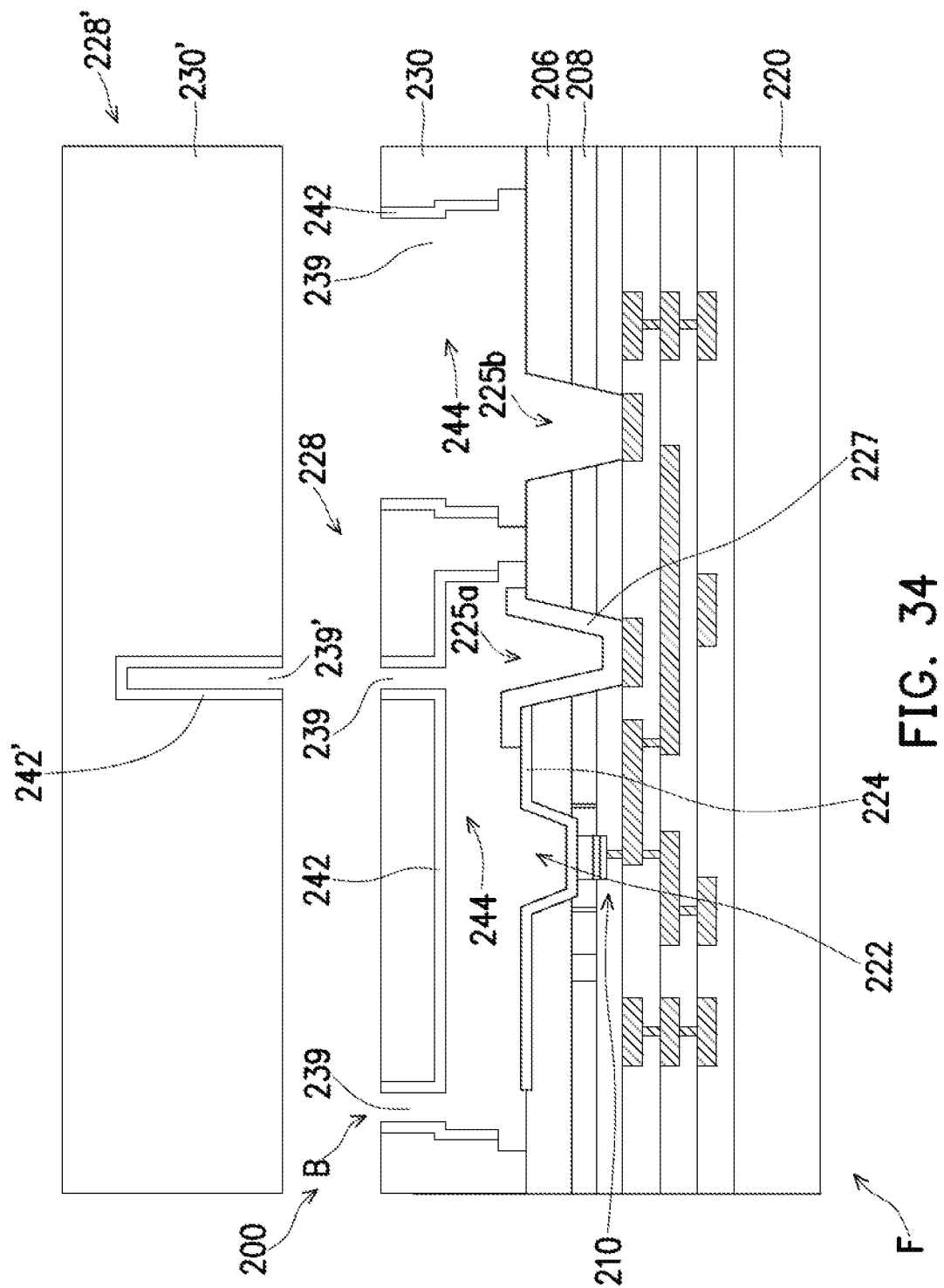

In the example shown in FIG. 31, after step 680, the deep regions 239, except the deep region 239 corresponding to the microneedle position, are opened, and the chambers 244 can therefore be connected outside. In the example shown in FIG. 32, after step 682 and step 684, the hard mask 237 shown in FIG. 31 is removed at step 682. The top of the microneedle 241 is therefore exposed. The top of the microneedle 241 is further sharpened to form the apex after step 684. As such, the microneedle 241 is fabricated.

Referring to FIG. 6E, the method 636 shown in FIG. 6E applies to relatively long microneedles. Relatively long microneedles may be desirable in certain applications. As shown in FIG. 6E, the method 636 starts at step 691 where the cap structure substrate is thinned to open the deep regions. The cap structure substrate is thinned by any suitable processes such as grinding and CMP. In the example shown in FIG. 33, the cap structure substrate 230 is thinned by grinding the top part of the cap structure 228. After step 691, the deep regions 239 are opened, and the chambers 244 can therefore be connected outside.

Figure 35:
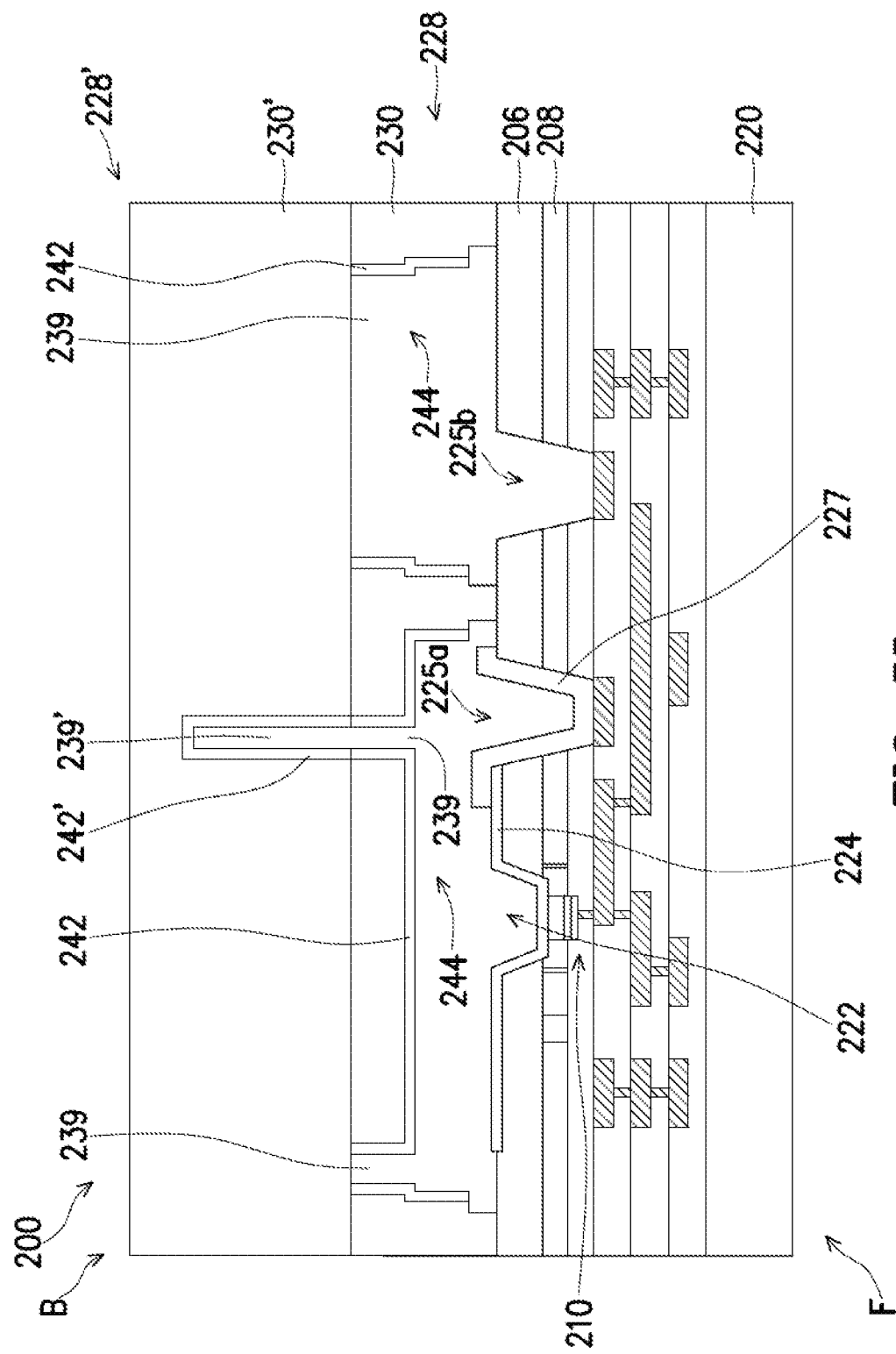
Figure 36:
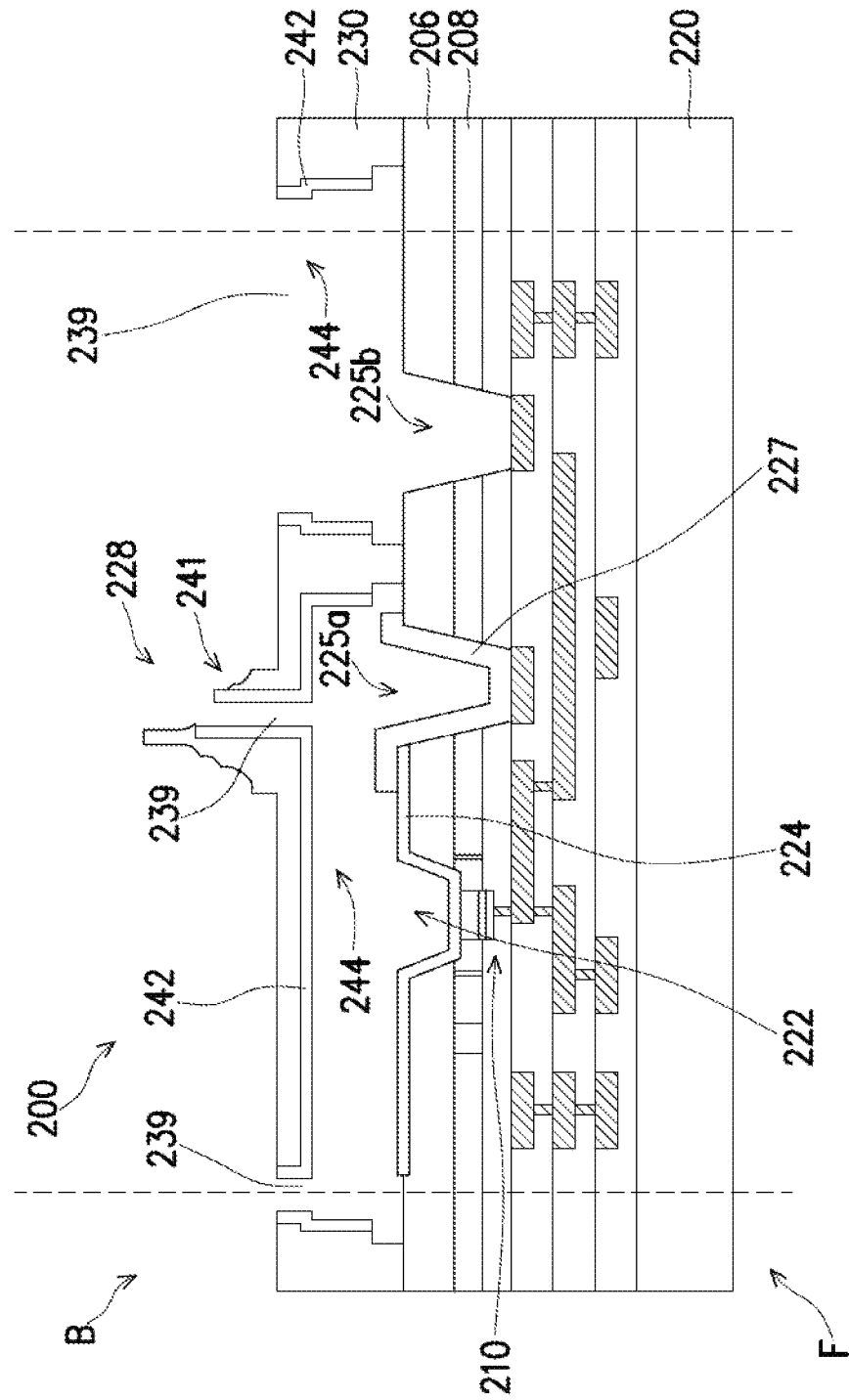

The method 636 then proceeds to step 692 where a second cap structure is fabricated and bonded to the cap structure. In the example shown in FIG. 34, a second cap structure 228' is fabricated. The fabrication process of the second cap structure 228' is similar to method 624 as shown in FIG. 6C, and therefore is not described in detail. The second cap structure 228' has a deep region 239' formed in a cap structure substrate 230'. A high-k dielectric material 242' covers the top surface and sidewalls of the deep region 239'. In the example shown in FIG. 35, the second cap structure 228' is bonded to the cap structure 228. As mentioned above, the second cap structure 228' may be bonded to the cap structure 228 using fusion bond, eutectic bond, anodic bond, and/or other suitable bonding methods. Alignment marks may be employed during the bonding process for alignment. As shown in FIG. 35, the deep region 239 and the deep region 239' are aligned and form a relatively long needle.

The method 636 then proceeds to step 693 where hard mask(s) are deposited at microneedle position(s). In one embodiment, the method 636 proceeds to step 694 and step 695. Alternatively in another embodiment, the method 636 may proceed to step 696, step 697, and step 698. Steps 693-698 are similar to steps 674-684 of FIG. 6D, respectively, therefore are not described in detail again. After implementing the method 636, a relatively long microneedle is fabricated.

Referring back to FIG. 6B, after microneedle(s) are created at the back side of the biosensor system package at step 636, the method 600 then proceeds to step 638. At step 638, the biosensor system package 200 is diced. In the example shown in FIG. 36, the biosensor system package 200 is diced by a dicing tool or saw, at the dashed lines shown in FIG. 36, to be separate from other neighboring components. Alignment marks may be employed in the dicing process.

The method 600 then proceeds to step 640 where a separate chip is connected to the biosensor system package through either wire bonding or the TSV structure. The separate chip may be any chips that function as a portion of the biosensor system. In one embodiment, the separate chip is a RAM chip. In one embodiment, the separate chip is a data processing chip. In one embodiment, the separate chip is a RAM and data processing chip.

Figure 37:
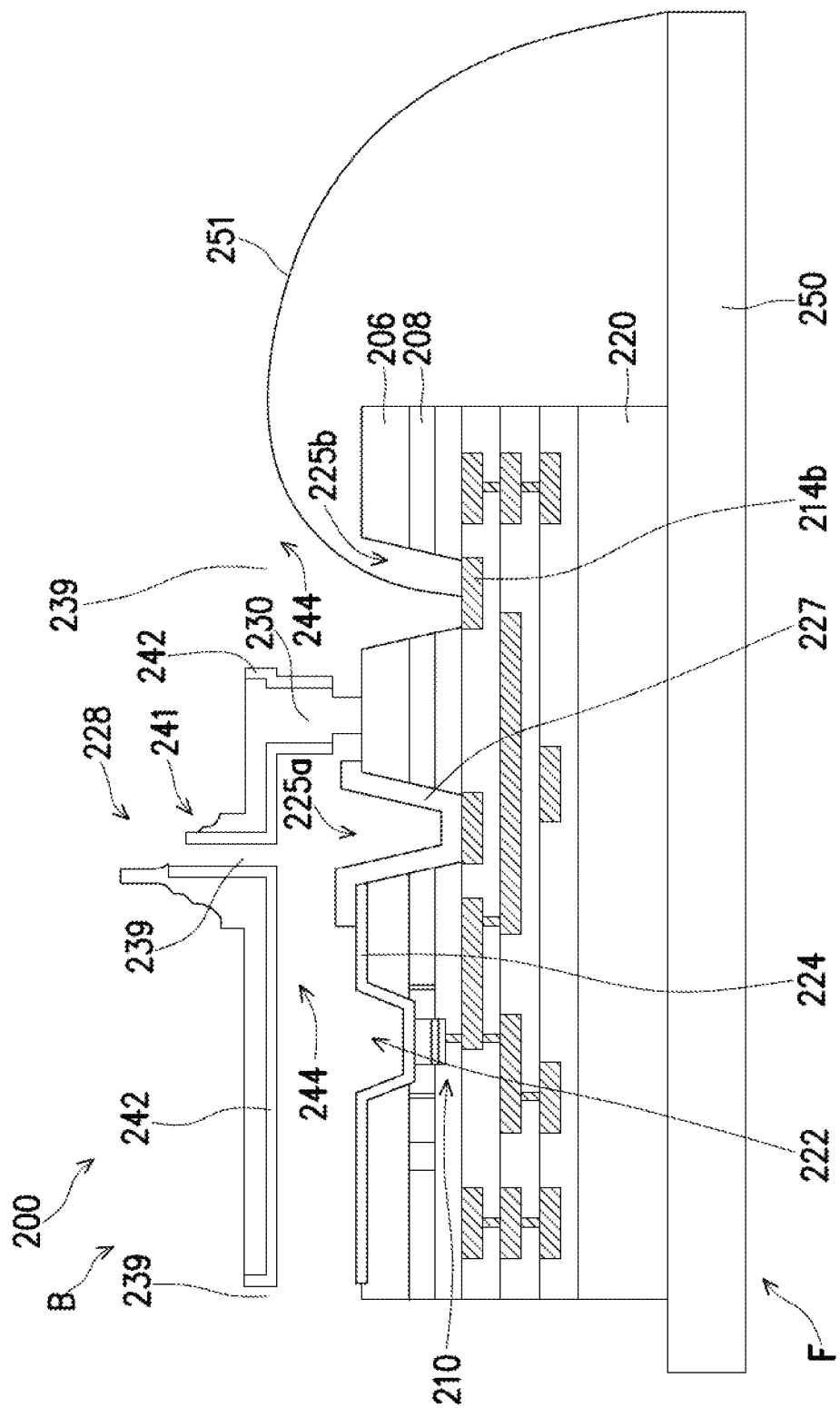

As shown in FIG. 37, the biosensor system package 200 is connected to a separate chip 250 through wire bonding. Wire bonding is a method of making interconnections and is cost-effective and flexible. A metal (e.g., Al, Cu, Ag, or Au) wire 251 connects the separate chip 250 and the conductive line 214b in this example. As such, the biosensor system package 200 is fabricated using the method 600.

Figure 38:
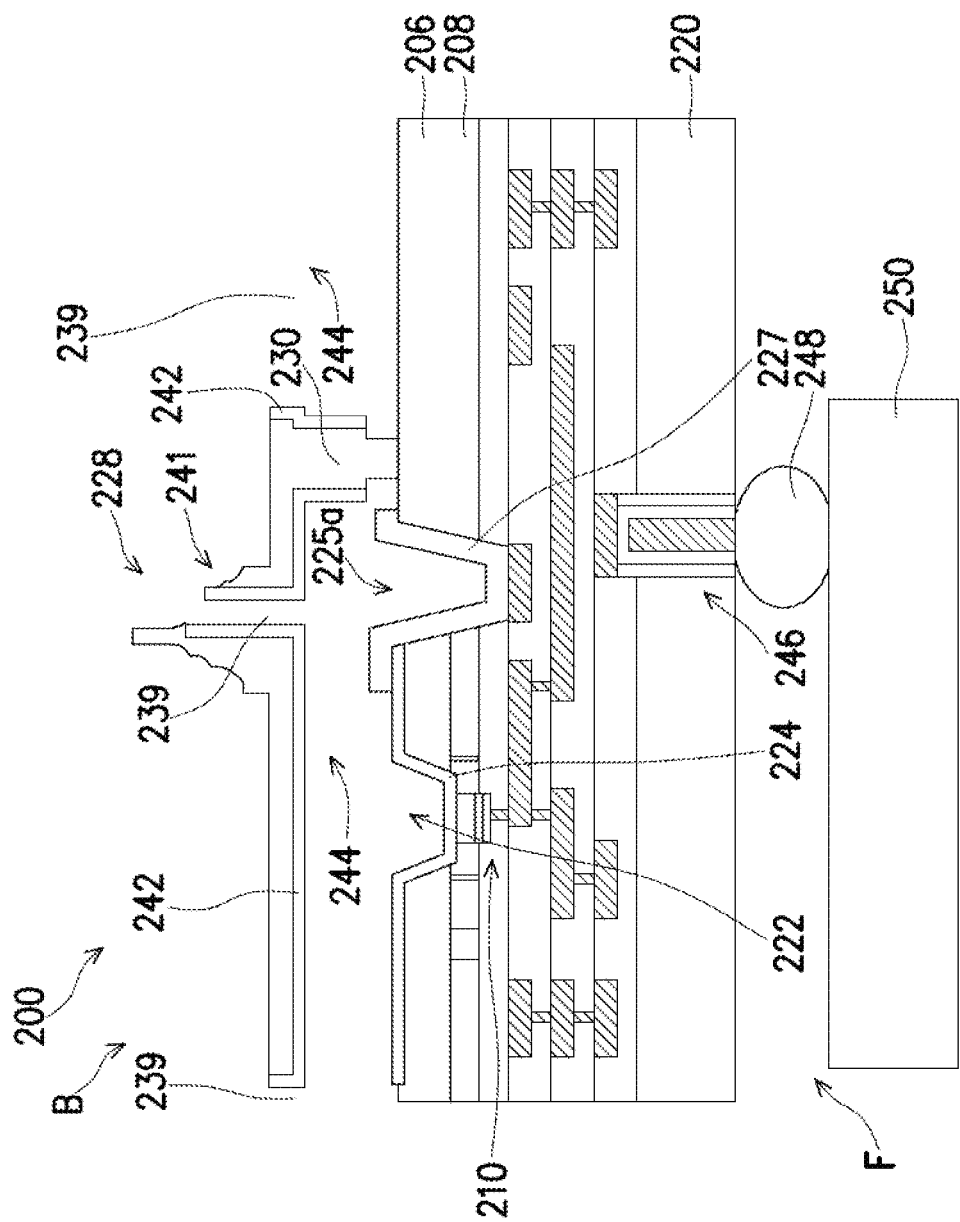

Alternatively as shown in FIG. 38, the biosensor system package 200 is connected to the separate chip 250 through the TSV structure formed at step 632 above. The separate chip may be bonded to the TSV structure by any suitable processes. Compared with the wire bonding mentioned above, the connection through the TSV structure is a more compact solution and has less resistance, capacitance, and inductance, which can achieve faster chip-to-chip data transmission with less noise, distortion, and power consumption. In one embodiment, the separate chip is bonded to the TSV structure by solder bump bonding. Solder Bumps are the small spheres of solder (solder balls) that are bonded to contact areas or pads of semiconductor devices. In one example, the solder bump bonding includes the following operations: placing solder bump(s) on the TSV structures; flipping the wafer; aligning the solder bump(s) with contact pad(s) of the separate chip; and reflowing the solder bump(s) in a furnace to establish the bonding between the TSV structure and the separate chip. In other embodiments, the separate chip may be bonded to the TSV structure by wire bonding. As shown in the example in FIG. 38, the separate chip 250 is bonded to the TSV structure 246 by solder bumps bonding (using a solder bump 248). As such, the biosensor system package 200 is fabricated using the method 600.

Embodiments in accordance with the disclosure include a biosensor system package. The biosensor system package includes: a transistor structure in a semiconductor layer having a front side and a back side, the transistor structure comprising a channel region; a buried oxide (BOX) layer on the back side of the semiconductor layer, wherein the buried oxide layer has an opening on the back side of the channel region, and an interface layer covers the back side over the channel region; a multi-layer interconnect (MLI) structure on the front side of the semiconductor layer, the transistor structure being electrically connected to the MLI structure; and a cap structure attached to the buried oxide layer, the cap structure comprising a microneedle.

Further embodiments include a biosensor system package. The biosensor system package includes: a biosensor structure in a semiconductor layer having a front side and a back side, the biosensor structure comprising a channel region and an interface layer covering the back side over the channel region; a buried oxide (BOX) layer on the back side of the semiconductor layer, wherein the buried oxide layer has an opening on the back side of the channel region, and the interface layer is exposed in the opening; a multi-layer interconnect (MLI) structure on the front side of the semiconductor layer, the biosensor structure being electrically connected to the MLI structure; a reference electrode connected to the MLI structure and configured to provide a reference potential; and a cap structure attached to the buried oxide layer, the cap structure comprising a microneedle.

Further embodiments include a method of fabricating a biosensor system package. The method includes: providing a substrate, the substrate comprising a semiconductor layer having a front side and a back side, a buried oxide (BOX) layer at the back side, and a bulk silicon layer at the back side; forming a transistor structure on the substrate, wherein a channel region of the transistor structure is in the semiconductor layer; forming a multi-layer interconnect (MLI)

structure on the front side of the semiconductor layer, wherein the MLI structure is electrically connected to the transistor structure; attaching a carrier substrate to the MLI structure; removing the bulk silicon layer; etching the buried oxide layer to form an opening at the back side over the channel region; depositing an interface layer on the back side over the channel region; fabricating a cap structure using a complementary metal-oxide-semiconductor (CMOS) compatible process flow; bonding the cap structure to the BOX layer; and creating a microneedle on the cap structure.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A biosensor system package comprising:
   a transistor structure in a semiconductor layer having a front side and a back side, the transistor structure comprising a channel region;
   a buried oxide (BOX) layer on the back side of the semiconductor layer, wherein the buried oxide layer has an opening over the channel region, and an interface layer covers the channel region;
   a multi-layer interconnect (MLI) structure on the front side of the semiconductor layer, the transistor structure being electrically connected to the MLI structure;
   a carrier substrate on the MLI structure;
   a through substrate via (TSV) structure extending though the carrier substrate and configured to provide an electrical connection between the MLI structure and a separate die; and
   a cap structure attached to the buried oxide layer, the cap structure comprising a silicon substrate attached to the buried oxide layer and a dielectric layer on the silicon substrate, the silicon substrate and the dielectric layer define a wall of a fluid chamber that has the dielectric layer lining at least part of the fluid chamber and the silicon substrate and the dielectric layer define a microneedle connected to the wall of the fluid chamber and that extends away from the wall of the fluid chamber, wherein the dielectric layer lines a microneedle channel of the microneedle that extends from the fluid chamber, through the wall of the fluid chamber and through the microneedle.

2. The biosensor system package of claim 1, wherein the TSV structure comprises:
   a conductive material;
   a liner isolating the conductive material from the carrier substrate; and
   a diffusion barrier layer between the conductive material and the liner.

3. The biosensor system package of claim 1, wherein the separate die is electrically connected to the TSV structure through a solder bump.

4. The biosensor system package of claim 1, wherein the fluid chamber is configured to accommodate fluid samples to be tested, and wherein the microneedle channel is fluidically coupled to the fluid chamber for inflow and outflow of the fluid samples.

5. The biosensor system package of claim 4, wherein the dielectric layer comprises:
   a high-k dielectric material layer covering a bottom and sidewalls of the fluid chamber.

6. The biosensor system package of claim 4, wherein the silicon substrate has bonding areas interfacing with bonding sites of the buried oxide layer.

7. The biosensor system package of claim 4, wherein the interface layer comprises a layer of capture reagent capable of binding a target analyte in the fluid samples.

8. The biosensor system package of claim 1, further comprising:
   a reference electrode connected to the MLI structure and configured to provide a reference potential.

9. The biosensor system package of claim 1, wherein the interface layer is a high-k material layer.

10. A biosensor system package comprising:
    a transistor structure in a semiconductor layer having a front side and a back side, the transistor structure comprising a channel region;
    a buried oxide (BOX) layer on the back side of the semiconductor layer, wherein the buried oxide layer has an opening over the channel region, and an interface layer covers the channel region;
    a multi-layer interconnect (MLI) structure on the front side of the semiconductor layer, the transistor structure being electrically connected to the MLI structure;
    a carrier substrate on the MLI structure;
    a through substrate via (TSV) structure extending though the carrier substrate and configured to provide an electrical connection between the MLI structure and a separate die; and
    a cap structure attached to the buried oxide layer, the cap structure comprising a silicon substrate attached to the buried oxide layer and a dielectric layer on the silicon substrate, the silicon substrate and the dielectric layer define a wall of a fluid chamber that has the dielectric layer lining at least part of the fluid chamber, the dielectric layer includes a high-k dielectric material layer covering a bottom and sidewalls of the fluid chamber, and the silicon substrate and the dielectric layer define a microneedle connected to the wall of the fluid chamber and that extends away from the wall of the fluid chamber, wherein the dielectric layer lines a microneedle channel of the microneedle that extends from the fluid chamber, through the wall of the fluid chamber and through the microneedle.

11. The biosensor system package of claim 10, wherein the TSV structure comprises:
    a conductive material;
    a liner isolating the conductive material from the carrier substrate; and
    a diffusion barrier layer between the conductive material and the liner.

12. The biosensor system package of claim 10, wherein the separate die is electrically connected to the TSV structure through a solder bump.

13. The biosensor system package of claim 10, wherein the silicon substrate has bonding areas interfacing with bonding sites of the buried oxide layer.

14. The biosensor system package of claim 10, wherein the interface layer comprises a layer of capture reagent capable of binding a target analyte in fluid samples.

15. The biosensor system package of claim 10, wherein the interface layer is a high-k material layer.

16. A biosensor system package comprising:
- a transistor structure in a semiconductor layer having a front side and a back side, the transistor structure comprising a channel region;
- a buried oxide (BOX) layer on the back side of the semiconductor layer, wherein the buried oxide layer has an opening over the channel region, and an interface layer covers the channel region;
- a multi-layer interconnect (MLI) structure on the front side of the semiconductor layer, the transistor structure being electrically connected to the MLI structure;
- a carrier substrate on the MLI structure;
- a through substrate via (TSV) structure extending though the carrier substrate and configured to provide an electrical connection between the MLI structure and a separate die; and
- a cap structure attached to the buried oxide layer, the cap structure comprising a silicon substrate attached to the buried oxide layer and a dielectric layer on the silicon substrate that has bonding areas interfacing with bonding sites of the buried oxide layer, the silicon substrate and the dielectric layer define a wall of a fluid chamber that has the dielectric layer lining at least part of the fluid chamber and the silicon substrate and the dielectric layer define a microneedle connected to the wall of the fluid chamber and that extends away from the wall of the fluid chamber, wherein the dielectric layer lines a microneedle channel of the microneedle that extends from the fluid chamber, through the wall of the fluid chamber and through the microneedle.

17. The biosensor system package of claim 16, wherein the TSV structure comprises:
- a conductive material;
- a liner isolating the conductive material from the carrier substrate; and
- a diffusion barrier layer between the conductive material and the liner.

18. The biosensor system package of claim 16, wherein the separate die is electrically connected to the TSV structure through a solder bump.

19. The biosensor system package of claim 16, wherein the interface layer comprises a layer of capture reagent capable of binding a target analyte in fluid samples.

20. The biosensor system package of claim 16, wherein the interface layer is a high-k material layer.

* * * * *